(12) United States Patent
Head et al.

(10) Patent No.: US 10,780,412 B2
(45) Date of Patent: Sep. 22, 2020

(54) METHODS OF SAMPLE PREPARATION

(71) Applicant: The Scripps Research Institute, La Jolla, CA (US)

(72) Inventors: Steven Robert Head, La Jolla, CA (US); Phillip T. Ordoukhanian, La Jolla, CA (US); Daniel R. Salomon, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 15/948,459

(22) Filed: Apr. 9, 2018

(65) Prior Publication Data

US 2019/0076813 A1    Mar. 14, 2019

Related U.S. Application Data

(63) Continuation of application No. 14/549,411, filed as application No. PCT/US2013/042106 on May 21, 2013, now Pat. No. 9,968,901.

(60) Provisional application No. 61/649,836, filed on May 21, 2012, provisional application No. 61/654,389, filed on Jun. 1, 2012, provisional application No. 61/716,378, filed on Oct. 19, 2012, provisional application No. 61/749,871, filed on Jan. 7, 2013, provisional application No. 61/763,424, filed on Feb. 11, 2013, provisional application No. 61/763,441, filed on Feb. 11, 2013.

(51) Int. Cl.
| | | |
|---|---|---|
| *B01J 19/00* | (2006.01) | |
| *C12Q 1/6874* | (2018.01) | |
| *C40B 50/06* | (2006.01) | |
| *C40B 40/06* | (2006.01) | |

(52) U.S. Cl.
CPC ........ *B01J 19/0046* (2013.01); *C12Q 1/6874* (2013.01); *B01J 2219/0059* (2013.01); *B01J 2219/00709* (2013.01); *B01J 2219/00722* (2013.01); *C40B 40/06* (2013.01); *C40B 50/06* (2013.01)

(58) Field of Classification Search
None
See application file for complete search history.

(56) References Cited

U.S. PATENT DOCUMENTS

| | | |
|---|---|---|
| 4,318,846 A | 3/1982 | Khanna et al. |
| 4,437,975 A | 3/1984 | Gillespie et al. |
| 4,683,195 A | 7/1987 | Mullis et al. |
| 4,683,202 A | 7/1987 | Mullis |
| 4,757,141 A | 7/1988 | Fung et al. |
| 4,988,617 A | 1/1991 | Landegren et al. |
| 5,066,580 A | 11/1991 | Lee |
| 5,091,519 A | 2/1992 | Cruickshank |
| 5,151,507 A | 9/1992 | Hobbs, Jr. et al. |
| 5,188,934 A | 2/1993 | Menchen et al. |
| 5,242,794 A | 9/1993 | Whiteley et al. |
| 5,270,184 A | 12/1993 | Walker et al. |
| 5,366,860 A | 11/1994 | Bergot et al. |
| 5,399,491 A | 3/1995 | Kacian et al. |
| 5,405,746 A | 4/1995 | Uhlen |
| 5,409,818 A | 4/1995 | Davey et al. |
| 5,413,909 A | 5/1995 | Bassam et al. |
| 5,422,252 A | 6/1995 | Walker et al. |
| 5,494,810 A | 2/1996 | Barany et al. |
| 5,500,356 A | 3/1996 | Li et al. |
| 5,554,517 A | 9/1996 | Davey et al. |
| 5,648,245 A | 7/1997 | Fire et al. |
| 5,688,648 A | 11/1997 | Mathies et al. |
| 5,759,778 A | 6/1998 | Li et al. |
| 5,800,996 A | 9/1998 | Lee et al. |
| 5,847,162 A | 12/1998 | Lee et al. |
| 5,861,245 A | 1/1999 | McClelland et al. |
| 5,990,479 A | 11/1999 | Weiss et al. |
| 6,027,923 A | 2/2000 | Wallace |
| 6,063,603 A | 5/2000 | Davey et al. |
| 6,207,392 B1 | 3/2001 | Weiss et al. |
| 6,210,891 B1 | 4/2001 | Nyren et al. |
| 6,251,303 B1 | 6/2001 | Bawendi et al. |

(Continued)

FOREIGN PATENT DOCUMENTS

| | | |
|---|---|---|
| CN | 102439177 A | 5/2012 |
| WO | WO-8706270 A1 | 10/1987 |

(Continued)

OTHER PUBLICATIONS

Ciprianay, B. et al. Real-Time Analysis and Selection of Methylated DNA by Flourescence-Activated Single Molecule Sorting in a Nanofluidic Channel. Proceedings of the National Acadamy of Sciences. May 29, 2012 (published online before print May 14, 2012), vol. 109, No. 22, pp. 8477-8482.

Drmanac et al. Human genome sequencing using unchained base reads on self-assembling DNA nanoarrays. Science. 2010; 327: 78-81.

Drmanac et al. Supporting Online Material for: Human genome sequencing using unchained base reads on self-assembling DNA nanoarrays. Published online at: www.sciencemag.org/cgi/content/full/1181498/DC1.

European Application No. 13793337.0 Partial Supplementary European Search Report dated Apr. 11, 2016.

(Continued)

*Primary Examiner* — Kaijiang Zhang
(74) *Attorney, Agent, or Firm* — Wilson Sonsini Goodrich & Rosati

(57) ABSTRACT

The present disclosure provides methods, compositions, and kits for methods that can improve techniques nucleic acid analysis, and can allow for more reliable and accurate targeted, multiplexed, high throughput sequencing. The methods, compositions, and kits can be used for sequencing target loci of nucleic acid. The methods, compositions, and kits disclosed herein can be used for assisted de novo targeted sequencing. The methods, compositions, and kits disclosed herein can also be used for library labeling for de novo sequencing and phasing.

8 Claims, 17 Drawing Sheets

Specification includes a Sequence Listing.

(56) References Cited

U.S. PATENT DOCUMENTS

| | | |
|---|---|---|
| 6,309,824 B1 | 10/2001 | Drmanac |
| 6,319,426 B1 | 11/2001 | Bawendi et al. |
| 6,322,901 B1 | 11/2001 | Bawendi et al. |
| 6,401,267 B1 | 6/2002 | Drmanac |
| 6,410,276 B1 | 6/2002 | Burg et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,576,291 B2 | 6/2003 | Bawendi et al. |
| 6,582,938 B1 | 6/2003 | Su et al. |
| 6,828,100 B1 | 12/2004 | Ronaghi |
| 6,833,246 B2 | 12/2004 | Balasubramanian |
| 6,864,052 B1 | 3/2005 | Drmanac et al. |
| 6,911,345 B2 | 6/2005 | Quake et al. |
| 7,232,656 B2 | 6/2007 | Balasubramanian et al. |
| 7,459,311 B2 | 12/2008 | Nyren et al. |
| 7,648,824 B2 | 1/2010 | Nyren et al. |
| 7,670,810 B2 | 3/2010 | Gunderson et al. |
| 8,114,978 B2 | 2/2012 | Jones et al. |
| 8,168,385 B2 | 5/2012 | Brenner |
| 9,968,901 B2 | 5/2018 | Head |
| 2002/0045045 A1 | 4/2002 | Adams et al. |
| 2003/0017264 A1 | 1/2003 | Treadway et al. |
| 2003/0143599 A1 | 7/2003 | Makarov et al. |
| 2005/0191656 A1 | 9/2005 | Drmanac et al. |
| 2006/0252060 A1 | 11/2006 | Willis et al. |
| 2007/0207482 A1 | 9/2007 | Church et al. |
| 2007/0264642 A1 | 11/2007 | Willis et al. |
| 2009/0018024 A1 | 1/2009 | Church et al. |
| 2009/0036325 A1 | 2/2009 | McKernan et al. |
| 2010/0105052 A1 | 4/2010 | Drmanac et al. |
| 2010/0222238 A1 | 9/2010 | Smith et al. |
| 2010/0273219 A1 | 10/2010 | May et al. |
| 2010/0311064 A1* | 12/2010 | Oliphant et al. ..... C12Q 1/6834 435/6.11 |
| 2017/0247689 A1 | 8/2017 | Brown |

FOREIGN PATENT DOCUMENTS

| | | |
|---|---|---|
| WO | WO-9006995 A1 | 6/1990 |
| WO | WO-2011142836 A9 | 1/2012 |

OTHER PUBLICATIONS

Grillo et al., 11 CLEANUP: a fast computer program for removing redundancies from nucleotide sequence databases BIOINFORMATICS, 12 (1): 1-8.

Guatelli et al. Isothermal, in vitro amplification of nucleic acids by a multienzyme reaction modeled after retroviral replication. PNAS USA 87(5):1874-1878 (1990).

Hamady, M. et al. Error-Correcting Barcoded Primer for Pyrosequencing Hundreds of Seamples in Multiplex. Nat. Methods Feb. 10, 2008, vol. 5, No. 3 pp. 235-237.

Jeppe et al., Discarding duplicate ditags in Long SAGE analysis may introduce significant error, BMC Bioinformatics, Biomed Central, (1); 1-12 (Mar. 14, 2007).

Kienzler, R. et al. Large-Scale DNA Sequence Analysis in the Cloud: A Stream-Based Approach. Euro-Par 20122: Parallel Processing Workshops Lecture Notes in Computer Science. Jan. 2012 vol. 7156, pp. 467-476.

Kim S., et al. Solid phase capturable dideoxynucleotides for multiplex genotyping using mass spectrometry. Nucleic Acids Research 30(16); e85 (2002).

Landegren et al., A ligase-mediated gene detection technique. Science vol. 241, No. 4869, pp. 1077-1080, Aug. 26, 1988.

Li et al., A photocleavable fluorescent nucleotide for DNA sequencing and analysis. Proc. Natl. Acad. Sci., 100: 414-419 (2003).

Makrigiorgos, et al., A PCR-Based amplification method retaining quantative difference between two complex genomes. Nature Biotech, vol. 20, No. 9, pp. 936-939 (Sep. 2002).

Meyer, M. et al. Targeted High-Throughput Sequencnig of Tagged Nucleic Acid Samples. Nucleic Acids Research. Aug. 1, 2007, vol. 35, No. 15, e97.

Nunez et al. Application of Circular Ligase to Provide Template for Rolling Circle Amplification of Low Amounts of Fragmented DNA. FBI Publication Sep. 2002.

Orsouw, Nathalie J. et al. Complexity Reduction of Polymorphic Sequences (CRoPS): A Novel Approach for Large-Scale Polymorphism Discovery in Complex Genomes.PLoS One, 2(11); e1172 (Jan. 1, 2007).

PCT/US2013/042106 International Preliminary Report on Patentability dated Nov. 25, 2014.

PCT/US2013/042106 International Search Report and Written Opinion dated Oct. 17, 2013.

Qiu, Chunmei et al. Design and synthesis of cleavable biotinylated dideoxynucleotides for DNA sequencing by matrix-assisted laser desorption/ionization time-of-flight mass spectrometry. Analytical Biochemistry, 427(2); 193-201 (Apr. 25, 2012).

Quan et al. Parallel on-chip gene synthesis and application to optimization of protein expression. Nat. Biotechnol. 29:449-452 (2011), E-published Apr. 24, 2011.

Supplementary European search report and opinion dated Sep. 5, 2016 for EP Application No. 13793337.

Tong, AK., et al. Single nucleotide polymorphism detection by combinatorial fluorescence energy transfer tags and biotinylated dideoxynucleotides. Nucleic Acids Research 30(5); e19 (2002).

U.S. Appl. No. 14/549,411 Non-Final Office Action dated Jun. 13, 2017.

Van Dijk, Erwin L., et al. Library preparation methods for next-generation sequencing: tone down the bias. Experimental Cell Research, 322(1); 12-20 (Mar. 1, 2014).

Wachter A., et al. A 50 SNP-multiplex mass spectrometry assay for human indentification. Forensic Science International: Genetics Supplemental Series, 1(1); 487-489 (Aug. 1, 2008).

Walker et al., SEALS: a system for easy analysis of lots of sequences, International Conference on Intelligent Systems for Molecular, Jan. 1, 1997, XP055295893.

Walker et al., Strand displacement amplification—an isothermal, in vitro DNA amplification technique. Nucleic Acids Res. 20(7):1691-6 (1992).

Wetmur, James G., DNA Probes: Applications of the Principles of Nucleic Acid Hybridization. Critical Reviews in Biochemistry and Afolecular Biology, vol. 26, No. 3/4, pp. 227-259 (1991).

Wilhelm, B. et al. RNA-SEQ-quantitative measurement of expression through massively parallel RNA-sequencing. Methods, 48(3); 249-257 (Jul. 1, 2009).

Wu & Wallace, The ligation amplification reaction (LAR)—Amplification of specific DNA sequences using sequential rounds of template-dependent ligation. (Ligase Chain Reaction (LR)) Genomics, vol. 4, No. 4, pp. 560-569, May 1989.

Kim et al. Digital genotyping using molecular affinity and mass spectrometry. Nat Rev Gene 4(12):1001-1008 (2003).

* cited by examiner

FIG. 2A  *200*

Donor Primer
(D)

*205*          *210*         *215*

5'-ATCGTCGA-CTGAC-NNNNNNNN-3'

UNIVERSAL A   MOLECULAR  RANDOM
                      LABEL

Donor Primer

FIG. 2B  *240*

Acceptor Probe
(A)

*220*         *225*        *230*        *235*

5'-NNNNNNNN-CTGAC-ATCGTCGA-3'CAP

RANDOM    MOLECULAR  UNIVERSAL B
                LABEL

Acceptor Probe

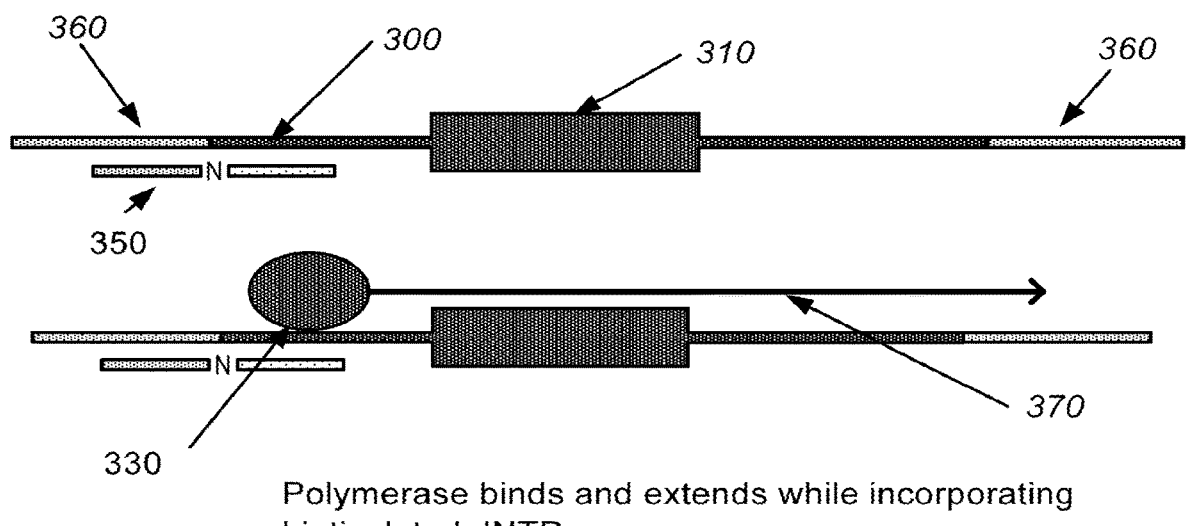
Polymerase binds and extends while incorporating biotinylated dNTPs
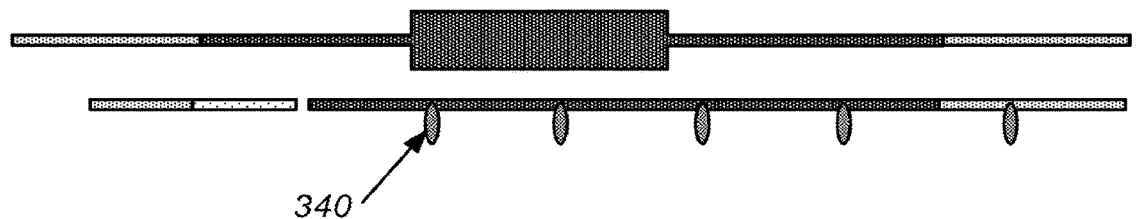
FIG. 3A

300
Targets are released
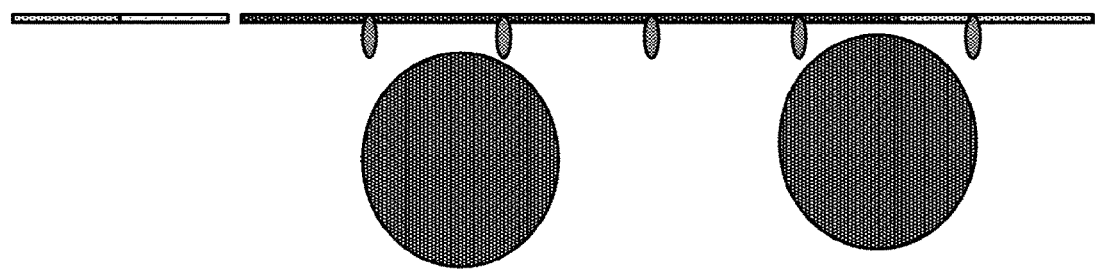
*FIG. 3C*

Truseq standard construct - multiplex (Red= barcode)
AATGATACGGCGACCACCGAGATCTACACTCTTTCCCTACACGACGCTCTTCCGATCT-XXX-AGATCGGAAGAGCACACGTCTGAACTCCAGTCAC
TTACTATGCCGCTGGTGGCTCTAGATGTGAGAAAGGGATGTGCTGCGAGAAGGCTAGA-XXX-TCTAGCCTTCTCGTGTGCAGACTTGAGGTCAGTG

ATCTCGTATGCCGTCTTCTGCTTG
TAGAGCATACGGCAGAAGACGAAC

Three oligos to order: Rapel 1 & 2 and PCR1 (PCR2 we already have).

Rapel-1:
barcode 13

Rapel-2:
barcode 17

UUT-TCCCTACACGACGCTCTTCCGATCT-AGTCAA-N8-3'
--UT-AGGGATGTGCTGCGAGAAGGCTAGA-5'

P-N8-AGATCGGAAGAGCACACGTCTGAACTCCAGTCAC-GTAGAG-
ATCTCGTATGCCGTCTTCTGCTTG-amino-3'

PCR1
AATGATACGGCGACCACCGAGATCTACACTCTTTCCCTACACGACGCTCTTCCGATCT

PCR2
CAAGCAGAAGACGGCATACGAGAT

IDT order

Rapel 1: AGATCGGAAGAGCGTCGTGTAGGGAT/ideoxyU//ideoxyU//TTCCCTACACGACGCTCTTCCGATCTAGTC
AANNNNNNNN Rapel 2: /5Phos/NNNNNNNNNAGATCGGAAGAGCACACGTCTGAACTCCAGTCACGTAGAGATCTCGTATGCCGTCTTCTGCTTG

PCR 1: AATGATACGGCGACCACCGAGATCTACACTCTTTCCCTACACGACGCTCTTCCGATCT

FIG. 14

SEQUENCE LISTING

<160> NUMBER OF SEQ ID NOS: 14

<210> SEQ ID NO 1
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (58)..(58)
<223> OTHER INFORMATION: a, c, t, g, unknown or other

<400> SEQUENCE: 1

```
gatcggaaga gcacacgtct gaactccagt cacatctcgt atgccgtctt ctgcttgn      58
```

```
<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (58)..(58)
<223> OTHER INFORMATION: a, c, t, g, unknown or other

<400> SEQUENCE: 2
caagcagaag acggcatacg agatgtgact ggagttcaga cgtgtgctct tccgatcn      58
```

```
<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(21)
<223> OTHER INFORMATION: a, c, t, g, unknown or other

<400> SEQUENCE: 3
atcgtcgact gacnnnnnnn n                                              21
```

```
<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(8)
<223> OTHER INFORMATION: a, c, t, g, unknown or other

<400> SEQUENCE: 4
nnnnnnnnct gacatcgtcg a                                              21
```

```
<210> SEQ ID NO 5
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(21)
<223> OTHER INFORMATION: a, c, t, g, unknown or other
<220> FEATURE:
<221> NAME/KEY: modified_base
<222> LOCATION: (75)..(82)
<223> OTHER INFORMATION: a, c, t, g, unknown or other

<400> SEQUENCE: 5
atcgtcgact gacnnnnnnn nctcgatcgc tagactagct cgatcgattt cgatcgctat    60
cgcgtagcta gctannnnnn nnctgacatc gtcga                               95
```

```
<210> SEQ ID NO 6
<211> LENGTH: 125
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (59)..(61)
<223> OTHER INFORMATION: a, c, t, g, unknown or other
<220> FEATURE:
<221> NAME/KEY: modified_base
<222> LOCATION: (96)..(101)
<223> OTHER INFORMATION: a, c, t, g, unknown or other

<400> SEQUENCE: 6
aatgatacgg cgaccaccga gatctacact ctttccctac acgacgctct tccgatctnn      60
nagatcggaa gagcacacgt ctgaactcca gtcacnnnnn natctcgtat gccgtcttct     120
gcttg                                                                 125

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (35)..(42)
<223> OTHER INFORMATION: a, c, t, g, unknown or other

<400> SEQUENCE: 7
uuttccctac acgacgctct tccgatctag tcaannnnnn nn                         42

<210> SEQ ID NO 8
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 8
nnnnnnnnag atcggaagag cacacgtctg aactccagtc acgtagagat ctcgtatgcc      60
gtcttctgct tg                                                         72

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
agatcggaag agcgtcgtgt agggatu                                         27

<210> SEQ ID NO 10
```

```
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aatgatacgg cgaccaccga gatctacact ctttccctac acgacgctct tccgatct        58

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caagcagaag acggcatacg agat                                              24

<210> SEQ ID NO 12
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (62)..(69)
<223> OTHER INFORMATION: a, c, t, g, unknown or other

<400> SEQUENCE: 12
agatcggaag agcgtcgtgt agggatuuut tccctacacg acgctcttcc gatctagtca       60 annnnnnnn                                                               69

<210> SEQ ID NO 13
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 13
nnnnnnnnag atcggaagag cacacgtctg aactccagtc acgtagagat ctcgtatgcc       60
gtcttctgct tg                                                           72

<210> SEQ ID NO 14
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aatgatacgg cgaccaccga gatctacact ctttccctac acgacgctct tccgatct        58
```

METHODS OF SAMPLE PREPARATION

CROSS-REFERENCE TO RELATED APPLICATIONS

The present application is a continuation of U.S. patent application Ser. No. 14/549,411, filed Nov. 20, 2014, which is a U.S. 371 of international PCT/US13/42106, filed May 21, 2013, which claims the benefit of U.S. Provisional Patent Application No. 61/763,441, filed on Feb. 11, 2013, U.S. Provisional Patent Application No. 61/763,424, filed on Feb. 11, 2013, U.S. Provisional Patent Application No. 61/749,871, filed on Jan. 7, 2013, U.S. Provisional Patent Application No. 61/716,378, filed on Oct. 19, 2012, U.S. Provisional Patent Application No. 61/654,389, filed on Jun. 1, 2012, and U.S. Provisional Patent Application No. 61/649,836, filed on May 21, 2012, the entire contents of each of which are incorporated herein by reference.

BACKGROUND OF THE INVENTION

Several biological applications involve nucleic acid sequencing, including next-generation sequencing. Next-generation sequencing can amplify clonal errors. Additionally, data-analysis of next generation sequencing can require the use of a reference genome. Methods for targeting specific regions of a genome for sequencing analysis are needed.

Current next generation sequencing platforms pose a problem for genome assembly and sequencer read alignment for longer sequences. Regions of repetitive sequence, homologous sequence, and variable sequence are not reliably mapped. A strategy of aligning to a reference is required for these short read sequencers, and this aligning step can dramatically increase bias and the computational steps required to obtain reliable sequencing results for longer read lengths. There is a need in the art for improved methods and systems for targeting sequences of interest and preparing them for sequencing reactions of a longer read length.

SUMMARY OF THE INVENTION

In some embodiments, the disclosure provides for a method comprising spatially separating nucleic acid fragments of a nucleic acid; generating one or more amplicons, wherein the amplicons are generated by hybridizing a primer and a probe to a common strand of the nucleic acid fragment; performing a primer extension reaction; ligating a product of the primer extension reaction with the probe to form the amplicons; associating the one or more amplicons with an identifier; and obtaining a sequence of the amplicon.

In some embodiments, amplicons may be amplified. Amplification of amplicons may be performed by linear amplification, non-linear amplification or rolling circle amplification.

In some embodiments, at least one amplicon is ligated to at least one different amplicon. In some cases, an indentifier may comprise a molecular barcode, a nucleic acid sequence, a nucleic acid not A, T, C or G. In some cases, the identifier is located at the 5' end of the amplicon. In some cases, the identifier is located at the 3' end of the amplicons. In some cases, the identifier is associated with the amplicon through amplification of the amplicon.

In some embodiments, the nucleic acid is selected from a group consisting of: DNA, RNA, cDNA and genomic DNA. In some cases, the nucleic acid is fragmented by method from a group consisting of: sonication, enzymatic digestion, heat, exposure to UV light, repetitive pipetting, and nebulization.

In some embodiments, spatially separating the nucleic acid fragments is performed in partitions. In some cases, spatially separating the nucleic acid fragments is performed by tethering the nucleic acid to a solid or semi-solid support. In some cases the nucleic acid fragment is hybridized to a primer tethered to a solid or semi-solid support, wherein the primer comprises the identifier. In some cases the nucleic acid fragment is hybridized to a probe tethered to a solid or semi-solid support, wherein the probe comprises the identifier. In some cases, the solid or semi-solid support is addressed.

In some embodiments the probe comprises the identifier. In some cases the probe comprises one or more adapter sequences. In some cases the probe hybridizes to a target nucleic acid. In some cases the probe comprises degenerate sequence. In some cases the probe comprises a synthetic nucleotide. In some cases the probe comprises a primer.

In some embodiments the primer comprises the identifier. In some cases the primer comprises one or more adapter sequences. In some cases the primer hybridizes to a target nucleic acid. In some cases the primer comprises degenerate sequence. In some cases the primer comprises a synthetic nucleotide. In some cases the amplicons are associated with a unique identifier. In some cases the identifier represents an individual partition.

In some embodiments the sequence of the amplicons is performed by massively parallel sequencing. In some cases a computing device is used to generate a consensus sequence of all or part of the nucleic acid fragment, from sequence reads comprising the identifier.

In some embodiments a computing device is used to generate a consensus sequence of all or part of the nucleic acid, from sequence reads comprising the identifier. In some cases a computing device is used to generate a consensus sequence without comparing the consensus sequence to a reference.

In some embodiments the consensus sequence has at least 1×, 5×, 10×, or 50× depth of coverage.

In some embodiments method of the disclosure provides for multiplexed analysis for multiple nucleic acid fragments. In some cases, the method is multiplexed for at least 2 nucleic acid fragments, at least 10 nucleic acid fragments, at least 100 nucleic acid fragments, at least 10000 nucleic acid fragments, at least 100000 nucleic acid fragments, or at least 1000000 nucleic acid fragments.

In some embodiments the product of the primer extension reaction is at least 100 nucleotides, at least 1000 nucleotides, or at least 10000 nucleotides.

In some embodiments, the disclosure provides for transmitting sequencing data generated, receiving sequencing data generated, storing sequencing data generated, comprising comparing or analyzing sequencing data generated, transmitting a report related to sequencing data generated, receiving a report related to sequencing data generated, storing a report related to sequencing data generated, storing a report related to sequencing data generated, comparing or analyzing a report related to sequencing data generated by methods of this disclosure. In some cases, the disclosure provides for transforming sequencing data to a report related to sequencing data using a computing device comprising non transitory computer readable media.

In some embodiments, the primer or probe is specific to one or more regions of the nucleic acid fragment. In some cases, the primer or probe is at least 50% complementary to one or more regions of the nucleic acid fragment. In some cases, the primer or probe is at least 75% complementary to one or more regions of the nucleic acid fragment. In some cases, the primer or probe is at least 90% complementary to one or more regions of the nucleic acid fragment.

In some embodiments, one or more amplicons are linked to form a contiguous sequence. In some cases the disclosure provides for performing a primer extension reaction comprises addition of a strand displacing polymerase. In some cases the disclosure provides for performing a primer extension reaction to form a primer extension product, wherein the primer extension product comprises an affinity conjugate and wherein the primer extension product comprises a target sequence.

In some embodiments the disclosure provides for performing a primer extension reaction to form a primer extension product and performing affinity purification of the primer extension product using the affinity conjugate. In some cases the affinity conjugate is biotin. In some cases the affinity purification of the primer extension product is performed using streptavidin.

In some embodiments, the disclosure provides for a method comprising: obtaining a nucleic acid, wherein the nucleic acid comprises a target sequence; hybridizing a TELA primer and a TELA probe to a common strand of the nucleic acid; performing a primer extension reaction; ligating a product of the primer extension reaction with the TELA probe to form a ligation product comprising the target sequence; and sequencing the target sequence.

In some embodiments the target sequence is at least 30% of the ligation product. In some cases, one or more ligation products are linked to form a contiguous sequence.

In some embodiments, the disclosure provides for a method comprising: obtaining a nucleic acid library; ligating an adapter sequence to one or more nucleic acids of the nucleic acid library; hybridizing a primer to the adapter sequence, wherein the primer comprises a spacer region and a locus specific region; performing a primer extension reaction to form a primer extension product, wherein the primer extension product comprises an affinity conjugate and wherein the primer extension product comprises a target sequence; performing affinity purification of the primer extension product using the affinity conjugate.

In some embodiments the nucleic acid library is fragmented gDNA. In some cases, the nucleic acid library is expressed sequences. In some cases, the nucleic acid library is epigenetically sorted. In some embodiments the primer extension product is sequenced.

In some cases the nucleic acid library comprises at least 2, at least 10, at least 100, at least 10000, at least 100000, or at least 1000000 nucleic acid fragments.

In some cases, the nucleic acid is fragmented by method from a group consisting of: sonication, enzymatic digestion, heat, exposure to UV light, repetitive pipetting, and nebulization. The method of claim 1 further comprising amplifying a nucleic acid to generate the nucleic acid library.

In some embodiments, the disclosure provides for methods comprising amplifying the adaptor ligated nucleic acid library. In some cases, the amplifying is linear. In some cases, the amplifying is performed by rolling circle amplification. In some cases, the amplifying is non-linear. In some cases the primer extension product comprises an identifier.

In some embodiments the primer extension product comprises a molecular barcode. In some cases, the primer extension product comprises a nucleic acid sequence. In some cases, the primer extension product comprises a nucleic acid not A, T, C or G. In some cases the adaptor is located at the 5' end of the nucleic acid of the nucleic acid library. In some cases, the primer extension product is located at the 3' end of the nucleic acid of the nucleic acid library. In some cases the nucleic acid is selected from a group consisting of: DNA, RNA, cDNA and genomic DNA.

In some embodiments, the disclosure provides for methods in which the spacer region is degenerate or random sequence. In some cases, the spacer region comprises at least 1 nucleotide, at least 10 nucleotides, or 100 nucleotides.

In some cases, the spacer region comprises a molecular barcode. In some cases, the spacer region comprises a nucleic acid sequence. In some cases, the spacer region comprises a nucleic acid not A, T, C or G. In some cases, the spacer region comprises an enzymatic target sequence.

In some embodiments, the locus specific region is at least 50% complementary to a locus of the nucleic acid. In some cases, the locus specific region is at least 70% complementary to a locus of the nucleic acid. In some cases, the locus specific region is at least 80% complementary to a locus of the nucleic acid. In some cases, the locus specific region is at least 90% complementary to a locus of the nucleic acid. In some cases, the locus specific region is at least 99% complementary to a locus of the nucleic acid. In some cases, the locus specific region binds a locus of the nucleic acid upstream of the target sequence.

In some embodiments, the affinity conjugate is biotin. In some cases, the affinity purification of the primer extension product is performed using streptavidin.

In some embodiments, the disclosure provides for sequencing the primer extension product. In some cases the identifier represents a source of the sample from which the nucleic acid library was generated.

In some cases the sequence of the primer extension reaction is obtained by performing massively parallel sequencing. In some cases a computing device is used to generate a consensus sequence of all or part of the target sequence, from sequence reads comprising the identifier.

In some embodiments the consensus sequence has at least 1×, 5×, 10×, or 50× depth of coverage.

In some embodiments the disclosure provides for a method that is multiplexed for multiple samples or target sequences. In some cases the method is multiplexed for at least 2, 10, 100, 10000, 100000, 1000000, 1000000 samples or target sequences.

In some embodiments the product of the primer extension reaction is at least 100 nucleotides, at least 1000 nucleotides, or at least 10000 nucleotides.

In some embodiments, one or more primer extension products are linked to form a contiguous sequence.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A depicts examples of a donor primer (D).

FIG. 2B depicts examples of an acceptor probe (A).

FIG. 3A depicts a representation of a general TELA or mPEAR extension reaction.

FIG. 3C depicts a representation of release of TELA or mPEAR labeled products from an immobilized surface.

FIG. 14 depicts examples of sequences, including bar codes and adapter sequences.

DETAILED DESCRIPTION OF THE INVENTION

Figure 1A:
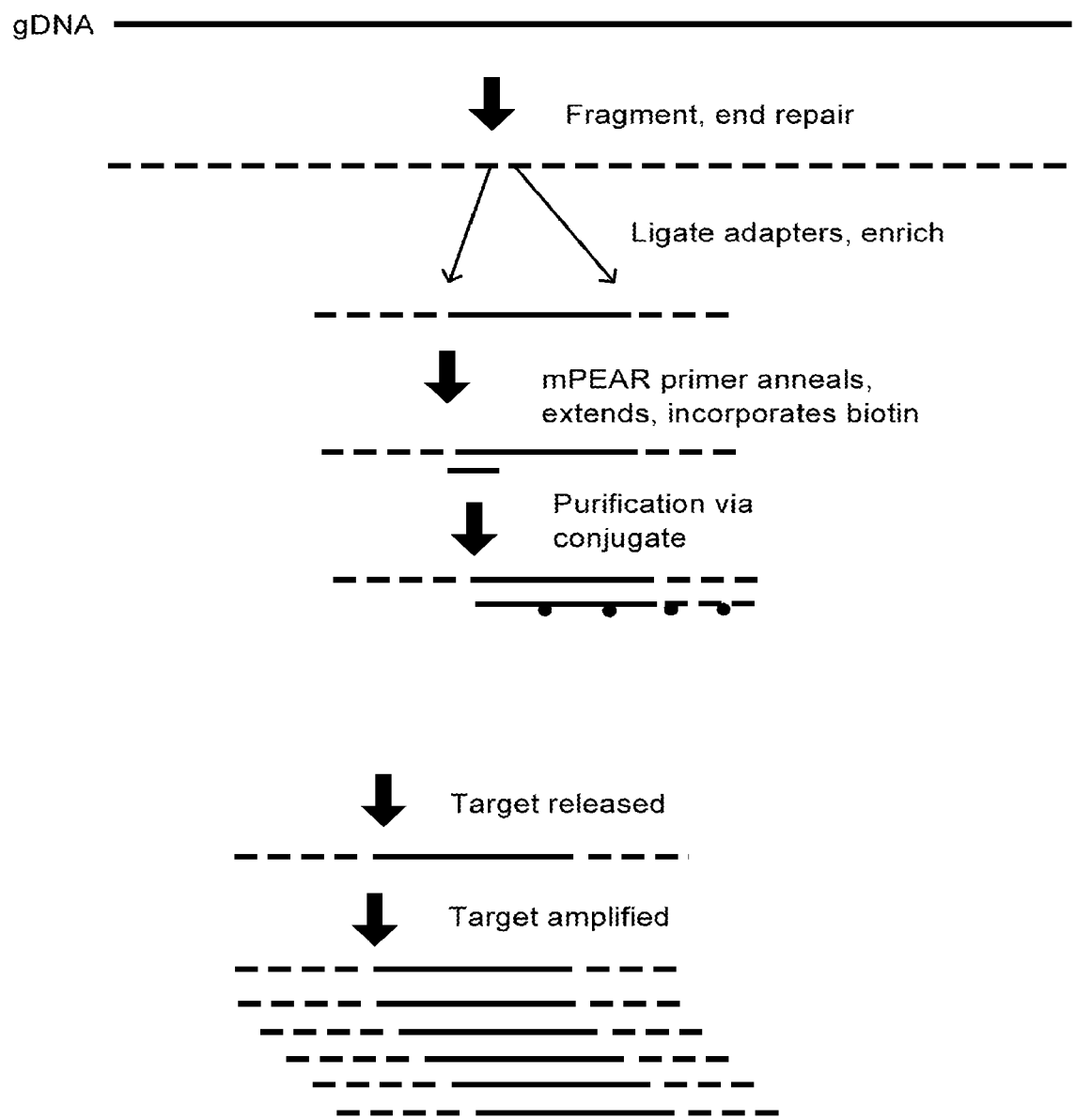
FIG. 1A depicts a schematic representation of a workflow involving mPEAR.

The present disclosure provides methods, compositions, and kits for methods that can improve techniques nucleic acid analysis, and can allow for more reliable and accurate targeted, multiplexed, high throughput sequencing. The methods, compositions, and kits can be used for sequencing target loci of nucleic acid. The methods, compositions, and kits disclosed herein can be used for assisted de novo targeted sequencing. The methods, compositions, and kits disclosed herein can also be used for library DNA/RNA labeling for true de novo sequencing and phasing.

I. DEFINITIONS

"Affinity conjugate" as described herein provides use of specific interactions between two molecules for the purification of a target molecule. An affinity ligand having affinity for a target molecule may be attached to an insoluble support and functions as bait for capturing a target molecule. The target molecule may be covalently or non covalently to a conjugate molecule that interacts or binds to the affinity ligand. The affinity ligand can be any molecule that will bind the target without also binding other molecules in the solution.

"Amplified nucleic acid" or "amplified polynucleotide" can be any nucleic acid or poly nucleotide molecule whose amount has been increased at least two fold by any nucleic acid amplification or replication method performed in vitro as compared to its starting amount. For example, an amplified nucleic acid can be obtained from a polymerase chain reaction (PCR) which can, in some instances, amplify DNA in an exponential manner (e.g. 2). Amplified nucleic acid can also be obtained from a linear amplification. Amplified nucleic acid can be obtained by primer elongations. identify "Amplification product" can refer to a product resulting from an amplification reaction.

An "amplicon" can be a polynucleotide or nucleic acid that is the source and/or product of natural or artificial amplification or replication events.

The term "biological sample" or "sample" generally refers to a sample or part isolated from a biological entity. The biological sample may show the nature of the whole and examples include, without limitation, bodily fluids, dissociated tumor specimens, cultured cells, and any combination thereof. Biological samples can come from one or more individuals. One or more biological samples can come from the same individual. One non limiting example would be if one sample came from an individual's blood and a second sample came from an individual's tumor biopsy. Examples of biological samples can include but are not limited to, blood, serum, plasma, nasal swab or nasopharyngeal wash, saliva, urine, gastric fluid, spinal fluid, tears, stool, mucus, sweat, earwax, oil, glandular secretion, cerebral spinal fluid, tissue, semen, vaginal fluid, interstitial fluids, including interstitial fluids derived from tumor tissue, ocular fluids, spinal fluid, throat swab, breath, hair, finger nails, skin, biopsy, placental fluid, amniotic fluid, cord blood, emphatic fluids, cavity fluids, sputum, pus, micropiota, meconium, breast milk and/or other excretions. The samples may include nasopharyngeal wash. Examples of tissue samples of the subject may include but are not limited to, connective tissue, muscle tissue, nervous tissue, epithelial tissue, cartilage, cancerous or tumor sample, or bone. The sample may be provided from a human or animal. The sample may be provided from a mammal, vertebrate, such as murines, simians, humans, farm animals, sport animals, or pets. The sample may be collected from a living or dead subject. The sample may be collected fresh from a subject or may have undergone some form of pre-processing, storage, or transport.

"Bodily fluid" generally can describe a fluid or secretion originating from the body of a subject. In some instances, bodily fluids can be a mixture of more than one type of bodily fluid mixed together. Some non limiting examples of bodily fluids can be: blood, urine, bone marrow, spinal fluid, pleural fluid, lymphatic fluid, amniotic fluid, ascites, sputum, or a combination thereof.

"Complementary" or "complementarity" can refer to nucleic acid molecules that are related by base-pairing. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 90% to about 95% complementarity, and more preferably from about 98% to about 100% complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions. Hybridization temperatures are generally at least about 2° C. to about 6° C. lower than melting temperatures ($T_m$).

A "barcode" or "molecular barcode" can be a material for labeling. The barcode can label a molecule such as a nucleic acid or a polypeptide. The material for labeling can be associated with information. A barcode can be called a sequence identifier (i.e. a sequence-based barcode or sequence index). A barcode can be a particular nucleotide sequence. A barcode can be used as an identifier. A barcode can be a different size molecule or different ending points of the same molecule. Barcodes can include a specific sequence within the molecule and a different ending sequence. For example, a molecule that is amplified from the same primer and has 25 nucleotide positions is different than a molecule that is amplified and has 27 nucleotide positions. The addition positions in the 27mer sequence can be considered a barcode. A barcode can be incorporated into a polynucleotide. A barcode can be incorporated into a polynucleotide by many methods. Some non-limiting methods for incorporating a barcode can include molecular biology methods. Some non-limiting examples of molecular biology methods to incorporate a barcode are through primers (e.g. tailed primer elongation), probes (i.e. elongation with ligation to a probe), or ligation (i.e. ligation of known sequence to a molecule).

A barcode can be incorporated into any region of a polynucleotide. The region can be known. The region can be unknown. The barcode can be added to any position along the polynucleotide. The barcode can be added to the 5' end of a polynucleotide. The barcode can be added to the 3' end of the polynucleotide. The barcode can be added in between the 5' and 3' end of a polynucleotide. A barcode can be added with one or more other known sequences. One non limiting example is the addition of a barcode with a sequence adapter.

Barcodes can be associated with information. Some non-limiting examples of the type of information a barcode can be associated with information include: the source of a sample; the orientation of a sample; the region or container a sample was processed in; the adjacent polynucleotide; or any combination thereof.

In some cases, barcodes can be made from combinations of sequences (different from combinatorial barcoding) and can be used to identify a sample or a genomic coordinate and a different template molecule or single strand the molecular label and copy of the strand was obtained from. In some cases a sample identifier, a genomic coordinate and a specific label for each biological molecule may be amplified together.

Barcodes can be added before pooling of samples. When the sequences are determined of the pooled samples, the barcode can be sequenced along with the rest of the polynucleotide. The barcode can be used to associate the sequenced fragment with the source of the sample.

Barcodes can also be used to identify the orientation of a sample. One or more barcodes can be used together. Two or more barcodes can be adjacent to one another, not adjacent to one another, or any combination thereof.

Barcodes can be used for combinatorial labeling.

"Combinatorial labeling" can be a method by which two or more barcodes are used to label. The two or more barcodes can label a polynucleotide. The barcodes, each, alone can be associated with information. The combination of the barcodes together can be associated with information. In some cases a combination of barcodes can be used together to determine in a randomly amplified molecule that the amplification occurred from the original sample template and not a synthetic copy of that template "Degenerate" can refer to a nucleic acid or nucleic acid region that is comprised of random bases. The terms "degenerate" and "random" can be used interchangeably when referring to nucleic acid sequences (e.g. "degenerate primers" or "random primers" or "degenerate probes" or "random probes"). The degenerate region can be of variable length. The degenerate region can comprise some portion of the whole nucleic acid (e.g. a semi-degenerate primer). The degenerate region can comprise the whole nucleic acid (e.g. a "degenerate primer"). A degenerate nucleic acid mix, or semi-degenerate nucleic acid mix may be comprised of every possible combination of base pairs, less than every possible combination of base pairs, or some combination of base pairs, a few combinations of base pairs, or a single base pair combination. A degenerate primer mix, or semi-degenerate primer mix can comprise "Double stranded" can refer to two polynucleotide strands that have annealed through complementary base-pairing.

"Known oligonucleotide sequence" or "known oligonucleotide" or "known sequence" can refer to a polynucleotide sequence that is known. A known oligonucleotide sequence can correspond to an oligonucleotide that has been designed, e.g. a universal primer for next generation sequencing platforms (e.g., Illumina, 454), a probe, an adaptor, a tag, a primer, a molecular barcode sequence, an identifier. A known sequence can comprise part of a primer. A known oligonucleotide sequence may not actually be known by a particular user but can be constructively known, for example, by being stored as data which may be accessible by a computer. A known sequence may also be a trade secret that is actually unknown or a secret to one or more users but may be known by the entity who has designed a particular component of the experiment, kit, apparatus or software that the user is using.

"Library" can refer a collection of nucleic acid. A library can contain one or more target fragments. In some instances the target fragments can be amplified nucleic acids. In other instances, the target fragments can be nucleic acid that is not amplified. A library can contain nucleic acid that has one or more known oligonucleotide sequence(s) added to the 3' end, the 5' end or both the 3' and 5' end. The library may be prepared so that the fragments can contain a known oligonucleotide sequence that identifies the source of the library (e.g a molecular identification barcode identifying a patient or DNA source). In some instances, two or more libraries can be pooled to create a library pool. Libraries may also be generated with other kits and techniques such as transpon mediated labeling, or "fragmentation" as known in the art. Kits may be commercially available such as the Illumina Nextera kit.

"Locus specific" or "loci specific" can refer to one or more loci corresponding to a location in a nucleic acid molecule (e.g. a location within a chromosome or genome). In some instances, a loci can be associated with genotype. In some instances loci may be directly isolated and enriched from the sample, e.g., based on hybridization and/or other sequence-based techniques, or they may be selectively amplified using the sample as a template prior to detection of the sequence. In some instances, loci may be selected on the basis of DNA level variation between individuals, based upon specificity for a particular chromosome, based on CG content and/or required amplification conditions of the selected loci, or other characteristics that will be apparent to one skilled in the art upon reading the present disclosure. A locus may also refer to a specific genomic coordinate or location in a genome as denoted by the reference sequence of that genome.

"Long nucleic acid" can refer to a polynucleotide longer than 1, 2, 3, 4, 5, 6, 7, 8, 9, or 10 kilobases.

The term "melting temperature" or "$T_m$" commonly refers to the temperature at which a population of double-stranded nucleic acid molecules becomes half dissociated into single strands. Equations for calculating the $T_m$ of nucleic acids are well known in the art. One equation that gives a simple estimate of the $T_m$ value is as follows: $T_m$=81.5+16.6(log 10[Na$^+$])0.41(%[G+C])−675/n−1.0 m, when a nucleic acid is in aqueous solution having cation concentrations of 0.5 M or less, the (G+C) content is between 30% and 70%, n is the number of bases, and m is the percentage of base pair mismatches (see, e.g., Sambrook J et al., *Molecular Cloning, A Laboratory Manual,* 3rd Ed., Cold Spring Harbor Laboratory Press (2001)). Other references can include more sophisticated computations, which take structural as well as sequence characteristics into account for the calculation of $T_m$.

"Nucleotide" can refer to a base-sugar-phosphate combination. Nucleotides are monomeric units of a nucleic acid sequence (e.g. DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrative examples of dideoxyribonucleoside triphosphates include, but are not limited to, ddATP, ddCTP, ddGTP, ddITP, and ddTTP. A nucleotide may be unlabeled or detectably labeled by well known techniques. Fluorescent labels and their attachment to oligonucleotides are described in many reviews, including Haugland, *Handbook of Fluorescent Probes and Research Chemicals,* 9th Ed., Molecular Probes, Inc., Eugene Oreg. (2002); Keller and Manak, *DNA Probes,* 2nd Ed., Stockton Press, New York (1993); Eckstein, Ed., *Oligonucleotides and Analogues: A Practical Approach,* IRL Press, Oxford (1991); Wetmur, *Critical Reviews in Biochemistry and Molecular Biology,* 26:227-259 (1991); and the like. Other methodologies applicable to the invention are disclosed in the following sample of references: Fung et al., U.S. Pat. No. 4,757,141; Hobbs, Jr., et al., U.S. Pat. No. 5,151,507; Cruickshank, U.S. Pat. No. 5,091,519; Menchen et al., U.S. Pat. No. 5,188,934; Begot et al., U.S. Pat. No. 5,366,860; Lee et al., U.S. Pat. No. 5,847,162; Khanna et al., U.S. Pat. No. 4,318,846; Lee et al., U.S. Pat. No. 5,800,996; Lee et al., U.S. Pat. No. 5,066,580: Mathies et al., U.S. Pat. No. 5,688,648; and the like. Labeling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; and 2003/0017264. Detectable labels include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides include [R6G]dUTP, [TAMRA]dUTP, [R110]dCTP, [R6G]dCTP, [TAMRA] dCTP, [JOE]ddATP, [R6G]ddATP, [FAM]ddCTP, [R110] ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosomee Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be, e.g., biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g. biotin-11-dUTP, biotin-16-dUTP, biotin-20-dUTP).

"Polymerase" can refer to an enzyme that links individual nucleotides together into a strand, using another strand as a template.

"Polymerase chain reaction" or "PCR" can refer to a technique for replicating a specific piece of selected DNA in vitro, even in the presence of excess non-specific DNA. Primers are added to the selected DNA, where the primers initiate the copying of the selected DNA using nucleotides and, typically, Taq polymerase or the like. By cycling the temperature, the selected DNA is repetitively denatured and copied. A single copy of the selected DNA, even if mixed in with other, random DNA, can be amplified to obtain thousands, millions, or billions of replicates. The polymerase chain reaction can be used to detect and measure very small amounts of DNA and to create customized pieces of DNA.

The term "polynucleotides" may include but is not limited to various DNA, RNA molecules, derivatives or combination thereof. These may include species such as dNTPs, ddNTPs, DNA, RNA, peptide nucleic acids, cDNA, dsDNA, ssDNA, plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA.

A "primer" generally refers to an oligonucleotide used to, e.g., prime nucleotide extension, ligation and/or synthesis, such as in the synthesis step of the polymerase chain reaction or in the primer extension techniques used in certain sequencing reactions. A primer may also be used in hybridization techniques as a means to provide complementarity of a locus to a capture oligonucleotide for detection of a specific nucleic acid region.

"Primer extension product" can refer to the product resulting from an primer extension reaction using a contiguous polynucleotide as a template, and a complementary or partially complementary primer to the contiguous sequence.

"Sequencing", "sequence determination" and the like generally refers to any and all biochemical methods that may be used to determine the order of nucleotide bases in a nucleic acid.

"Streptavidin" can refer to a protein or peptide that can bind to biotin and can include: native egg-white avidin, recombinant avidin, deglycosylated forms of avidin, bacterial streptavidin, recombinant streptavidin, truncated streptavidin, and/or any derivative thereof.

A "subject" generally refers to an organism that is currently living or an organism that at one time was living or an entity with a genome that can replicate. The methods, kits, and/or compositions of the disclosure can be applied to one or more single-celled or multi-cellular subjects, including but not limited to microorganisms such as bacterium and yeast; insects including but not limited to flies, beetles, and bees; plants including but not limited to corn, wheat, seaweed or algae; and animals including, but not limited to: humans; laboratory animals such as mice, rats, monkeys, and chimpanzees; domestic animals such as dogs and cats, agricultural animals such as cows, horses, pigs, sheep, goats; and wild animals such as bears, pandas, lions, tigers, leopards, elephants, zebras, giraffes, gorillas, dolphins, and whales. The methods of this disclosure can also be applied to germs or infectious agents, such as viruses or virus particles or one or more cells that have been infected by one or more viruses.

A "support" can be solid, semisolid, a bead, a surface. The support can mobile in a solution or can be immobile.

Unique identifier can mean a molecular bar code. Can be a percentage of a nucleic acid in a mix, such as dUTP.

II. POLYNUCLEOTIDE

A polynucleotide molecule can be treated. For example, a polynucleotide can be treated by chemical, physical, and/or enzymatic forces. The nucleic acid can be obtained from a subject or biological specimen. In some embodiments, the nucleic acid is DNA. The DNA can be of genomic origin or a cDNA library generated from a subject's RNA, or cell free DNA.

In some cases the polynucleotide may represent the entire genetic complement of an organism or subject. The polynucleotide can be genomic DNA molecules from a eukaryote which can include both intron and exon sequences (coding sequence), as well as non-coding regulatory sequences such as promoter and enhancer sequences. In some cases (e.g., DNA), molecules may comprise sub-sets of polynucleotide sequences of genomic DNA, such as, for example, particular chromosomes or fragments of chromosomes. The polynucleotide can be RNA or a combination of RNA and DNA, single stranded or double stranded. Sometimes, the sequence of the primary polynucleotide molecules can be unknown. In some embodiments the polynucleotide molecules are human genomic DNA molecules. In some embodiments, the polynucleotide is not genomic and can be from a mitochondria, a chloroplast, a plasmid a bacterium an/or a virus. In some cases the polynucleotide molecules are chromosomal or genomic DNA molecules from an organism that has been infected by a virus; in some instances, the viral infection may have caused alterations or insertions into the DNA.

The DNA molecules can be treated chemically or. In some cases polynucleotide molecules may be treated prior to, or subsequent to any fragmentation processes, and prior to or subsequent to the ligation of the adaptor sequences.

In many cases, fragmentation of polynucleotides, such as through mechanical shearing or enzymatic digestion results in fragments with a heterogeneous mix of blunt and 3'- and 5'-overhanging ends. In some cases, the methods can provide for repair of the fragment ends using methods or kits (e.g. Lucigen DNA terminator End Repair Kit) known in the art to generate ends that are designed for insertion, for example, into blunt sites of cloning vectors. In some cases, the methods of the disclosure provide for blunt ended fragment ends of the population of nucleic acids sequenced. Further, in some cases, the blunt ended fragment may also be phosphorylated or dephosphorylated to facilitate ligation. The phosphate moiety can be introduced via enzymatic treatment, for example, using a kinase, (e.g. T4 polynucleotide kinase) or the phosphate moiety can be dephosphorylated using an alkaline phosphatase.

In other cases, polynucleotide sequences are prepared with single overhanging nucleotides by, for example, activity of certain types of DNA polymerase such as Taq polymerase or Klenow exo minus polymerase which has a nontemplate-dependent terminal transferase activity that adds a single deoxynucleotide, for example, deoxyadenosine (A) to the 3' ends of, for example, PCR products. Such enzymes can be utilized to add a single nucleotide 'A' to the blunt ended 3' terminus of each strand of the target polynucleotide duplexes. Thus, an 'A' could be added to the 3' terminus of each end repaired duplex strand of the target polynucleotide duplex by reaction with Taq or Klenow exo minus polymerase, whilst the adaptor polynucleotide construct could be a T-construct with a compatible 'T' overhang present on the 3' terminus of each duplex region of the adaptor construct. This end modification also prevents self-ligation of both adaptor and target such that there is a bias towards formation of the combined ligated adaptor-target sequences.

Polynucleotides may be derived from a variety of sources including any species containing genetic material. In some cases samples may be derived from human, mammal, non-human mammal, ape, monkey, chimpanzee, reptilian, amphibian, avian, insect or various invertebrate sources. Samples may also be derived from microorganisms which may include but are not limited to unicellular organisms or multi-cellular organisms, bacteria, parasites, fungi, protists, algae, larvae, nematodes, worms, viruses and any combination thereof.

Further, samples may be extracted from variety of tissues and tissue types. Polynucleotides may be fetal in origin (e.g., fluid taken from a pregnant subject), or may be derived from tissue of the subject itself. Polynucleotides may also be found as cell free, or in a state not contained within cells. Polynucleotides can be extracted from, for example, a bodily fluid or tissue.

After collection of tissue or bodily fluids containing polynucleotides, samples may be treated. For example, the nucleic acid can be fragmented, purified, partially purified, and/or mixed with different polynucleotides from different sources, or any combination thereof. The starting material nucleic acid can comprise DNA of known origin or unknown origin, or a combination thereof. The starting material nucleic acid can comprise DNA of known origin and be mixed with DNA of known sequence. In some instances, the DNA of known sequence can act as a control or a sample reference.

Polynucleotide samples may be treated by any methods herein. Samples may be isolated and extracted using a variety of techniques known in the art. Isolation and purification of polynucleotides may be accomplished using any means, including, but not limited to, the use of commercial kits and protocols provided by companies such as Sigma Aldrich, Life Technologies, Promega, Affymetrix, IBI or the like. Kits and protocols may also be non-commercially available. In some cases, polynucleotides such as DNA may be isolated, extracted and prepared using commercially available kits such as Qiagen Qiamp® Circulating Nucleic Acid Kit protocol, Qiagen Qubit™ dsDNA HS Assay kit protocol, Agilent™ DNA 1000 kit, or TruSeq™ Sequencing Library Preparation; Low-Throughput (LT) protocols. Polynucleotide samples may be purified from a bodily fluid, such as blood, by using a Ficoll reagent, such as Ficoll-Paque PLUS GE Healthcare Life Sciences.

A plurality of polynucleotide sequences, such as that from a genome, may be first fragmented before subsequent steps as described herein. The size of the polynucleotide fragments, described in terms of length, may vary depending on the source of the target polynucleotide, the method used for fragmentation, and the desired application. In some cases one or more fragmentation steps may be used. For example, 1, 2, 3, 4, 5, 6, 7, 8, 9, 10, 11, 12, 13, 14, 15, or more fragmentation steps may be used.

Fragments may be about 1-10, 10-20, 20-50, 50-100, 50-200, 100-200, 200-300, 300-400, 400-500, 500-1000, 1000-5000, 5000-10000, 10000-100000, 100000-250000, or 250000-500000 nucleotides in length. Fragments can be at least about 10, 20, 100, 200, 300, 400, 500, 1000, 5000, 10000, 100000, 250000, 500000, or more nucleotides in length. Fragments can be less than about 10, 20, 100, 200, 300, 400, 500, 1000, 5000, 10000, 100000, 250000, 500000, nucleotides in length.

Numerous fragmentation methods are described herein and known in the art. For example, fragmentation may be performed through physical, mechanical or enzymatic methods. Physical fragmentation may include exposing a target polynucleotide to heat or to ultraviolet (UV) light. Mechanical disruption may be used to mechanically shear a target polynucleotide into fragments of the desired range. Mechanical shearing may be accomplished through a number of methods known in the art, including repetitive pipetting of the target polynucleotide, sonication and nebulization. Target polynucleotides may also be fragmented using enzymatic methods. In some cases, enzymatic digestion may be performed using enzymes such as using restriction enzymes.

Restriction enzymes may be used to perform specific or non-specific fragmentation of target polynucleotides. The methods may use one or more types of restriction enzymes, generally described as Type I enzymes, Type II enzymes, and/or Type III enzymes. Type II and Type III enzymes are generally commercially available and well known in the art. Type II and Type III enzymes recognize specific sequences of nucleotide within a double stranded polynucleotide sequence (a "recognition sequence" or "recognition site"). Upon binding and recognition of these sequences, Type II and Type III enzymes cleave the polynucleotide sequence. In some cases, cleavage will result in a polynucleotide fragment with a portion of overhanging single stranded DNA, called a "sticky end." In other cases, cleavage will not result in a fragment with an overhang, creating a "blunt end." The methods may comprise use of restriction enzymes that generate either sticky ends or blunt ends.

Restriction enzymes may recognize a variety of recognition sites in the target polynucleotide. Some restriction enzymes ("exact cutters") recognize only a single recognition site (e.g., GAATTC). Other restriction enzymes are more promiscuous, and recognize more than one recognition site, or a variety of recognition sites. Some enzymes cut at a single position within the recognition site, while others may cut at multiple positions. Some enzymes cut at the same position within the recognition site, while others cut at variable positions.

A polynucleotide may be exposed to two or more restriction enzymes simultaneously or sequentially. This may be accomplished by, for example, adding more than one restriction enzyme to a partition, or by adding one restriction enzyme to a partition, performing the digestion, deactivating the restriction enzyme (e.g., by heat treatment) and then adding a second restriction enzyme.

In some embodiments, the present invention can use dilution and spatial separation of target nucleic acid. In some instances, long fragments of nucleic acid are diluted before being spatially separated. Dilution can be accomplished by any method known in the art, such as by the addition of a diluent, such as water, or a suitable buffer. An exemplary method of dilution involves determining the concentration of the nucleic acid before dilution and calculating how much diluent to add so that the diluted sample can be partitioned into quantities that contain sub-genomic quantities of DNA (i.e. so that one sample contains less than one whole genome). In another exemplary method, dilution can be calculated so that the sample can be partitioned in a way that each partition contains approximately 1, 2, 3, 5, 10, 20, 50, 80, 100, 150, 200, 400, 500, 1000, 1500, 5,000, 10,000, 100,000, 1,000,000, 10,000,000, 100,000,000, 1,000,000, 000 fragments of nucleic acid. In another exemplary method, dilution is accomplished to facilitate partitioning sample so that approximately 1%, 2%, 5%, 10%, 15%, 20%, 30%, 50%, 70%, 80%, 95% or 100% of one copy of the genome can be separated.

Spatial separation can be accomplished by many methods known in the art, such as pipetting, micropipeting, or microfluidics. Partitions can be made of any known methods in the art, including plates (e.g. 96-well), mirofluidic chambers, micro-droplets, or simple spatial separation on solid surfaces such as silicon chips or beads or semi-solid surfaces. Oil and/or emulsions can be used for spatial separation.

In an exemplary method, dilution and spatial separation is conducted so that the there is a low probability that two partitions contain the same locus of DNA from each parental chromosome, or that multiple fragments from the same genomic locus will be extremely rare.

III. TARGETED SEQUENCING

Targeted sequencing can includes the ability to detect complex variation, avoiding clonal errors, and analysis that is less computationally burdensome (e.g. de novo sequencing). There are several embodiments of targeted sequencing. Some examples can include Primer Extension with Sequence Specific primers (PELA), Targeted RAndom Primer Extension Ligation and labeling (targeted RAPELLing). Targeted RAPELL can comprise a targeting step with the RAPELLing methods disclosed herein. Other targeted sequencing methods can include highly multiplexed PCR that can use biotin dUTP for long or short-range PCR. Another embodiment of targeted sequencing is Targeted Elongation Ligation and Amplification (TELA). Another embodiment of targeted sequencing is can be multiplexed primer extension and affinity reaction (mPEAR). Targeted sequencing methods can comprise a circularized rolling circle amplification (CRCA). In some cases, "targeted sequencing"? refers to any methods for the isolation and amplification of biologically relevant genomic locations for DNA sequencing. In some cases amplification is performed on conserved or functional elements of the genome that are relavant to assay by DNA sequencing. In some cases, this may include epigenetic information, such as methylation of nucleic acids, such as methylated DNA.

A. Targeted Primer Extension

Primer extension can be targeted by using primers that comprise a region that can hybridize to a known sequence. In some embodiments, the known sequence is within a target locus. In some embodiments, the known sequence is outside a target locus.

Primers can be designed to be tiled. A primer tiling strategy can be accomplished by using a plurality of unpaired or paired primers such that each primer can generate an amplicon. The primers can be designed such that multiple primers can generate multiple amplicons that can "tile" a loci. Tile can mean that the amplicons can overlap each other. The primers can be designed such that the amplicons generated essentially cover the entire target loci 1, 2, 3, 4, 5, 6, 7, 8, 9, 10, 11, 12, 13, 14, 15, 16, 17, 18, 19, 20, 21, 22, 23, 24, 25, 50, 100, 200, 300, 400, 500, 600, 700, 800, 900, 1000, 2000, 5000, 10,000, 50,000, 100,000, 500, 000, 1,000,000 times or more. In some instances, the locus can covered by amplifying regions of a longer target region. In some embodiments, the loci is a target loci. The primers can each hybridize to a region surrounding and including the target loci. The furthest upstream primer can be designed such that it is able to hybridize to a region starting approximately 30, 40, 50, 60, 70, 80, 90, 100, 120, 130, 140, 160, 180, 200, 250, 300, 350 400 or more nucleotides upstream of the target loci. In some embodiments, the starting region of the furthest upstream primer is between approximately 100 to approximately 200 nucleotides upstream of the target loci. The furthest downstream primer can be designed such that it is able to hybridize to a region starting approximately 30, 40, 50, 60, 70, 80, 90, 100, 120, 130, 140, 160, 180, 200, 250, 300, 350, 400 or more nucleotides downstream of the target loci. In some embodiments, the starting region of the furthest downstream primer is between approximately 100 to approximately 200 nucleotides downstream of the target loci.

In some cases primers may be designed to be complementary to a reference genome. The reference genome used may be a standard reference or an ethnic or population specific reference such as a reference that may include the major allele at each polymorphic position. In the case of SNPs, degenerate or N or every possible nucleotide of the four nucleotides may be used in synthesis of that position in the primer. A reference design may include assigning a "window" which may comprise a 100 bp sequence for the target location. In some cases, a window may be at least 1, 10, 20, 30, 40, 50, 60, 70, 80, 90, 100, 200, 300, 400, 500, 600, 700, 800, 900, 1000, 2000, 3000, 4000, 5000, 6000, 7000, 8000. 9000, 10000, 250000, or 500000 base pairs. In some cases, a window may be at most 1, 10, 20, 30, 40, 50, 60, 70, 80, 90, 100, 200, 300, 400, 500, 600, 700, 800, 900, 1000, 2000, 3000, 4000, 5000, 6000, 7000, 8000. 9000, 10000, 250000, or 500000 base pairs. Tiled windows may be assigned to a target locus such that the best performing probe based on length TM and specificity may be chosen from each window. Windows may be adjusted to account for any bias from defined windows. In some cases windows may overlap.

In some embodiments, the overlapping amplicons can cover essentially all of the target loci. In some embodiments, the overlapping amplicons can cover essentially all of a target loci and regions flanking the target region. The number of amplicons to cover a target locus can be approximately 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 500, 600, 700, 800, 900, 1000, 1500, 2000, 2500, 3000, 4000, 5000, 6000, 7000, 8000, 9000, 10,000 or more. The number of amplicons to cover a region can depend on the length of the region, the sequence variability within the region, the number of tandem repeats within the region, the percentage of CG bases in the region or other sequence or structural variations within the region that can affect sequencing quality. Typically, it may be preferable to have a larger number of amplicons covering a region to increase the depth and accuracy of the sequencing.

In some cases windows or tiles may be designed such that specific sequence motifs, such as CCG polynucleotides may cause sequencing chemistries to generate errors. The position of these polynucleotide sequences within a read may affect sequence quality. In some cases, if the sequence motifs are located near a solid surface, they may have a differential effect on the quality of the read, than if they were located at the end of a read. In some cases, adjusting the position at which these motifs are within the read produces a consensus and random error profile that may be corrected with the redundant read processing. This is an attribute that may not be available in PCR based approaches with identical read structure. PCR approaches may also incorporate the least troublesome sequence combination to avoid stuttering of polymerase during sequencing. Such a result may cause a CGG sequence interpretation during cluster amplification instead of the correct CCG configuration which is considered a systematic error.

Tiled strategies can also modify the error profile across a read at each position of the target (e.g. by tiled amplicons having different sequencing start sites). For example, a sequence, such as "CCG," can be more difficult to accurately sequence through. However, in some instances, the position of the read where the CCG sequence occurs can directly impact the ability of the chemistry to sequence through the read. Therefore, a tiling strategy can adjust the position of the CCG position in the read, which can allow for an increased chance that the chemistry will accurately read through the CCG sequence motif.

In some embodiments, the amplified regions can comprise target regions. The amplicons can be approximately 50, 60, 70, 80, 90, 100, 110, 120, 140, 150, 160, 170, 180, 190, 200, 210, 220, 230, 240, 250, 270, 290, 300, 320, 340, 360, 380, 400, 450, 500, 550, 600 or more nucleotides in length. In some embodiments, each amplicon is generally between approximately 100 nucleotides to approximately 200 nucleotides.

The tiled amplicons can comprise nucleotides that overlap one another. The overlap can be approximately 1, 2, 3, 4, 5, 6, 7, 8, 9, 10, 11, 12, 13, 14, 15, 16, 17, 18, 19, 20, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110 120, 130, 140, 150, 160, 170, 180, 190, 200, 225, 250, 275, 300 or more nucleotides.

Primers can be designed such that they are optimized. Some non limiting examples of ways to optimize primers are by: variation in length or sequence to account for an optimal Tm; based on their specificity to the target hybridization location; to avoid dimerization with one another and/or to avoid common polymorphisms. In some embodiments, primers can be designed to avoid areas with common known polymorphisms, i.e. where the minor allele frequency is more than 1%, 2%, 3%, 4%, 5%, 6%, 7%, 8%, 9%, 10% or more. Primers can comprise a 3'OH group that can be extended by a polymerase.

The primers can be labeled by using nucleotides. The primers can be labeled at the 3' end, the 5' end, and/or in the middle. The primers can comprise labeled nucleotides (e.g. nucleotides conjugated to biotin or fluorescent moieties). Methods for labeling nucleotides have been described herein. The primers can comprise a 5' nucleotide tail label. The primers can comprise a nucleotide tail and/or a labeled nucleotide. The 5' nucleotide tail can comprise a known sequence. The known sequence added in the 5' nucleotide tail can make the amplicon useful for downstream reactions. The known sequence can comprise an adapter, a molecular barcode, and/or or other known sequence.

An adapter or sequencing adapter or adapter sequence can comprise a sequence that corresponds to an adaptor for the sequencing platform used in the reaction. An adapter, for example, can be added to or near the 5' end. In some embodiments, the 5' adapter is referred to as an A adapter. Adapter sequences are described further herein. The molecular barcode can correspond to the sample source, the direction of the elongation, and/or the target region.

The primer can be hybridized to a nucleic acid and elongation can occur. A strand displacing thermostable polymerase can be used to extend. A copy of the template nucleic acid can be generated by polymerase during elongation. The polymerase can also serve to displace any nucleic acid(s) that are hybridized to the template. The process of amplicon generation can repeated or cycled. The amplicon generation process can comprise: heat denaturation, primer annealing, and primer extension.

The primers can be designed such that only the forward strand of the template is copied. In other embodiments, the primers can be designed such that only the reverse strand of the template is copied. In other embodiments, the primers can be designed such that both the forward and reverse strand of the template are both copied. The primers can comprise a molecular barcode that comprises two or more nucleotides that can be associated with information about the orientation or template strand being copied.

Forward and reverse reactions can be performed together. Forward and reverse reactions can be performed separately. When forward and reverse reactions are performed separately, they can be combined in later steps. The amplicons generated from the separate forward and reverse reactions can be mixed before library generation. The libraries created from separate forward and reverse reactions can be pooled prior to sequencing. The forward and reverse reactions can be sequenced separately and the data can be combined in silico.

The forward and reverse strand amplicons can be used for error correction. The forward and reverse strand amplicons can be used for refining mapping. The forward and reverse strand amplicons can be used for distance analysis.

The amplified products or amplicons can be size-processed in such a matter as to reduce or control the total length. In some instances, the size-processing can be fragmentation, in other instances, the size-processing can be to halt elongation. The size-processing can result in amplicons that are of a size that can be optimal for sequencing. Size-processing of the amplicons may occur by any enzymatic or physical means known in the art.

Enzymatic fragmentation can occur by using enzymes that can cut (e.g. hydrolyze) nucleic acid bonds. Some non limiting examples of enzymes that can cut nucleic acids include: hydrolases, nucleases, ribonucleases, deoxyribonucleases, phosphoesterases, topoisomerases, endonucleases, restriction enzymes, type II restriction endonucleases, or type I restriction nucleases.

In some instances, nucleic acid fragmentation can occur by physical or mechanical force. Some non limiting methods of physically fragmenting nucleic acids can include: sonification, nebulization, or hydroshearing.

The size-processing of the amplicons can also occur at the 3' end during elongation. In some instances, the size-processing accomplished by generating random 3' ends. 3' size-processing can occur by using nucleotides that lack a 3' OH group, biotin-ddNTPs, dUTP followed by UDG/APE1, methyl C, or other modified nucleotides. Incorporation of such nucleotides can halt or terminate elongation. The frequency of incorporation of such nucleotides can be altered by titrating the amount of such nucleotides. In some embodiments, amplicons terminated using a biotinylated ddNTP, can be further isolated by using streptavidin bead purification.

Nucleotides can be added to the 3' end of the amplicon; this can be called a 3' nucleotide tail. The 3' nucleotide tail can comprise a known sequence. The known sequence can make the amplicon useful for downstream reactions. The 3' nucleotide tail can comprise an adapter, a molecular barcode, and/or a known sequence for amplification. The adapter can comprise a sequence that corresponds to an adaptor that can be used with a sequencing platform. In some embodiments, this 3' adapter can be referred to as an B-adapter. The molecular barcode can correspond to the sample source, the direction of the elongation, and/or the target region. The second known sequence can comprise known nucleic acids. The methods used to add a 3' nucleotide tail can vary based on the method(s) used for size processing. In some cases the 3' tail can be an extension of further nucleotides, differentiating one copy and 5' labeled molecule from another copy and 5' labeled molecule.

In the presence of a 3' OH (e.g. if enzymatic or physical fragmentation is used as a method of size-processing), the 3' nucleotide tail can be added by ligation or by an additional primer extension step. The 3' nucleotide tail can be added through ligation, the steps comprising: end repair and ligation of double stranded construct with a random overhang. The 3' nucleotide tail can be added through primer extension and elongation on the single stranded template.

If a terminating nucleotide is used for size-processing, the 3' end of the molecule may not be available for primer extension or ligation due to the lack of a 3' OH. In the absence of a 3' OH, a 3' nucleotide tail can be added by hybridizing a primer comprising a random nucleotide sequence on the 3' end and a complementary sequence to the 3' nucleotide tail on the 5' end (e.g. 5'-known sequence-random sequence . . . -3'). The random sequence of the primer can hybridize to the amplicon. The random sequence can be comprised of 1, 2, 3, 4, 5, 6, 7, 8, 9, 10, 11, 12, 13, 14, 15, 16, 17, 18, 19, 20, or more nucleotides. A mixture of primers that comprise a random sequence can comprise a mixture of all possible sequences. In one non limiting example, if the random sequence comprises 5 nulceotides than there can be $4^5$ or 1,024 possible combinations of A, T, C, and G bases. In another non limiting example, if the random sequence comprises 6 nucleotides, than there can be $4^6$ or 4,096 combinations of A, T, C, and G bases and the primer mix can comprise a mixture of all or essentially all of the possible combinations.

In some embodiments, the amplicon has been purified or captured through incorporation of a biotin-ddNTP binding to streptavidin. A strand displacing polymerase can be used to extend 5-3'. The random sequence at the end of the biotinylated template can extend and displace all other randomly associated primers, thereby becoming the only extended nucleic acid on the template amplicon. In one non-limiting example, the complex can comprise: a 5' A adapter-locus specific primer-target-terminating ddNTP-biotin 3'; the reverse strand can comprise: 5'-B adapter-random sequence-target-locus specific sequence-A adapter-3'. The complex can be double stranded. The complex can be further isolated by washing the streptavidin beads and removing the supernatant. One strand of the complex can be released from the strepavidin beads by heat denaturation and the other strand can remain covalently bound to the straptavidin through the biotin moiety.

The processed amplicon can be amplified through linear amplification or PCR. To amplify the nucleic acid, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more cycles of PCR can be performed with primers that are complementary to the A and B adapter sequences. In an exemplary embodiment, approximately 9 to approximately 12 cycles of PCR are performed.

The amplification step can incorporate more known nucleotides at the 5' and 3' ends (e.g. by using PCR primers that contain known sequences at the 5' end). The molecular barcodes can be added during this step. In some embodiments, the known nucleotide sequences at the 5' and/or 3' end may not comprise the full length sequencing adaptors that can be necessary for a next generation sequencing reaction. In these instances, full length sequencing adapters can be incorporated during the PCR step. In some cases such as ILMN sequnceing the most 3' ends of the adapter sequences may be identical. In some cases an extra base or a few extra bases may need to be added to insure directionality of A and B adapter sequences on the same strand of the library molecule.

In an exemplary embodiment, the resulting sequencer ready library can consist of double stranded molecules in the following format: 5'-A adapter-synthetic primer-amplicon-B adapter-3'. In some embodiments, the resulting sequencer ready library can comprise 1, 2, or 3, or more molecular bar codes. The A adaptor and B adapter can correspond to adapter sequences that are used with the sequencing platform; adapter sequences are discussed herein. Any method of sequencing can be used to analyze the sequencer ready library; a summary of sequencing methods can be found herein. The data resulting from such a sequencing reaction can be stored, transmitted and/or analyzed by any method known in the art; methods of data storage and transmittal can be found herein.

Sequencing reads can be analyzed through data analysis. The data can be analyzed using software. Software can trim adaptors off of the reads. The sample can be identified if optional molecular barcodes were incorporated. Duplicate reads can be removed. The genomic coordinate of the read can be identified by the known synthetic sequence at the beginning of the read. Reads corresponding to the same known genomic coordinate can be binned together and a consensus sequence can be generated. The consensus sequence can be generated without the use of a reference genome. Consensus sequences can be compared to a reference genome. Reads that do not form a consensus can be removed from analysis. Each contiguous segment of target nucleic acid can be considered a singular 'target' and all primers corresponding to that target are considered that targets primer set. This can produce an in silico read length equivalent to the full length of the target, regardless of target size.

After a consensus sequence is determined, known haplotypes for the target region can be queried. A haplotype can be a member of a polymorphic set. Haplotype data can be information concerning the haplotype of a sample. Match haplotypes that are known to either cause disease or not can be identified. For consensus sequences that do not match a known haplotype, the de novo sequence can be used to determine novel haplotypes, haplogroups and/or structural variation.

Advantages of targeted sequencing can include data analysis that may not require alignment of each read to a reference genome (i.e. the synthetic sequence at the beginning of each read may identify the genomic position and the remainder of the read can be de novo or reference free). Sequencing variants can be more reliably distinguished from genomic variants. For example, several amplicons that cover the same genomic region having a variant sequence can indicate that the variant is genomic. Primer sets can be binned for each contiguous target, allowing for assembly. Complex variation can be detected. Random 3' end of reads can avoid clonal errors (i.e. can show different templates with low frequency variation such as somatic mutations). Other advantages of the targeted sequencing method include: ddNTP termination can provide random fragmentation that can involve less clean-up. Synthetic sequences in the chimeric library molecule may be used for identification or sample and genomic coordinate. In some cases, they may be removed from the read and assembly analysis such that only sample derived sequences is used for assisted de novo assembly. Random 3' ends of reads can ensure that the sequenced molecule is not "clonal", thereby possibly providing a dramatic reduction in errors and allowing greater sensitivity to detect somatic variation. Duplicate reads can be removed in silico, whereas traditional PCR-based targeted sequencing does not allow for removal of duplicates. Tiling probe design can allow for redundant sampling and consensus read lengths. This can avoid target drop out because of SNPs or novel biology under one primer site. The incorporation of biotin during primer extension can simplify clean up. Random priming of isolated molecules can allow incorporation of B-adaptors without ligation or additional clean up or end repair. Synthetic sequences at the beginning of each read can allow for dramatically reduced computational burden by avoiding reference genome mapping. Long consensus reads can allow for detection of complex variation. Linear consumption of target specific synthetic primers can reduce cost per sample and increases volume per production lot.

B. Highly Multiplexed PCR

Targeted sequencing methods can comprise highly multiplexed PCR with or without biotin. A target region can be isolated from a genomic DNA sample. Target regions can comprise a plurality of target genes. Target genes have been disclosed herein. Target regions can be isolated using biotinylated capture of PCR products. The PCR products size can range from 10-1000, 100-10,000, 100-20,000, 1,000-20,000, 2,000-15,000, 10,000-15,000, 10,000-20,000, 10,000-100, 000, or 10 and 200,000 nucleotides in length.

Primers can be designed to flank the one or more areas of interest (i.e. target regions or target loci). The one or more areas of interest can be genes. Primers can hybridize to the target sequence. An amplification reaction can be performed. The amplification reaction can be PCR. The PCR can be long range PCR. The amplification reaction can be highly multiplexed. The amplification reaction can be low copy or low cycle. The PCR of one or more loci can be multiplexed. The PCR can be highly multiplexed PCR. Highly multiplexed can me that more than 10, 20, 30, 40, 50, 60, 70, 80, 90, 100, 120, 140, 160, 180, 200, 250, 300, 400, 500, 600, 700, 800, 900, 1000, 1500, 2000, 3000, 4000, 5000, 6000, 7000, 8000, 9000 or more target loci. The amplification of a loci can be performed independently. The one or more amplification products can be pooled.

Biotin-conjugated dNTPs can be incorporated. Biotin-conjugated dNTPs can be incorporated during amplification. Amplification can occur with a dNTP mixture that comprises approximately 0.1%, 1%, 2%, 3%, 4%, 5%, 6%, 7%, 8%, 9%, 10%, 12%, 15%, 20%, 25% or more biotin conjugated dNTPs. In some embodiments the biotin conjugated dNTP can be dUTP.

The PCR amplified product can be run on a gel. The gel can be an agarose gel. The gel can be a low-melt agarose gel. A marker ladder can be loaded into an adjacent well. The portion of the gel that contains PCR product can be excised. In some embodiments, the portion to be excised will be guided by the length expected from primer design. In some embodiments, the gel portion corresponding to PCR product in the 10-15K range is the gel portion to be excised.

The amplification product can be purified from the agarose. The gel-excised agarose can be dissolved. The gel-excised agarose can be dissolved in dissolving buffer. The purified or semi-purified polynucleotide can be further isolated. The polynucleotide can be bound to a column. The column can be a genomic DNA binding column. The column can be washed. The polynucleotide can be eluted from the column. The eluted polynucleotide can be fragmented. Methods of fragmentation have been disclosed herein. The polynucleotide can be fragmented in to fragment ranges that range from approximately 50-1000, 100-1000, 150-700, 200-660, 100-800, or 10-1500 nucleotides.

Target amplification product can be separated. Target amplification product can be separated based on size selection. Target amplification product can be separated based on size via gel electrophoresis/gel purification, size exclusion columns/column clean-up, and/or solid phase reversible immobilization (SPIR) beads optimized for size selection.

Target purification can be separated by affinity purification (e.g. with streptavidin if biotin dNTPs have been incorporated). The polynucleotide comprising biotin can be exposed to streptavidin. The polynucleotide can be exposed to streptavidin before or after it has been fragmented. The streptavidin can comprise straptavidn-coated beads. The streptavidin-biotin-fragment complex can be purified or semi-purified. The streptavidin-biotin-fragment complex can be washed.

The polynucleotide fragments can be treated. Methods of polynucleotide treatment are disclosed herein. The polynucleotide fragments can be end-repaired. Methods of end-repair are disclosed herein. The polynucleotide fragments can be adapter tailed. Methods of adapter tailing are disclosed herein. The polynucleotide fragments can be amplified. Methods of amplification are disclosed herein. The polynucleotide fragments can be amplified in the presence of straptavidin.

Amplified product can be sequencer-ready and may comprise a sequence library. Amplified product may be further processed. Methods of polynucleotide processing are disclosed herein. Amplified product may be run on an agarose gel. Amplified product may be gel excised and purified before sequencing.

Methods of sequencing a sequence library are disclosed herein. Data can be produced from sequencing a library. Methods for storing and transmitting data that has been produced from a sequencing reaction are disclosed herein.

The data can be analyzed or processed. Methods for analyzing or processing of data have been disclosed herein. The analyzed data can be used. Methods of using analyzed sequencing data have been disclosed herein.

C. Targeted Elongation and Ligation Adapter (TELA)

Figure 10:
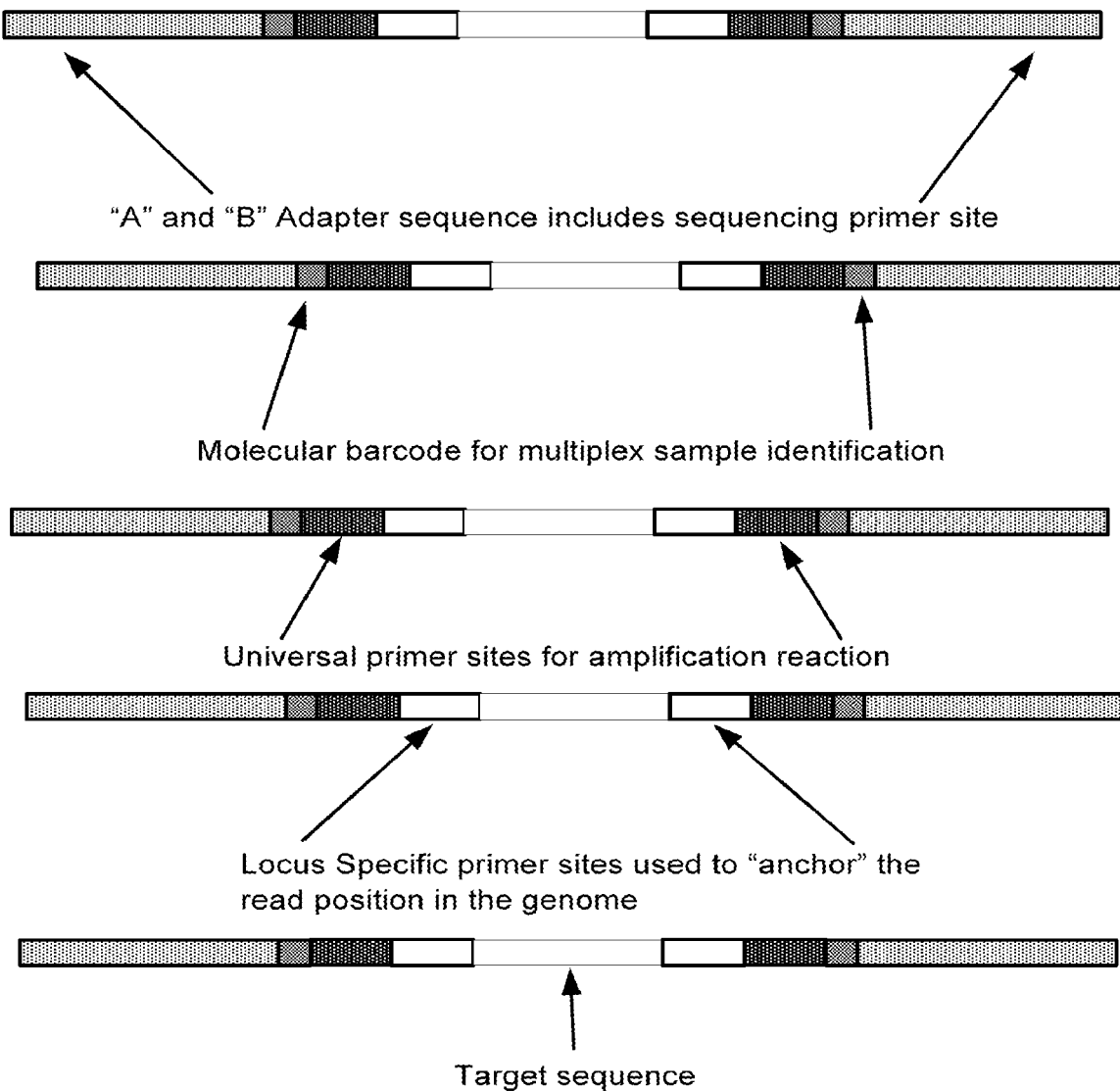
FIG. 10 depicts multiple adapter sequences, barcodes and primer sites within a mPEAR, TELA, RAPEL or other products of the methods and compositions of this disclosure.

Target molecules may be tagged or barcoded with alternative methods, herein referred to as TELA. The TELA methods, as shown in FIG. 10 generally provide for attachment of barcodes in a multi step process involving hybridization of primers comprising: locus specific sequences; universal adapter sequences, and barcode sequences. Primers with this configuration are herein referred to as TELA primers. Primer extension is then performed followed by ligation of products to form a contiguous sequence. In another embodiment, universal adapter sequences, contiguous with barcode sequences may be hybridized to polynucleotide sequences containing other universal adapter sequences and amplified together. In other cases, universal adapter sequences, contiguous with bar code sequences, may be hybridized to polynucleotide sequences containing other adapter sequences which may be suitable for high throughput sequencing platforms or other applications, such as ligation of a locus specific primer of a random tailed primer.

D. Design and Annealing of TELA Primers

Figure 6:
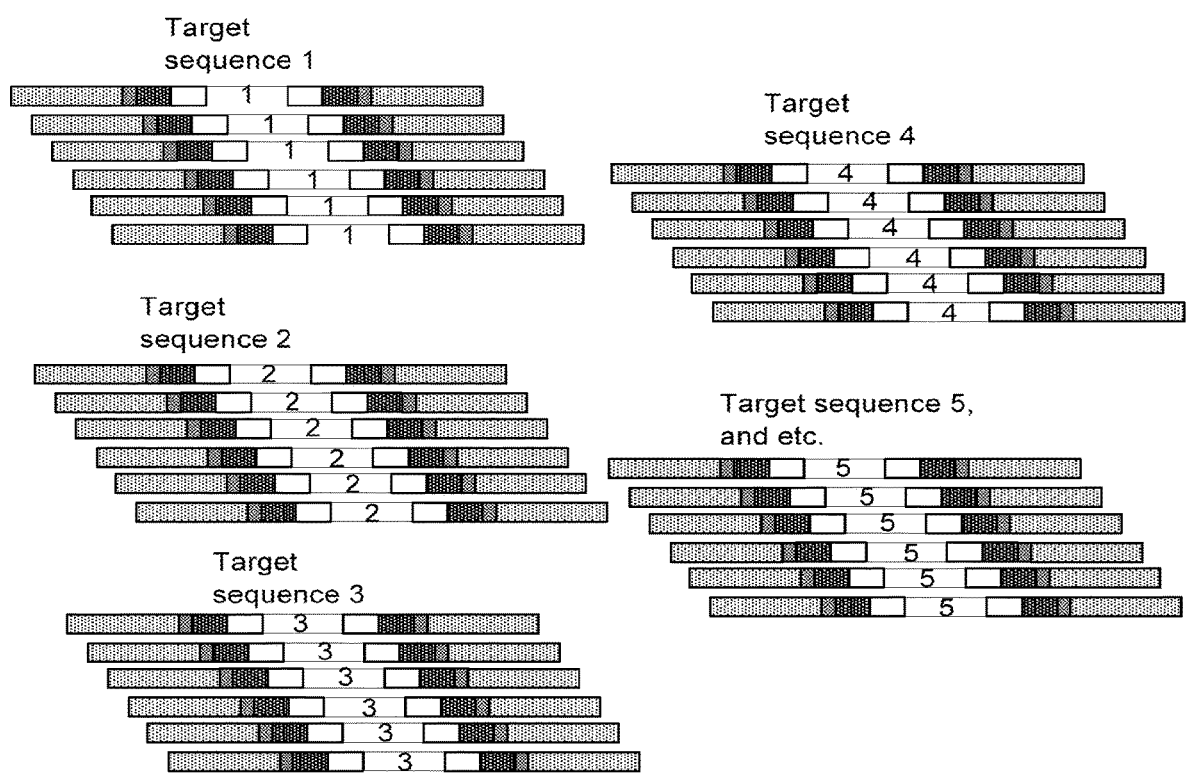
FIG. 6 depicts multiple target sequences flanked by adapter sequences and molecular labels or bar codes.
Figure 7:
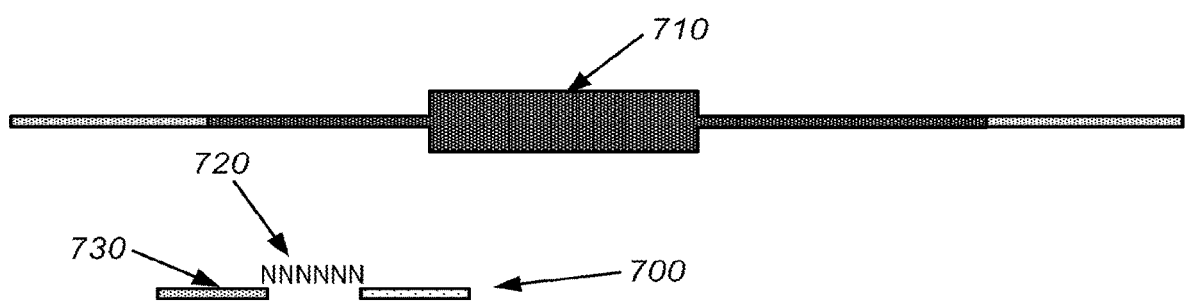
FIG. 7 depicts a mPEAR or TELA primer and a target sequence.
Figure 8:
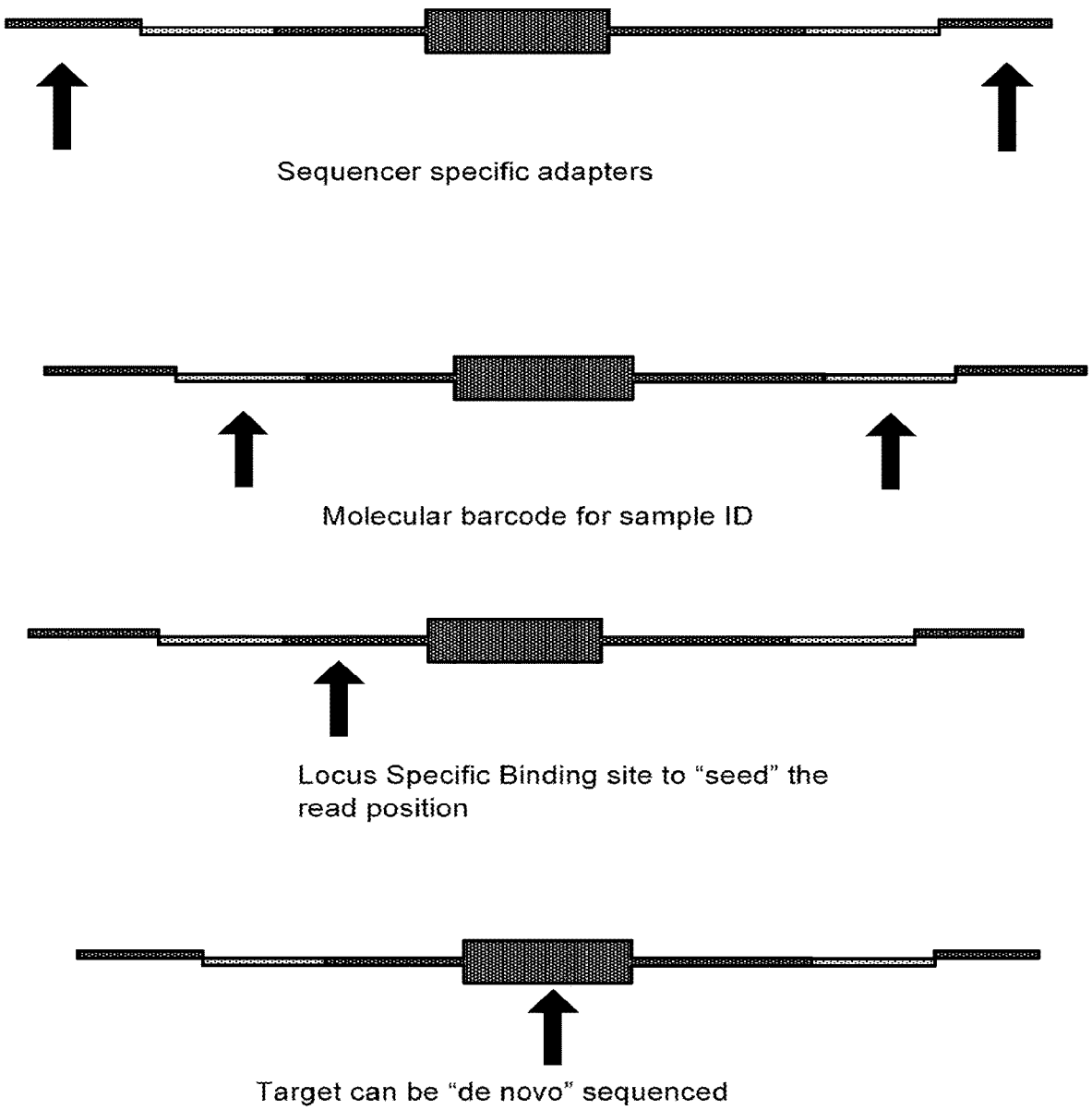
FIG. 8 depicts the attachment of adapater sequences and barcodes for de novo sequencing of a target sequence.

In some embodiments, target polynucleotides are first hybridized to TELA primers formed from locus specific sequences, or second and third probe domains, (which may be of known, partially known or unknown sequence) and universal adapter sequences and barcodes, or first and $4^{th}$ probe domains. Hybridization of TELA primers to target molecules form primer-target constructs which are then used to carry out an initial primer extension reaction in which extension products complementary to the template strand of each individual adaptor-target construct are formed as shown in FIG. 7. The resulting primer extension products are then ligated and may be amplified to collectively provide a library of tagged or barcoded template polynucleotides as shown in FIG. 6. The term library refers to the collection of target fragments containing known common sequences at their 3' and 5' ends, and may also be referred to as a 3' and 5' modified library. In some cases, a locus specific primer and a random primer may be used in a similar strategy, whereby either a forward or reverse locus specific primer is used in combination with a corresponding (i.e forward/reverse) random primer. In some cases, the use of a combination of locus specific primer and random primer may generate overlapped amplicons. In some cases, this may generate longer target lengths for sequencing.

In some cases, universal adapter sequences for all samples or one or both strands of the duplexes may carry the tag sequence to barcode or track the identity of the samples. In some cases, a barcode is not included.

An important feature of the TELA primer sequence, as shown in FIG. 7 is that a portion of the sequence may not fully anneal to the target sequence, 710. Generally, this portion of the sequence comprises a separate primer site, 730, which is contiguous with sequence that is complementary to a locus of interest, 700. TELA sequences are generally formed by the annealing of two partially complementary polynucleotide strands so as to provide, when the two strands are annealed, at least one double-stranded region and at least one non-complementary single-stranded region. In some cases, the locus specific region may be linked to a random spacer sequence, 720. In some cases, spacer sequences may be less than 20, 30, 40 50, 60, 70, 80, 90, 100, 200, 300, 400, 500, 600, 700 800, 900 or 1000 nucleotides in length. In other cases, spacer sequences may be greater than 20, 30, 40 50, 60, 70, 80, 90, 100, 200, 300, 400, 500, 600, 700 800, 900 or 1000 nucleotides in length.

In general the double stranded region of the adapter comprises one or more consecutive nucleotides, formed by annealing of the two partially complementary polynucleotide strands, generally between complementary sequences of locus specific sequence. Double stranded, as provided herein generally refers to two strands that have annealed and does not refer to any particular structural DNA feature. Additionally, the double stranded region may also refer to the locus specific sequence, as the sequence is complementary to a sequence in the target polynucleotide.

Generally, the locus specific region of TELA primers, as in mPEAR primers, may be designed to be as short as possible without loss of function. In this context, 'function' refers to the ability of the double-stranded region to form a stable duplex under standard reaction conditions for an enzyme-catalyzed nucleic acid ligation reaction, (e.g. incubation at a temperature in the range of 4° C. to 60° C. in a primer extension buffer appropriate for the enzyme), such that the two strands forming an adaptor remain partially annealed during extension of the primer on the target molecule.

Identical adaptors are ligated to both ends of each target polynucleotide. The target sequence in each adaptor-target construct will be flanked by complementary sequences derived from the double-stranded region of the primers. The longer the double-stranded region, and hence the complementary sequences derived therefrom in the adaptor-target constructs, the greater the possibility that the TELA primer-target construct is able to fold back and base-pair to itself in these regions of internal self-complementarity under the annealing conditions used in primer extension and/or PCR. It is, therefore, generally the double-stranded region can be less than 100, 90, 80, 70, 60, 50, 40 30, 20, 10 nucleotides in length. In some instances, the double-stranded region may be greater than 100, 90, 80, 70, 60, 50, 40 30, 20, 10 nucleotides in length in order to reduce this effect. The stability of the double-stranded region may be increased, and hence its length potentially reduced, by the inclusion of non-natural nucleotides which exhibit stronger base-pairing than standard Watson-Crick base pairs.

The TELA primer may vary in the percentage of complementarity in the locus specific sequence. In some cases it may be 100% complementary in the double-stranded region. In other cases it may greater than 1%, 10%, 20%, 30%, 40%, 50%, 60%, 70%, 80%, 90% complementary. In other cases it may be less than 1%, 10%, 20%, 30%, 40%, 50%, 60%, 70%, 80%, 90% complementary. One or more nucleotide mismatches may be tolerated within the double-stranded region, provided that the two strands are capable of forming a stable duplex under standard ligation conditions.

Sequences of universal adaptors for use in the methods may generally include a double-stranded region forming the 'ligatable end of the adaptor, i.e. the end that is joined to a target polynucleotide in the ligation reaction. The ligatable end of the adaptor may be blunt or, in other embodiments, short 5' or 3' overhangs of one or more nucleotides may be present to facilitate/promote ligation. The 5' terminal nucleotide at the ligatable end of the adaptor is phosphorylated to enable phosphodiester linkage to a 3' hydroxyl group on the target polynucleotide.

Another feature can include a region of a universal adapter sequence where the two polynucleotide strands forming the adaptor exhibit a degree of non-complementarity such that the two strands are not capable of fully annealing to each other under standard annealing conditions for a primer extension or PCR reaction. In some instances, this region may undergo annealing under standard reaction conditions for an enzyme-catalyzed ligation reaction, provided that the two strands revert to single stranded form under annealing conditions in an amplification reaction.

Generally, regions may be designed to prevent annealing in a variety of ways as described herein.

In terms of length, regions that may not anneal may be determined by function, for example, the need to provide a suitable sequence for binding of a primer for primer extension, PCR and/or sequencing. Generally, the length of such a region may extend for any number of nucleotides. In many cases it is preferred to minimize the overall length of the adaptor, for example, in order to facilitate separation of unbound adaptors from adaptor-target constructs following the ligation step. Therefore, it is generally preferred that the unannealed regions should be less than 20, 30, 40 50, 60, 70, 80, 90, 100, 200, 300, 400, 500, 600, 700 800, 900 or 1000 nucleotides in length. In other cases, unannealed regions should be greater than 20, 30, 40 50, 60, 70, 80, 90, 100, 200, 300, 400, 500, 600, 700 800, 900 or 1000 nucleotides in length. In some cases non complementary regions may destabilize the 5' end of the primer. In some cases, minimizing the length of this primer may also minimize the chance that the tail sequence coud partially bind to another region of the template DNA.

The actual nucleotide sequence of the TELA primers may be any sequence and length suitable. TELA primers may be selected by the user such that the desired sequence elements are ultimately included in the common sequences of the library of templates derived from the adaptors to, for example, provide binding sites for particular sets of universal amplification primers and/or sequencing primers. Additional sequence elements may be included, for example, to provide binding sites for sequencing primers which will ultimately be used in sequencing of template molecules in the library, or products derived from amplification of the template library, for example on a solid support in sequencing applications.

TELA primer sequences may comprise two strands of DNA, but may also include any nucleotides or nucleotide derivatives that may be suitable. Alternative nucleotides may include mixtures of natural and non-natural nucleotides (e.g. one or more ribonucleotides) linked by a mixture of phosphodiester and non-phosphodiester backbone linkages. Other non-nucleotide modifications may be included such as, for example, biotin moieties, blocking groups and capture moieties for attachment, such as biotinylated nucleotides.

Further adapter sequences may also comprise exonuclease resistant modifications such as phosphorothioate linkages. Such modifications reduce the number of adaptor-dimers present in the library, since the two adaptors cannot undergo ligation without removal of their non complementary overhangs. The adaptors can be treated with an exonuclease enzyme prior to the ligation reaction with the target, to ensure that the overhanging ends of the strands cannot be removed during the ligation process. Treatment of the adaptors in this manner reduces the formation of the adaptor-dimers at the ligation step.

E. Primer Extension and Ligation

After annealing TELA primers, a primer extension reaction may be performed using any suitable polymerase as described herein (see Section II-F). Further, one or more products may be ligated together to form a contiguous sequence using ligations methods as described herein.

Additionally, one or more contiguous primer extension-ligation products may be further assembled into longer fragments for downstream analysis as shown in FIG. 6. In some cases, universal adapter sites in the primers may be used as hybridization sites to anneal one or more products together. Using PCR or further primer-extension reactions, multiple products may be assembled into longer contiguous strands.

The combined ligated polynucleotide sequences and unligated adaptor polynucleotide constructs may be purified from any components of the ligation reaction, such as enzymes, buffers, salts and the like. Suitable purification methods are known in the art and utilize standard methods (Sambrook and Russell, Molecular Cloning, A Laboratory Manual, third edition).

Additionally, after ligation of the first primer extension product, adapters may be attached to the flanking regions of the ligation product. Adapter primers, comprising an adapter region and a universal priming region, complementary or partially complementary to universal adapter sites in the ligation product may be used to generated polynucleotides with attached adapters. The general protocol for using TELA primers (i.e hybridization followed by primer extension and ligation), and general design of TELA primers may apply to use of adapter primers.

In some cases, adapter sequences may be useful for downstream applications such as sequencing as described herein.

F. Amplification Techniques

Numerous amplification methods and techniques are known in the art. Any suitable methods may be used in the methods of this disclosure, so as to increase the quantity or amount of polynucleotides, while maintaining the initial content of sequence information of the original sample or ligation product. One or more amplification methods may be used and in one or more combinations.

Examples of amplification methods may include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al., Nucleic Acids Res. 20(7): 1691-6 (1992), and rolling circle amplification, described in U.S. Pat. No. 5,648,245. Other amplification methods that may be used are described in, U.S. Pat. Nos. 5,242,794, 5,494,810, 4,988,617 and in U.S. Ser. No. 09/854,317 and US Pub. No. 20030143599, each of which is incorporated herein by reference. In some aspects DNA is amplified by multiplex locus-specific PCR. In a preferred aspect the DNA is amplified using adaptor-ligation and single primer PCR. Other available methods of amplification, such as balanced PCR (Makrigiorgos, et al., Nature Biotech, 20:936-9 (2002)) and isothermal amplification methods such as nucleic acid sequence based amplification (NASBA) and self-sustained sequence replication (Guatelli et al., PNAS USA 87:1874 (1990)). Based on such methodologies, a person skilled in the art readily can design primers in any suitable regions to be amplified.

G. Amplification Products and Conditions

In general, any suitable amplification products and conditions to produce products may be used in the methods of this disclosure. Various amplification lengths, cycle times, hybridization, annealing and extension conditions may be used, as appropriate for various amplification techniques and sequences.

i. Amplification Lengths

Generally, the length of an amplified product may be any length and contain any sequence that may be useful in the enumeration of sequences. Generally, an amplified polynucleotide may be at least about 5 bp, 10 bp, 20 bp, 30 bp, 40 bp, 50 bp, 60 bp, 70 bp, 80 bp, 90 bp, 100 bp, 200 bp bp, 300 bp, 400 bp, 500 bp, 600 bp, 700 bp, 800 bp, 900 bp, 1 kb, 2 kb, 3, kb, 4 kb, 5 kb, 6 kb, 7 kb, 8 kb, 9 kb, 10 kb, 20 kb, 30 kb, 40 kb, 50 kb, 75 kb, or 100 kb. Generally, an amplified polynucleotide may be at most about 5 bp, 10 bp, 20 bp, 30 bp, 40 bp, 50 bp, 60 bp, 70 bp, 80 bp, 90 bp, 100 bp, 200 bp bp, 300 bp, 400 bp, 500 bp, 600 bp, 700 bp, 800 bp, 900 bp, 1 kb, 2 kb, 3, kb, 4 kb, 5 kb, 6 kb, 7 kb, 8 kb, 9 kb, 10 kb, 20 kb, 30 kb, 40 kb, 50 kb, 75 kb, or 100 kb.

ii. Amplification Conditions

In general any suitable amplification conditions may be used, for either selective or universal amplification. In some cases, amplification may be linear. In some cases, amplification may be logarithmic. Since the methods of the disclosure provide for enumeration of one or more sequences, which may be amplified, it may be suitable to control amplification in various steps to control variability between samples.

For example, in some cases, a limited number of amplification cycles may be used in either a selective or universal amplification step. This may be particularly suitable for selective amplification wherein different primer sets for different loci or barcodes may behave differently under multiplex conditions wherein a plurality of loci or barcodes are used. Primers in different primer sets may differ in their ability to hybridize to template, and thus yield differences in amplification efficiency between primer sets. Each set of primers for a given locus may behave differently based on sequence context of the primer and sample DNA, buffer conditions, and other conditions. A universal DNA amplification for a multiplexed assay system may generally introduce less bias and variability.

To minimize amplification variation between one or more loci or barcodes, for example, amplification may be performed using a linear amplification method, followed by logarithmic universal amplification. In some cases, the number of cycles is limited between 1-50 cycles, such that amplification is linear or near linear. In some cases amplification cycles for linear amplification may be at least about 1, 2, 3, 4, 5, 6, 7, 8, 9, 10, 20, 30, 40 or 50 cycles. In some cases amplification cycles for linear amplification may be at most about 1, 2, 3, 4, 5, 6, 7, 8, 9, 10, 20, 30, 40 or 50 cycles. In some cases, after linear selective amplification of sequences from ligation products, a logarithmic universal amplification step may be performed as described herein. Universal amplification, wherein common primer sets may be used for a plurality of loci or barcode amplification products may further reduce amplification variability, while producing increasing amounts of sample.

In other cases, logarithmic amplification may be used before linear amplification. In some cases amplification cycles for logarithmic amplification may be at least about 1, 2, 3, 4, 5, 6, 7, 8, 9, 10, 20, 30, 40 or 50 cycles. In some cases amplification cycles for logarithmic amplification may be at most about 1, 2, 3, 4, 5, 6, 7, 8, 9, 10, 20, 30, 40 or 50 cycles.

Generally, any suitable number of primer sets may be used for amplification. In some cases, amplification primer sets may be about equal to the number of loci tested. In some cases, primers sets may be at least about 1, 2, 3, 4, 5, 6, 7, 8, 9, 10, 20, 30, 40, 50, 60, 70, 80, 90 100, 125, 150, 175, 200, 300, 400, 500, 600, 700 800, 900 or 1000 primer sets. In some cases, primers sets may be at most about 1, 2, 3, 4, 5, 6, 7, 8, 9, 10, 20, 30, 40, 50, 60, 70, 80, 90 100, 125, 150, 175, 200, 300, 400, 500, 600, 700 800, 900 or 1000 primer sets.

IV. SEQUENCING METHODS

Numerous methods of sequence determination are compatible with the systems and methods of the disclosures. Exemplary methods for sequence determination include, but are not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459,311 and 6,210,891; Balasubramanian, U.S. Pat. Nos. 7,232,656 and 6,833,246; Quake, U.S. Pat. No. 6,911,345; Li et al, Proc. Natl. Acad. Sci., 100: 414-419 (2003); pyrophosphate sequencing as described in Ronaghi et al., U.S. Pat. Nos. 7,648,824, 7,459,311, 6,828,100, and 6,210,891; and ligation-based sequencing determination methods, e.g., Drmanac et al., U.S. Pat. Appl. No. 20100105052, and Church et al, U.S. Pat. Appln Nos. 20070207482 and 20090018024.

Sequence information may be determined using methods that determine many (typically thousands to billions) nucleic acid sequences in an intrinsically parallel manner, where many sequences are read out preferably in parallel using a high throughput serial process. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeg™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

V. KITS

Kits may be used in preparing libraries of tagged polynucleotides using the method using either mPEAR, Rappel, targeted Rappel or TELA methods.

A kit may comprise at least a supply of mPEAR, TELA primers, universal adapters or a combination thereof, as defined herein, plus a supply of at least one amplification primer which is capable of annealing to the adaptor primer and priming synthesis of an extension product, which extension product would include any target sequence ligated to the adaptor when the adaptor is in use.

In some cases, features of the adaptor sequence for inclusion in the kit are as described elsewhere herein in relation to other aspects of the invention. The structure and properties of amplification primers are well known to those skilled in the art. Suitable primers of appropriate nucleotide sequence for use with the adaptors included in the kit can be readily prepared using standard automated nucleic acid synthesis equipment and reagents in routine use in the art. The kit may include a supply of one single type of primer or separate supplies (or even a mixture) of two different primers, for example a pair of amplification primers suitable for PCR or isothermal amplification of templates modified with the adaptor sequences in solution phase and/or on a suitable solid support (i.e. solid-phase amplification). The kit may comprise a double stranded adapter for ligation to a sample of interest, plus at least two different amplification primers that carry a different tag sequence, where the tag sequence does not hybridize to the adapter. This kit can be used to amplify at least two different samples where each sample is amplified using a single tagged primer, and then pooled after the individual amplification reactions.

Adaptors and/or primers may be supplied in the kits ready for use, or more preferably as concentrates requiring dilution before use, or even in a lyophilized or dried form requiring reconstitution prior to use. If required, the kits may further include a supply of a suitable diluent for dilution or reconstitution of the primers. Optionally, the kits may further comprise supplies of reagents, buffers, enzymes, dNTPs, etc., for use in carrying out PCR or isothermal amplification. Suitable (but non-limiting) examples of such reagents are as described in the Materials and Methods sections of the accompanying Examples. Further components which may optionally be supplied in the kit include 'universal' sequencing primers suitable for sequencing templates prepared using the mismatched adaptors and primers.

D. Capture of Targeted Library Molecules Via Primer Extension (mPEAR)

mPEAR is a sample preparation technique that can be used for targeted sequencing. It can involve several steps as shown in FIG. 3.

i. Fragmentation

A polynucleotide sample may be first fragmented before subsequent steps. Fragmentation methods are described herein. The size of the polynucleotide fragments, described in terms of length, may vary depending on the source of the target polynucleotide, the method used for fragmentation, and the desired application. In some cases one or more fragmentation steps may be used. For example, 1, 2, 3, 4, 5, 6, 7, 8, 9, 10, 11, 12, 13, 14, 15, or more fragmentation steps may be used.

ii. Polynucleotide Strand End Repair

Fragmentation of polynucleotides, such as through mechanical shearing or enzymatic digestion, can result in fragments with a heterogeneous mix of blunt and 3'- and 5'-overhanging ends. In some embodiments DNA fragments can be repaired or treated using methods or kits (i.e. Lucigen DNA terminator End Repair Kit) known in the art to generate ends that are designed for insertion, for example, into blunt sites of cloning vectors. Blunt ended fragment ends of the population of nucleic acids can be sequenced.

Further, in some cases, the blunt ended fragment may also be phosphorylated. The phosphate moiety can be introduced via enzymatic treatment, for example, using a kinase, (i.e. shrimp alkaline kinase). Blunt ended fragments may be dephosphorylated by using a phosphatase. Sticky ended fragments may be trimmed using a nuclease. Overhangs may be added to blunt ends by any method known in the art.

Polynucleotide sequences can be prepared with single overhanging nucleotides by, for example, activity of certain types of DNA polymerase such as Taq polymerase or Klenow exo minus polymerase which has a nontemplate-dependent terminal transferase activity that adds a single deoxynucleotide, for example, deoxyadenosine (A) to the 3' ends of polynucleotides. Such enzymes can be utilized to add a single nucleotide 'A' to the blunt ended 3' terminus of each strand of the target polynucleotide duplexes. Thus, an 'A' could be added to the 3' terminus of each end repaired duplex strand of the target polynucleotide duplex by reaction with Taq or Klenow exo minus polymerase, whilst the adaptor polynucleotide construct could be a T-construct with a compatible 'T' overhang present on the 3' terminus of each duplex region of the adaptor construct. This end modification also prevents self-ligation of both adapter and target such that there is a bias towards formation of the combined ligated adaptor-target sequences.

iii. Barcoding identifier sequences or molecular barcodes can be used, 360. These sequences provide for a characteristic marker of the source of particular target molecules that may be identified in downstream application such as sequencing. Often, the unique identifier is a bar-code oligonucleotide of known sequence that is used to tag the target molecules. mPEAR methods can comprise attaching oligonucleotide barcodes to nucleic acid target molecules through an enzymatic reaction such as a ligation reaction. For example, the ligase enzyme may covalently attach a DNA bar code to fragmented DNA.

Another exemplary method for adding a molecular barcode can comprise using oligonucleotide primers containing a bar code sequences for use in an amplification reactions (e.g., PCR, or linear amplification etc.).

Often, as described herein, an identifier may be an oligonucleotide barcode sequence that is contiguous with the first or second probe in a probe set. In some cases, however, different identifiers may be used. An identifier, as with barcode sequences, may be unique or non-unique. For example, in some cases, the unique identifier may be a hybridization probe. In one example, a hybridization probe may comprise an oligonucleotide sequence and an additional component such as fluorescent element (i.e. nanoparticle, nanoprobe, quantum dot, etc). In some cases, one or more fluorescent elements may be described as barcodes as well. For example, fluorescent elements of varying wavelengths or colors may be arrayed in unique or non unique patterns or sequences. In other cases, the identifier is a dye, in which case the attachment may comprise intercalation of the dye into the analyte molecule (such as intercalation into DNA or RNA) or binding to a probe labeled with the dye. In still other cases, the identifier may be a nucleic acid oligonucleotide, in which case the attachment to the polynucleotide sequences may comprise a ligation reaction between the oligonucleotide and the sequences or incorporation through PCR. In other cases, the reaction may comprise addition of a metal isotope, in which either the first or second probe is labeled with the isotope.

The unique identifiers (e.g., oligonucleotide barcodes, probes, etc.) may be attached to polynucleotide sequences in a variety of ways. Barcodes may comprise different lengths. In some cases they may comprise about 1, 2, 3, 4, 5, 6, 7, 8, 9, 10, 20, 50, 100, 500, or 1,000 nucleotides in length. In some cases, molecular barcodes may be less than about 1, 2, 3, 4, 5, 6, 7, 8, 9, 10, 20, 50, 100, 500, or 1000 nucleotides in length. In some cases, multiple barcodes may be attached to a polynucleotide. In some cases about 1, 2, 3, 4, 5, 6, 7, 8, 9, 10, 20, 50, 100, 500, or 1,000 barcodes may be attached to a single polynucleotide. In some cases, a polynucleotide may be attached with less than about 1, 2, 3, 4, 5, 6, 7, 8, 9, 10, 20, 50, 100, 500, or 1,000 barcodes.

iv. Attachment of Known Sequences

Known sequences can be attached to the ends of the fragmented polynucleotide sample. Known sequences can comprise a molecular barcode, an adaptor for sequencing, or any other sequence such as a universal primer sequence. A universal primer sequence can comprise, for example, a known sequence that primers can hybridize to, e.g. for a PCR amplification reaction. In some embodiments, a ligation reaction ligation can be used to covalently join a known sequence to a fragment. Ligation methods can utilize a ligase enzyme such as a DNA ligase to join the ends of the polynucleotide strands (e.g. the fragment and the known sequence) such that covalent linkages are formed. A 5'-phosphate moiety may facilitate ligation to the target 3'-OH. Joining can mean covalent linkage of polynucleotide strands which were not previously covalently linked. In some embodiments, joining can involve formation of a phosphodiester linkage between the two polynucleotide strands, but other means of covalent linkage (e.g. non-phosphodiester backbone linkages) may be used. The known sequences can incorporate a marker that can facilitate separation (e.g. biotinylated nucleotides or nucleotides that are attached to a moiety that can be separated by antibody purification methods).

The fragments with adjoined known sequences can be amplified and/or purified. Purification can be based on size of the polynucleotides. Purification can be based on separation techniques such as biotin/streptavidin or antibody-based separation techniques. Purification can mean that the polynucleotide is separated from one or more components of the ligation reaction, such as enzymes, buffers, salts and the like. Suitable purification methods are known in the art and utilize standard methods. The fragments with adjoined, known sequences can be amplified. Amplification can be accomplished by any means known in the art, including PCR and/or linear amplification. During the amplification step, primers may be used that have tails with known sequences which can add, for example, molecular bar codes and/or adaptor sequences.

In some cases, unique barcodes may be formed from the combination of various sequences. In some cases, non-unique barcodes may be linked with additional sequences such as probe sequences, portions of probe sequences or additional sequences linked to the probe to form a unique barcode sequence. For example, the formation of a unique sequence may be formed at the beginning (start) and end (stop) portions of the probe sequences when used, alone or in combination, with a non-unique bar code sequence. The combination of sequences (i.e. probe sequence and non-unique barcode sequence), may provide unique identifying sequences. For example, in some cases a barcode may be designed with a general structure, 5'XXXXYYYY, wherein X is a variable length region complementary to one sequence selected from sequences including but not limited to first and/or second probe/hybridization sequences, adapter sequences, universal priming sequences, or linker sequences. Y may be selected from a non-unique barcode sequence of variable length. In some cases, Y sequences may be common to all probe sets in a sample. In other cases, Y sequences may be unique one locus, or a plurality of loci, such as a whole chromosome, or loci associated with a particular disease or genotype. In some cases, the length, or number of nucleotides defined as either X or Y may be about 1-20, 20-50, 50-75, 75-100, 100-150, 150-200, 200-300, 300-400 or 400-500 nucleotides. In some cases, the length, or number of nucleotides defined as either X or Y may be at least about 1, 2, 3, 4, 5, 6, 7, 8, 9, 10, 15, 20, 25, 30, 35, 40, 45, 50, 75, 100, 125, 150, 175, 200, 300, 400 or 500 nucleotides. In some cases, the length, or number of nucleotides defined as either X or Y may be at most about 1, 2, 3, 4, 5, 6, 7, 8, 9, 10, 15, 20, 25, 30, 35, 40, 45, 50, 75, 100, 125, 150, 175, 200, 300, 400 or 500 nucleotides.

In alternative configurations, barcodes may be formed through the combination of at least about 1, 2, 3, 4, 5, 6, 7, 8, 9 or 10 sequences. Barcodes may be formed the combination of at most about 1, 2, 3, 4, 5, 6, 7, 8, 9 or 10 non-unique sequences.

v. mPEAR Primers

An mPEAR primer can anneal to known sequences universal priming sites in the known sequences that have been joined to the fragments. An exemplary mPEAR primer, is diagrammed in FIG. 3, 350. An mPEAR primer can comprise: a universal amplification sequence, a target loci specific sequence, a molecular bar code, a spacer sequence and/or other known sequence(s). A universal amplification sequence may hybridize to a universal adapter sequence attached to the fragment. A spacer sequence may be of a variable length and can comprise degenerate nucleotides, known nucleotides or any combination thereof. A locus specific sequence may hybridize to a target locus, 300 or may hybridize to a region just upstream or downstream to a region of interest, 310. An mPEAR primer may be designed to anneal to a site upstream or downstream from the region of interest. In some embodiments, this can allow for increased specificity, e.g. pseudogenes and gene families with similar sequence homology can be avoided, thereby reducing false positives.

Multiple mPEAR primers may be used to target the same or different regions of interest. Two or more mPEAR primers may be used that target the same region of interest. Two or more mPEAR primers may be designed such that they tile a region of interest. Two mPEAR primers may be designed such that they target the same region but from inverse directions. The use of multiple mPEAR primers can allow for analysis of several regions of interest simultaneously.

mPEAR primers can hybridize to a target fragment DNA that has been joined or ligated to a known sequence. In some embodiments, the two separate regions that bind increase the specificity of the mPEAR primer.

In some embodiments, the universal 5' end of the mPEAR primer can serve to improve downstream sequencing. For example, the universal 5' end may stabilize the synthetic oligonucleotides toward the end of DNA library fragments. The universal 5' end may increase sequencer efficiency. The universal 5' end may keep a sequence, such as an anchor sequence, toward the beginning of the read. In downstream applications such as sequencing, this can, in some instances, allow a sequencer to appropriately position the target sequence without wasted sequencer capacity.

In some embodiments, blocking polynucleotides, such as blocking oligonucleotides or blocking oligos, can be used. In some embodiments, the primers can bind and cover the universal sequence at the 5' end thereby optionally reducing or eliminating the need for additional blocking oligos.

The spacer sequence consisting of degenerate nucleotides may be synthesized adjacent to the universal sequence. The number of degenerate nucleotides can be variable. Degenerate nucleotides can allow for some flexibility in the DNA library start and stop positions during DNA sequencing. This can allow for flexibility in the design of the locus specific priming sites. The presence of variable sequence start sites may help avoid systematic errors in the sequencing step, and can allow for a randomized error profile across the reads of the redundant DNA library fragments.

The locus specific priming site can be designed to recognize DNA sequences that are upstream of the actual target sequence. The locus specific region can be designed to be as short as possible without loss of function. In this context, 'function' refers to the ability of the double-stranded region to form a stable duplex under standard reaction conditions for an enzyme-catalyzed nucleic acid primer extension reaction, (e.g. incubation at a temperature in the range of 4° C. to 60° C. in an annealing buffer appropriate for the enzyme), such that the two strands forming the adaptor remain partially annealed during extension of the primer to a target molecule.

mPEAR primer regions may be designed to prevent self-annealing in a variety of ways. In some cases, the mPEAR primer can take the form such that either the universal priming site or the locus specific site may be longer than the one other. In such cases there is a single stranded region on one of the strands, or a sequence selected such that the two strands do not hybridize, and thus form a continuous single stranded primer. In some cases, sequence may be designed such that they anneal in 'bubbles' conformations, wherein both ends of the mPEAR primer construct(s) are capable of hybridizing to each other and forming a duplex, but the central region cannot for a duplex. The portion of the strand(s) forming the central region are not annealed under conditions in which other portions of the same two strands are annealed to form one or more double-stranded regions. In some instances, the longer the length of the mPEAR primer can correlate with the possibility that the mPEAR is able to base-pair to itself. Therefore, in some embodiments, the length can be reduced in order to reduce this effect. In some embodiments, the stability can also be increased by the inclusion of non-natural nucleotides which exhibit stronger base-pairing than standard Watson-Crick base pairs.

The actual nucleotide sequence of the mPEAR primers may be any suitable and may be selected by the user such that the desired sequence elements are ultimately included in the common sequences of the library of templates derived from the primers to, for example, provide binding sites for particular sets of universal amplification primers and/or sequencing primers. Additional sequence elements may be included, for example, to provide binding sites for sequencing primers which will ultimately be used in sequencing of template molecules in the library, or products derived from amplification of the template library, for example on a solid support in sequencing applications.

Generally mPEAR sequences may comprise DNA, but may also include any nucleotides or nucleotide derivatives that may be suitable. Alternative nucleotides may include mixtures of natural and non-natural nucleotides (e.g. one or more ribonucleotides) linked by a mixture of phosphodiester and non-phosphodiester backbone linkages. Other non-nucleotide modifications may be included such as, for example, biotin moieties, blocking groups and capture moieties for attachment, such as biotinylated nucleotides.

vi. mPEAR Elongation

A hybridized mPEAR primer can be extended to amplify all or a portion of the target fragment. A primer extension reaction may be performed using any suitable polymerase, 330, as described herein. Primer extension reactions are well known in the art and may include any suitable reagents for reaction. Selection of polymerases can be based on different criteria, including length of primer extension, enzyme fidelity, speed, turnover rate and the like. In some cases, Klenow or Klenow fragments may be suitable for a primer extension reaction.

Primer extension reaction, 370 conditions may vary and any combination of cycles, times and temperature may be used to perform one or more reactions. Reaction conditions may generally vary based on various parameters of primer design, including melting temperatures, predicted dimer-dimer formations, average extension length and the like.

Figure 3B:
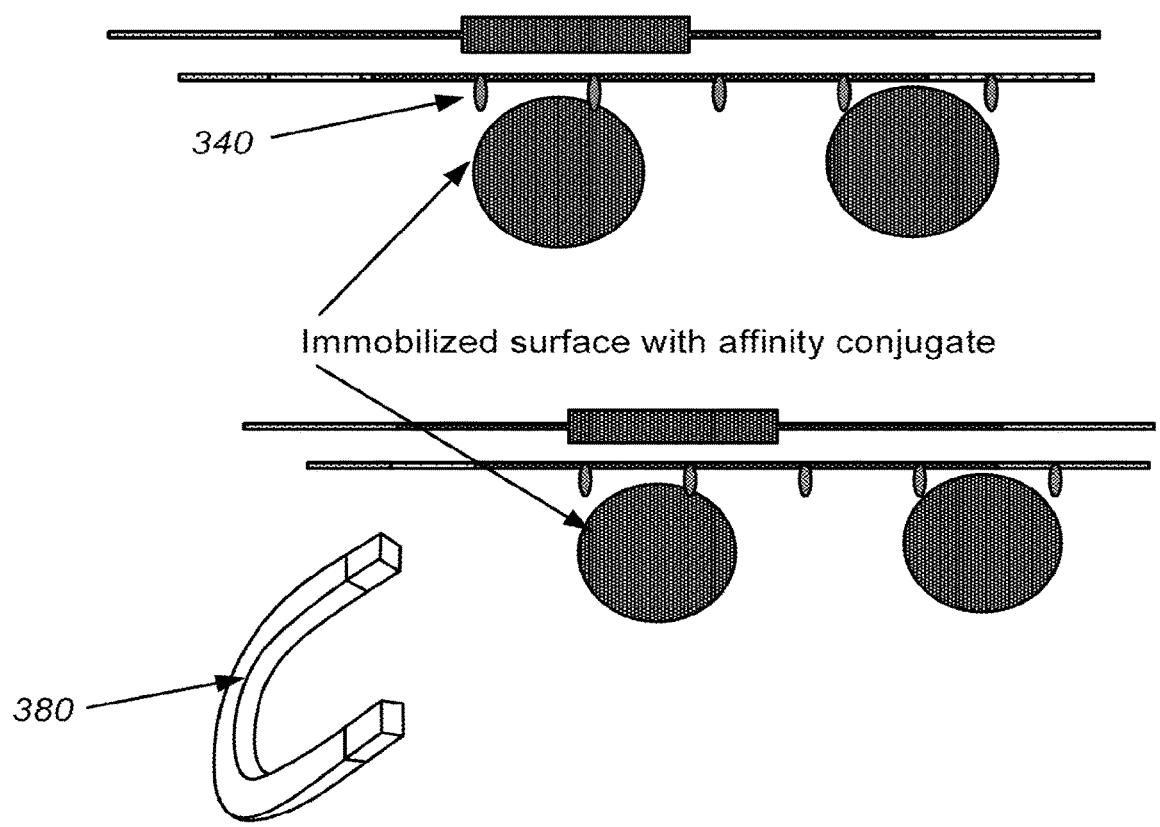
FIG. 3B depicts a representation of an affinity purification reaction of TELA or mPEAR labeled products.

In some embodiments, the extension reaction can be carried out in the presence of marked nucleotides. In some embodiments, some portion of the nucleotides in the reaction mix are marked with an affinity conjugate such as biotin, 340. The extension can occur through an elongation reaction using, e.g. a polymerase. The extension reaction can produce a complement to the targeted fragment. In some embodiments, the complement to the targeted fragment is marked with biotinylated nucleotides. The resulting primer extension products can comprise a library of template polynucleotides. In some cases, the primer itself may be biotinylated. In some embodiments, the library of template polynucleotides can be separated from other fragments in the mix using streptavidin. an immobilized surface with an agent used to bind the affinity conjugate for purification of the target molecule as shown in FIG. 3B. In some cases, the immobilized surface may comprise streptavidin to affinity purify the conjugate biotin. In some cases, the immobilized surfaces may be streptavidin coated beads which may be purified via used of a magnet, 380. In some cases the primer extension with affinity conjugate provides for more efficient or more specific capture of the probe than with current techniques in the art. In some cases current methods rely on affinity via hydrogen bonds of synthetic sequence to patient derived sequence. The synthetic sequence is designed by using the reference genome. In some cases patient derived sequence may be different than the synthetic sequence and in some cases this limits the binding efficiency.

vii. Library

The library of template polynucleotides can be amplified (e.g. by PCR or linear amplification reactions). Amplification can occur using primers that can hybridize to the known sequence at the 5' and 3' ends.

The contents of an amplification reaction are generally known in the art and may include appropriate substrates (such as dNTPs), enzymes (e.g. a DNA polymerase) and buffer components required for an amplification reaction. PCR amplification reactions can require at two amplification primers, often denoted 'forward' and 'reverse' primers (primer oligonucleotides) that are capable of annealing specifically to a part of the polynucleotide sequence to be amplified under conditions encountered in the primer annealing step of each cycle of an amplification reaction. In certain embodiments the forward and reverse primers may be identical. In linear amplification, one primer can be required.

During the amplification step, amplification may be performed using degenerate or universal primers for all samples or a forward primer that has sequences specific for the target polynucleotide, i.e. locus specific sequences).

Amplification methods include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al., Nucleic Acids Res. 20(7):1691-6 (1992), and rolling circle amplification, described in U.S. Pat. No. 5,648,245. Other amplification methods that may be used are described in, U.S. Pat. Nos. 5,242,794, 5,494,810, 4,988,617 and in U.S. Ser. No. 09/854,317 and US Pub. No. 20030143599, each of which is incorporated herein by reference. In some aspects DNA is amplified by multiplex locus-specific PCR. In some aspects the DNA is amplified using adaptor-ligation and single primer PCR. Other available methods of amplification, such as balanced PCR (Makrigiorgos, et al., Nature Biotechnol, 20:936-9 (2002)) and isothermal amplification methods such as nucleic acid sequence based amplification (NASBA) and self-sustained sequence replication (Guatelli et al., PNAS USA 87:1874 (1990)). Based on such methodologies, a person skilled in the art readily can design primers in any suitable regions 5' and 3' to a locus of interest. Such primers may be used to amplify DNA of any length so long that it contains the locus of interest in its sequence.

An amplification reaction may be performed with more than two amplification primers. In order to prevent the amplification of mPEAR dimers, the amplification primers can be modified to contain nucleotides that hybridize across the whole of the primer extension product and into the target molecule template (or the dNTP's attached to the 3' end thereof). A first amplification primer can be modified and treated to help prevent exonuclease digestion of the strands. A first amplification primer that is universal can amplify all samples rather than modifying and treating each of the tagged primers separately. A tagged primer can be introduced as a sample specific third primer in the amplification reaction, but does not need to be specially modified and treated to reduce exonuclease digestion. A third amplification primer that carries a tag can comprise a sequence that is the same as at least a portion of the first amplification primer such that it can be used to amplify the duplex resulting from extension of the first amplification primer.

A primer extension may be performed on one or both strands of the target molecule template. Primer extensions and subsequent amplifications can run through the end of the DNA library molecule. The use of an enzymatic primer extension on both strands of DNA can be adventageous. Two reactions targeting the same sequence can increase specificity and can reduce failure rates.

Amplification primers can be different lengths. In the case of nested PCR, the three or more amplification primers can be designed to be longer than the primer used to amplify the previous amplicon, so the length of the added nucleotides is fully controllable and may be hundreds of nucleotides if desired.

The forward and reverse primers can be of sufficient length to hybridize to the whole of the universal adaptor sequence and at least one base of the target sequence (or the nucleotide dNTP added as a 3'-overhang on the target strands). The forward and reverse primers can also contain a region that can extend beyond the adaptor construct. In some embodiments, the amplification primers can be at least 10, 20, 30, 40, 50, 60, 70, 80, 90 100, 150, 200, 300, 400 or 500 bases in length. In other embodiments, amplification primers may be at most 10, 20, 30, 40, 50, 60, 70, 80, 90 100, 150, 200, 300, 400 or 500 bases in length. The forward and reverse primers can be of significantly different lengths. In some embodiments, a first primer may be 20-40 bases, whereas a second primer may be 40-100 bases in length. The nucleotide sequences of the adaptor-target specific portions of the forward and reverse primers can be selected to achieve specific hybridization to the adaptor-target sequences to be amplified under the conditions of the annealing steps of the amplification reaction, while minimizing non-specific hybridization to any other target sequences present.

Amplification primers are generally single stranded polynucleotide structures. They can contain a mixture of natural and non-natural bases and also natural and non-natural backbone linkages.

Primers can contain sequences specific for capture on various platforms. In some cases, a sequence may be incorporated to allow hybridization to a known sequence in various high through platform kits, such as one provided by Illumina. Incorporation of hybridization sequences for parallel loading of samples onto a surface platform for sequencing is known in the art.

Primers can comprise non-nucleotide chemical modifications, for example phosphorothioates to increase exonuclease resistance, again provided such that modifications do not prevent primer function. Modifications may, for example, facilitate attachment, of the primer to a solid support, for example a biotin moiety. Certain modifications may themselves improve the function of the molecule as a primer, or may provide some other useful functionality, such as providing a site for cleavage to enable the primer (or an extended polynucleotide strand derived therefrom) to be cleaved.

Amplifications can be carried out on either the pooled or unpooled samples. Tags can be part of the amplification primers. In some embodiments, each sample can be amplified independently prior to pooling. The pooled nucleic acid samples can be processed for sequencing.

Amplification steps can be used to produce high quantities of higher quality sample. Amplification steps can be used to incorporate additional barcodes or adapter sequences with target polynucleotide sequences.

viii. Sample Capture

The pooled or unpooled sample can be captured in preparation for sequencing. Sequencing can be performed as an array of single captured targets. The amplification products can be attached on a planar surface, or on a pool of beads. The pool of beads can be isolated into an emulsion with a single bead in each 'partition' of the emulsion. At a concentration of only one template per 'partition', only a single template is amplified on each bead. In some embodiments, the methods of mPEAR targeting can be used in combination with the methods of genome RAPELLing.

Any chemical means for capture of amplified product may be suitable. In some embodiments, a single point covalent attachment to a solid support at or near the 5' end of the primer, leaving the template-specific portion of the primer free to anneal to its cognate template and the 3' hydroxyl group free for primer extension is suitable for capture. Any suitable covalent attachment means known in the art may be used for this purpose. The chosen attachment chemistry will depend on the nature of the solid support, and any derivative or functionalization applied to it. The primer itself may include a moiety, which may be a non-nucleotide chemical modification, to facilitate attachment. In a particular embodiment, the primer may include a sulphur-containing nucleophile, such as phosphorothioate or thiophosphate, at the 5' end.

In other embodiments, capture may be achieved through biotin-streptavidin, or streptavidin derivatives, interactions. Amplified products that comprise biotin may be incubated with surfaces with streptavidin or streptavidin derivatives, thus allowing products to be immobilized as shown in FIG. 3B. Purification methods, known in the art may be used to retrieve amplification products, such as through the use of magnets and/or streptavidin coated beads. In some embodiments, additional wash steps can be used. Amplification products can be eluted by flushing with excess concentrations of biotin or biotin related compounds as shown in FIG. 3C. Methods known in the art for biotin-streptavidin affinity purification of polynucleotides (see U.S. Pat. Nos. 5,405,746, 5,500,356 and 5,759,778) are incorporated by reference in their entirety.

ix. Sequencing and Data Analysis mPEAR samples can be sequenced by any method known in the art, several non-limiting examples are disclosed herein. Sequencing can produce data. The data can be stored, processed, and transmitted as disclosed herein.

Figure 9:
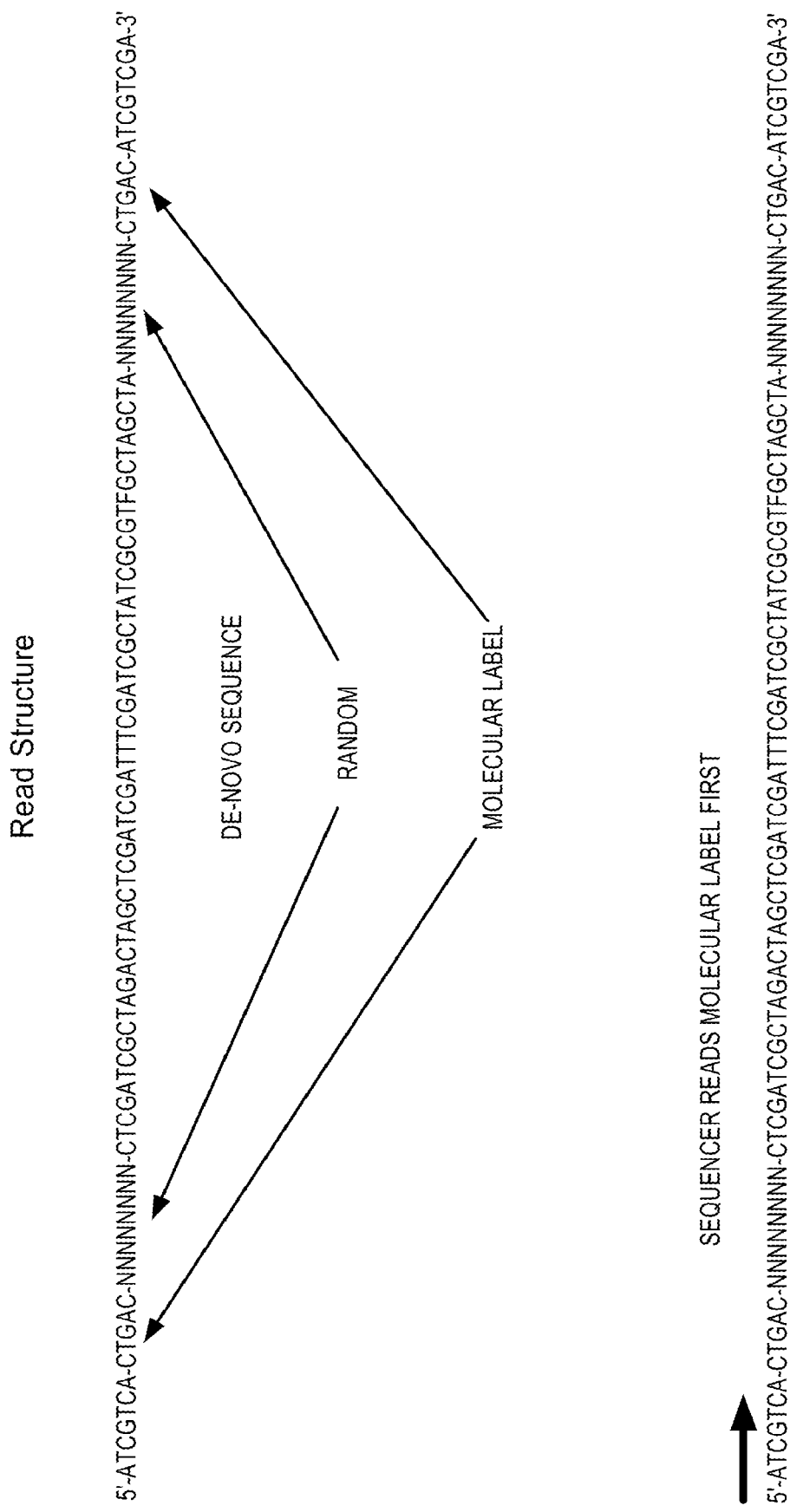
FIG. 9 depicts an example read structure of sequencing generated from mPEAR, TELA, RAPEL or other products of the methods and compositions of this disclosure.

The read structure, as depicted in FIG. 9 of the captured molecules can offer significant advantages in speed and quality of data analysis. Because the locus specific primer recognition site can be designed to hybridize upstream of the target sequence, that locus specific site may be used to identify the genomic location of the read. This can be generally referred to as "anchored read alignment" and can greatly reduce the amount of data processing and statistical analysis. In one non-limiting example, instead of taking short sequence reads and in silico aligning them to the entire reference genome, reads can be automatically binned or associated to their correct genomic position. This can greatly reduce the time for data analysis, increase accuracy, and decrease the computational power needed for such analysis.

In addition the mPEAR method can allow for true de novo sequencing of polynucleotide targets. Thus, by "anchoring" the read with the known sequence, elongation product can be assembled without the use of a reference genome. Thus mPEAR allows for greater sensitivity of genomic loci that greatly differ from the reference genome. Longer insertions, larger deletions, and repeats that are clinically relevant can be detected with greater sensitivity and accuracy. Viral insertion sites and/or mobile polynucleotide elements can be detected and localized and this process can be multiplexed for greater efficiency.

Figure 13:
FIG. 13 depicts a schematic of physical separation of target sequences and de novo assembly of sequences based on bar code sequences.

The optional addition of one or more barcodes can allow for, e g, binning of the sample to the sequence read. Barcoding can be useful for a variety of applications, including tracking of individual polynucleotide molecules, as shown in FIG. 13. In some embodiments, DNA molecule reads can be associated to a sample. In some embodiments, mPEAR barcoding can be used to phase information, in which individual molecules may be identified as paternally or maternally inherited from a single individual.

E. Single End Adapter Library and Rolling Circle Amplification

Rolling circle amplification can be used with targeting methods. Rolling circle amplification can be used to generate a linear amplification reaction.

i. Fragmentation

Figure 12:
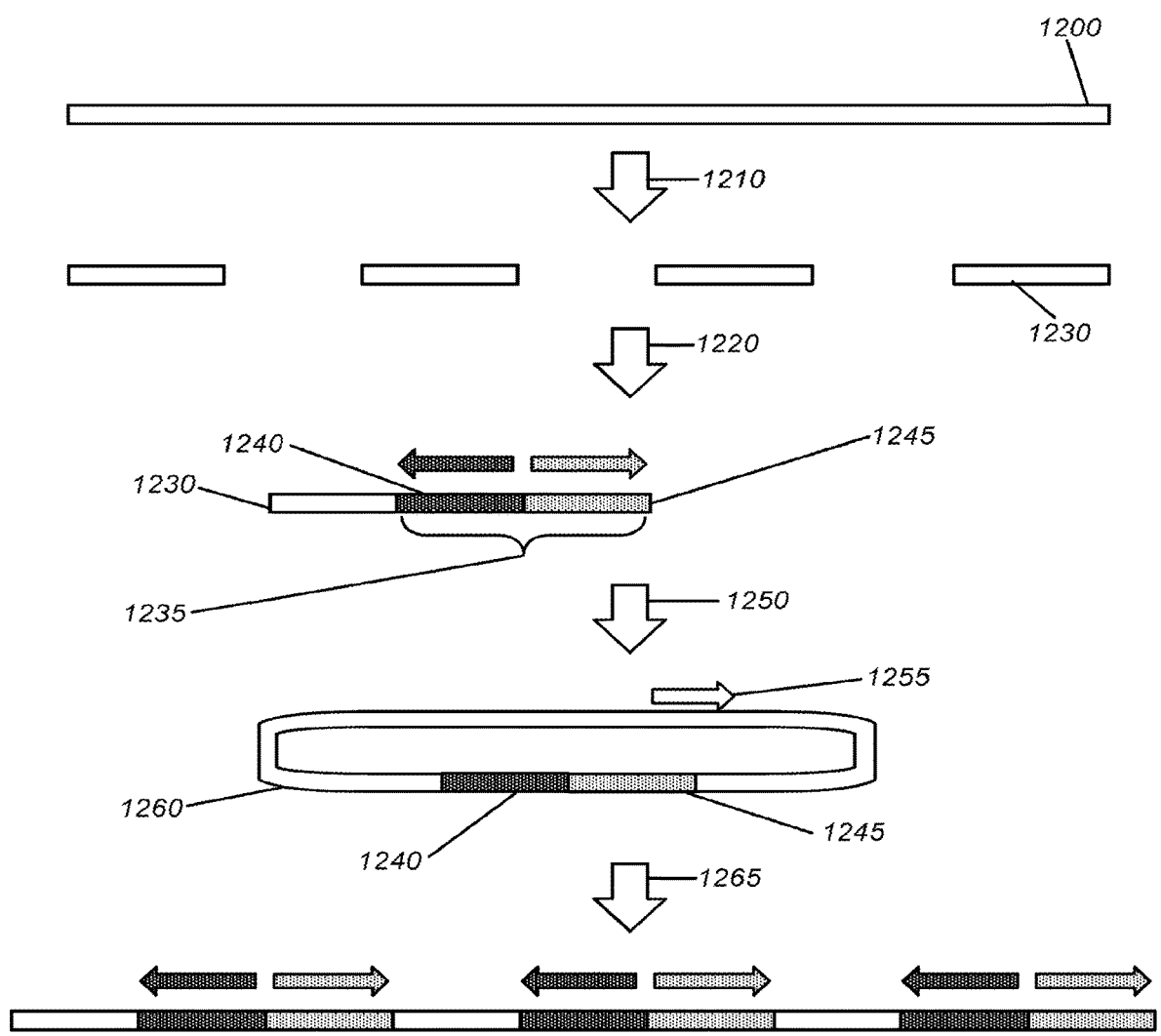
FIG. 12 depicts a schematic representation of compositions and methods of the disclosure using rolling circle amplification to assemble multiple contiguous sequence targets.

A polynucleotide sample, 1200 may be first fragmented, 1210 before subsequent steps as shown in FIG. 12. Fragmentation methods have been described herein. The size of the polynucleotide fragments, described in terms of length, may vary depending on the source of the target polynucleotide, the method used for fragmentation, and the desired application. In some cases one or more fragmentation steps may be used. For example, 1, 2, 3, 4, 5, 6, 7, 8, 9, 10, 11, 12, 13, 14, 15, or more fragmentation steps may be used.

In some cases nucleic acids may be fragmented into sizes atleast 10, 20, 30, 40, 50, 60, 70, 80, 90, 100, 200, 300, 400, 500, 600, 700, 800, 900, 1000, 2000, 3000, 5000 base pairs in length. In some cases nucleic acids may be fragmented into sizes at most 10, 20, 30, 40, 50, 60, 70, 80, 90, 100, 200, 300, 400, 500, 600, 700, 800, 900, 1000, 2000, 3000, 5000 base pairs in length.

Numerous fragmentation methods are described herein and known in the art. For example, fragmentation may be performed through physical, mechanical or enzymatic methods. Physical fragmentation may include exposing a target polynucleotide to heat or to UV light. Mechanical disruption may be used to mechanically shear a target polynucleotide into fragments of the desired range. Mechanical shearing may be accomplished through a number of methods known in the art, including repetitive pipetting of the target polynucleotide, sonication and nebulization. Target polynucleotides may also be fragmented using enzymatic methods. In some cases, enzymatic digestion may be performed using enzymes such as using restriction enzymes.

Restriction enzymes may be used to perform specific or non-specific fragmentation of target polynucleotides. The methods of the present disclosure may use one or more types of restriction enzymes, generally described as Type I enzymes, Type II enzymes, and/or Type III enzymes. Type II and Type III enzymes are generally commercially available and well known in the art. Type II and Type III enzymes recognize specific sequences of nucleotide base pairs within a double stranded polynucleotide sequence (a "recognition sequence" or "recognition site"). Upon binding and recognition of these sequences, Type II and Type III enzymes cleave the polynucleotide sequence. In some cases, cleavage will result in a polynucleotide fragment with a portion of overhanging single stranded DNA, called a "sticky end." In other cases, cleavage will not result in a fragment with an overhang, creating a "blunt end." The methods of the present disclosure may comprise use of restriction enzymes that generate either sticky ends or blunt ends.

Restriction enzymes may recognize a variety of recognition sites in the target polynucleotide. Some restriction enzymes ("exact cutters") recognize only a single recognition site (e.g., GAATTC). Other restriction enzymes are more promiscuous, and recognize more than one recognition site, or a variety of recognition sites. Some enzymes cut at a single position within the recognition site, while others may cut at multiple positions. Some enzymes cut at the same position within the recognition site, while others cut at variable positions.

ii. Nucleic Acid Strand End Repair

In many cases, fragmentation of nucleic acids, such as through mechanical shearing or enzymatic digestion results in fragments with a heterogeneous mix of blunt and 3'- and 5'-overhanging ends. In some cases, the compositions and methods of the disclosure provide for repair of the fragment ends using methods or kits (i.e. Lucigen DNA terminator End Repair Kit) known in the art to generate ends that are designed for insertion, for example, into blunt sites of cloning vectors. In some cases, the compositions and methods of the disclosure provide for blunt ended fragment ends of the population of DNAs sequenced. Further, in some cases, the blunt ended fragment may also be phosphorylated. The phosphate moiety can be introduced via enzymatic treatment, for example, using a kinase, (i.e. shrimp alkaline kinase).

In other cases, polynucleotide sequences are prepared with single overhanging nucleotides by, for example, activity of certain types of DNA polymerase such as Taq polymerase or Klenow exo minus polymerase which has a nontemplate-dependent terminal transferase activity that adds a single deoxynucleotide, for example, deoxyadenosine (A) to the 3' ends of, for example, PCR products. Such enzymes can be utilized to add a single nucleotide 'A' to the blunt ended 3' terminus of each strand of the target polynucleotide duplexes. Thus, an 'A' could be added to the 3' terminus of each end repaired duplex strand of the target polynucleotide duplex by reaction with Taq or Klenow exo minus polymerase, whilst the adaptor polynucleotide construct could be a T-construct with a compatible 'T' overhang present on the 3' terminus of each duplex region of the adaptor construct. This end modification also prevents self-ligation of both adapter and target such that there is a bias towards formation of the combined ligated adaptor-target sequences.

In some cases, Nextera kits such as provided by Illumina/Epicentre, which use a tn5 transposase to simultaneously fragment the double-stranded DNA and ligate adapters to the ends of the fragments may be used. For example, the amplified cDNA is 'tagmentated' at 55° C. for 5 min in a 20-µl reaction with 0.25 µl of transposase and 4 µl of 5×HMW Nextera reaction buffer (containing Illumina-compatible adapters). To strip the transposase off the DNA, 35 µl of PB is then added the tagmentation reaction mix, and the tagmentated DNA was purified with 88 µl of SPRI XP beads (sample to beads ratio of 1:1.6). The reagents for this method are available in Nextera DNA sample kits (Epicentre/Illumina). Alternative kits may also be used, such as provided by Roche FLX and Titanium sequencing systems.

In some cases, cDNA fragmentation may not be performed. Rather, RNA molecules, before reverse transcription to cDNA, may be fragmented using any suitable method, including applicable techniques described herein and as described by Hashimony et al Hashimshony, 2012.

In some cases, the fragmented DNA is size-selected using agarose gel methods such as SizeSelect™ Gels (Life Technologies) or Pippin Prep™ kits or beads such as AMPure XP (Beckman Coulter). In other embodiments, fragmented DNA is end repaired or polynucleotide tailed for subsequent steps of library preparation.

Fragmentation of polynucleotides, such as through mechanical shearing or enzymatic digestion, can result in fragments, 1230 with a heterogeneous mix of blunt and 3'- and 5'-overhanging ends. In some cases, the fragment ends can be repaired or treated, 1220. Such methods for polynucleotide strand end repair have been described herein.

iii. Attachment of Known Sequence

Known sequences can be attached to the ends of the fragmented polynucleotide sample. Methods for attachment of known sequences (e.g. ligation) have been described herein.

The known sequence, 1235, can comprise a molecular barcode, one or more adapter(s), or any other sequence such as a universal primer sequence. In some embodiments, the known sequence comprises two adapters, an A adapter 1240, and a B adapter, 1245 that can sit in an "inverted" matter. The "inverted" manner can mean that the 5' end of the A adapter can be linked to the 5' end of the B adapter. In some embodiments, a restriction enzyme or other nuclease site may be engineered between the A and B adapters.

iv. Ligation

The fragmented polynucleotide attached to the known sequence can be circularized. Circularization can be accomplished through ligation, 1250. In some embodiments, the 5' end of the fragment is ligated to the 3' end of the known sequence. In other embodiments, the 3' end of the fragment is ligated to the 5' end of the known sequence.

v. Amplification

The circularized polynucleotide can be amplified through a rolling circle amplification process. In such a process, a primer, 1255 can hybridize to of the circularized polynucleotide, 1260. A polymerase can elongate and copy the circularized template, i.e. rolling circle amplification. The polymerase can copy the circularized template 1, 2, 3, 4, 5, 6, 7, 8, 9, 10, 11, 12, 13, 14, 15, 16, 17, 18, 19, 20, 25, 30, 40, 50, 60, 70, 80, 90, 100, 200, 300, 400, 500 times or more. This can result in a linear copy that comprises one or more sequential linear copies, 1265. In some embodiments there can be 1, 2, 3, 4, 5, 6, 7, 8, 9, 10, 11, 12, 13, 14, 15, 16, 17, 18, 19, 20, 25, 30, 40, 50, 60, 70, 80, 90, 100, 200, 300, 400, 500 copies in a linear polynucleotide. These copies can be cleaved by a restriction enzyme or nuclease to create a library for sequencing. In some embodiments, PCR amplification methods can be used to add full length adapter sequences to the 5' and 3' ends, thereby producing a library for sequencing. Methods for using PCR primers to add known sequences to an amplified product have been disclosed herein.

In some cases, tiled locus specific primers can be used for amplifying circular molecules that contain the sequences of interest. Primers may be designed upstream of targets and tiled across the full length of the target. Primers may be designed in both directions as well. Double stranded DNA "circles" may be de natured and locus specific primers bind (both directions). As rolling circle amplification occurs, amplified product may be displaced from the template molecule. Excess primers may bind to the growing strand and amplify the extended copy in the alternate direction to form long double stranded DNA molecules with repetitive sequence. The repetitive sequence may include A and B adapter sequences flanking the target sequence. This can now be used as a template for PCR to amplify in the full length sequencing adapters. In other cases a restriction site in between the adapters becomes active when the ends of the molecule are joined.

vi. Sequencing and Data Analysis

Rolling circle amplification samples can be sequenced by any method known in the art; several non-limiting examples are disclosed herein. Sequencing can produce data. The data can be stored, processed, and transmitted as disclosed herein.

II. DNA Labeling for De Novo Sequencing and Labeling

A. Random Primer Extension, Ligation and Labeling (RAPELL)

Figure 1B:
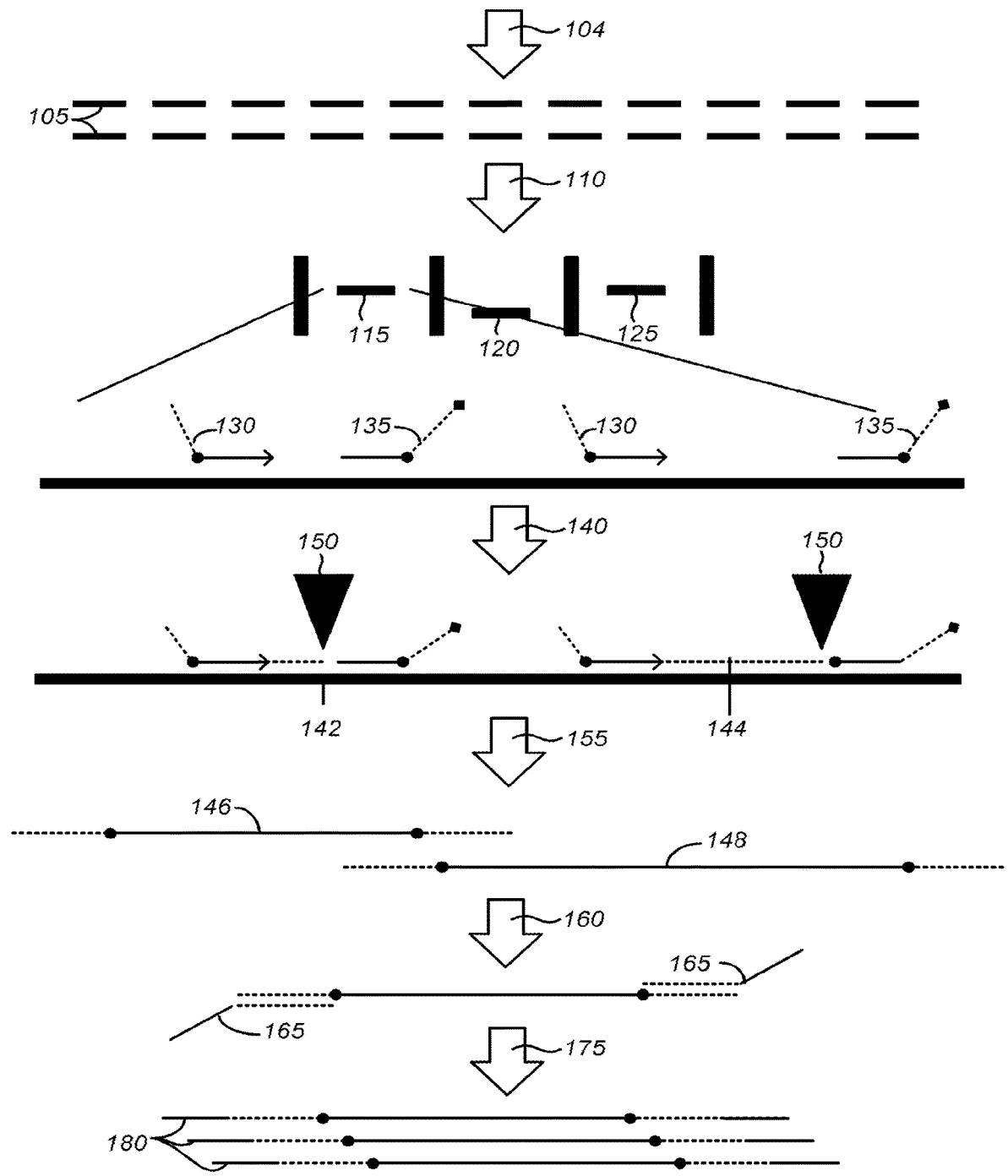
FIG. 1B depicts a schematic representation of a workflow involving targeted sequencing.

Methods of random primer extension ligation and labeling (RAPELL) can be used for obtaining sequence information of long fragments of nucleotides using short read systems. RAPELL methods can comprise: polynucleotide isolation, purification, dilution, and spatial separation before amplification and incorporation of a molecular label and finally sequencing. FIG. 1 depicts an exemplary method according to the disclosure. FIG. 1A shows a process 100 for obtaining sequence information of long fragments of nucleotides using short read systems using the mPEAR system, as described herein. The process 100 comprises obtaining a sample of long nucleic acid 105 of high molecular weight (over 5 kilobases). FIG. 1B shows a process for further processing of high molecular weight nucleic acid. The long nucleic acid 105 is diluted and spatially separated 110 in sub genome quantities into several partitions (e.g. 115, 120, 125). Each partition 115, 120, 125 may contain a long nucleic acid 105. In each partition, the long nucleic acid fragment 105 comes into contact with a polymerase/ligase mixture, containing primers 130, and adapters 135. The primers 130 can comprise a random sequence at the three prime end to allow for random binding along the long nucleic acid fragment 105 and a region of know sequence (represented by a circle and a dashed line and a 3' cap (represented by a diamond shape). A polymerase reaction 140 extends the primers 130 are along various random areas of the template nucleic acids until the elongation product (e.g. 142, 144) reaches a downstream adaptor 135. A ligase 150 ligates 155 the elongation product to the downstream adaptor and an amplicon library (e.g. 146, 148) is created. A second set of primers (e.g. 165, 170) can be added 160 for a polymerase chain reaction (PCR) 175, thereby producing a library suitable for sequencing 180.

i. Sample Acquisition

RAPELL methods can use a polynucleotide of long molecular length. The sample can come from a nucleic acid library, such as a cDNA library. The sample can come from genomic DNA. The nucleic acid can also be isolated from one or more subjects. In some exemplary methods, the nucleic acid is deoxynucleic acid (DNA) of high molecular weight. High molecular weight can refer to, for example approximately more than 0.5, 1, 3, 4, 5, 10, 15, 20, 30, 35, 40, 50, 60, 70, 80, 90, 100, 200 or more kilobases. The nucleic acid sample can contain nucleic acid fragments that range in size from approximately 1-50 kb, 5-50 kb, 5-100 kb, 20-90 kb, 50-100 kb, 5-200 kb. The nucleic acid can be largely purified from cellular components. The sample of nucleic acid may be in chromosomal form. In some instances, the polynucleotide may be fragmented in to smaller sizes. Methods for polynucleotide fragmentation have been disclosed herein. In some instances, methods known in the art (e.g. physical shearing or enzymatic digestion) may be used to fragment the chromosomal nucleic acid into sizes such as approximately 1, 3, 4, 5, 10, 15, 20, 30, 35, 40, 50, 60, 70, 80, 90, 100, 200 kb or into sizes that range from −50 kb, 5-50 kb, 5-100 kb, 20-90 kb, 50-100 kb, 5-200 kb.

ii. Dilution and Spatial Separation

The present invention uses dilution and spatial separation of sample nucleic acid. In some instances, long fragments of nucleic acid are diluted before being spatially separated. Dilution can be accomplished by any method known in the art, such as by the addition of a dilute, such as water, or a suitable buffer. An exemplary method of dilution involves determining the concentration of the nucleic acid before dilution and calculating how much dilute to add so that the diluted sample can be partitioned into quantities that contain sub-genomic quantities of DNA (i.e. so that one sample contains less than one whole genome). In another exemplary method, dilution can be calculated so that the sample can be partitioned in a way that each partition contains approximately 1, 2, 3, 5, 10, 20, 50, 80, 100, 150, 200, 400, 500, 1000, 1500, 5,000, 10,000, 100,000, 1,000,000, 10,000,000, 100,000,000, 1,000,000,000 fragments of nucleic acid. In another exemplary method, dilution is accomplished to facilitate partitioning sample so that approximately 1%, 2%, 5%, 10%, 15%, 20%, 30%, 50%, 70%, 80%, 95% or 100% of one copy of the genome can be separated.

Spatial separation can be accomplished by many methods known in the art, such as pipetting, micropipeting, or microfluidics. Partitions can be made of any known methods in the art, including plates (e.g. 96-well), mirofluidic chambers, micro-droplets, or simple spatial separation on solid surfaces such as silicon chips or beads.

In an exemplary method, dilution and spatial separation is conducted so that the there is a low probability that two partitions contain the same locus of DNA from each parental chromosome, or that multiple fragments from the same genomic locus will be extremely rare.

iii. Primer Extension, Ligation and Amplification

In a partition, the diluted polynucleotide can come into contact with a mixture of synthetic oligonucleotids, native dNTPs, polymerase (or polymerase fragments), ligase and associated buffers sufficient for primer extension and ligation. The said mixture of synthetic oligonucleotides is comprised of a donor primer and an acceptor probe.

a. Donor Primer

The present invention can use a donor primer to generate complementary regions of the diluted template. FIG. 22A is an illustration diagramming an exemplary donor primer 200. A donor primer may comprise: an adapter sequence 205, a molecular label (i.e. bar code) 210 and a region of random primer 215. A donor primer can be made of nucleotides comprising DNA nucleotides, RNA nucleotides, or any combination thereof.

An adapter sequence 205 can be located near the 5' end of the donor primer 200. An adapter sequence can have a length of approximately 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 75, 80, 85, 90, 95, 100, 125, 130, 150, 200 or more nucleotides. In some instances the adapter sequence 205 may be designed with such a sequence that secondary structure may form such as a hairpin, or stem-loop. To facilitate secondary structure formation and release one or more uracil bases can be added. An adaptor that can form a secondary structure may be used in some instances to reduce binding of donor primers with RAPELL products. The secondary structure may be designed such that it can be selectively eliminated by cutting. Selective cutting of the hairpin may be accomplished by the use of an enzyme, such as a nuclease, e.g. Drosha.

A molecular barcode 210 can be designed to designate which partition the reaction takes place in. Therefore the number of molecular barcodes may equal the number of partitions used for the reaction. In one non limiting example, 96 different donor primers could be used, each with a different molecular label if nucleotide fragments were separated into 96-well plate partitions. The molecular label can be 1, 2, 3, 4, 5, 6, 7, 8, 9, 10, 11, 12, 13, 14, 15, 16, 17, 18, 19, 20 or more nucleotides in length.

The 3' prime end of the donor primer can comprise a random sequence that can act as a random primer. Random primers can be short segments of nucleic acid that can hybridize to a template and prime a reaction. The random region can comprise 6, 7, 8, 9, 10, or more nucleotides. In one non-limiting example, the region can be 6 nucleotides long (i.e. a hexamer) and therefore the mixture of primers can contain every possible combination of bases ($4^6$=4,096 total possible combinations). In another non-limiting example, the region can be 8 nucleotides long (i.e. an octamer) and the mixture of donor primers can contain every possible combination of bases ($4^8$=65,563 total possible combinations).

b. Acceptor Probe

The present invention can use an acceptor probe 240 that can bind to the template. FIG. 2B is an illustration diagramming an exemplary acceptor probe 240. An acceptor probe may comprise: an adapter sequence 230, a molecular barcode 225 and a region of random primer 220. An acceptor probe can be made of nucleotides comprising DNA nucleotides, RNA nucleotides, or any combination thereof. An acceptor probe 240 may contain a 3' cap 235 on the 3'-most nucleotide to prevent extension or elongation from the acceptor probe 240.

The 5' prime end of the acceptor probe 240 comprises a random primer 230. Random primers 230 can be short segments of nucleic acid that consist of every possible combination of bases. The random region can comprise 6, 7, 8, 9, 10, or more nucleotides. In one non-limiting example, the region can be 6 nucleotides long (i.e. a hexamer) and therefore the mixture of primers can contain every possible combination of bases ($4^6$=4,096 total possible combinations). In another non-limiting example, the region can be 8 nucleotides long (i.e. an octamer) and the mixture of acceptor probes can contain every possible combination of bases ($4^8$=65,563 total possible combinations).

A molecular bar code 310 can be designed to designate which partition the reaction takes place in. Therefore the number of molecular barcodes 310 needed for each acceptor probe 300 may equal the number of partitions used for the reaction. In one non limiting example, 96 different donor primers could be used, each with a different molecular label if nucleotide fragments were separated into 96-well plate partitions. The molecular label can be 1, 2, 3, 4, 5, 6, 7, 8, 9, 10, 11, 12, 13, 14, 15, 16, 17, 18, 19, 20 or more nucleotides in length. The adaptor probe 240 and donor primer 200 with the same molecular label may paired and used in the same partition. In some embodiments, the adaptor probe 300240 and the donor primer 200 will be paired so that their molecular labels are different and used in the same partition.

An adapter sequence 230 can be located near the 3' end of the adapter probe 300. An adapter sequence may have a length of approximately 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 75, 80, 85, 90, 95, 100, 125, 130, 150, 200 or more nucleotides. In some instances the adapter sequence 230 may be designed with such a sequence that secondary structure may form such as a hairpin, or stem-loop. To facilitate secondary structure formation and release one or more uracil bases may be added. An adaptor that can form a secondary structure may be used in some instances to reduce binding of acceptor probes 240 with RAPELL products. The secondary structure may be designed such that it can be selectively eliminated by cutting. Selective cutting of the hairpin may be accomplished by the use of an enzyme, such as Drosha.

iv. Binding and Elongation

Figure 4:
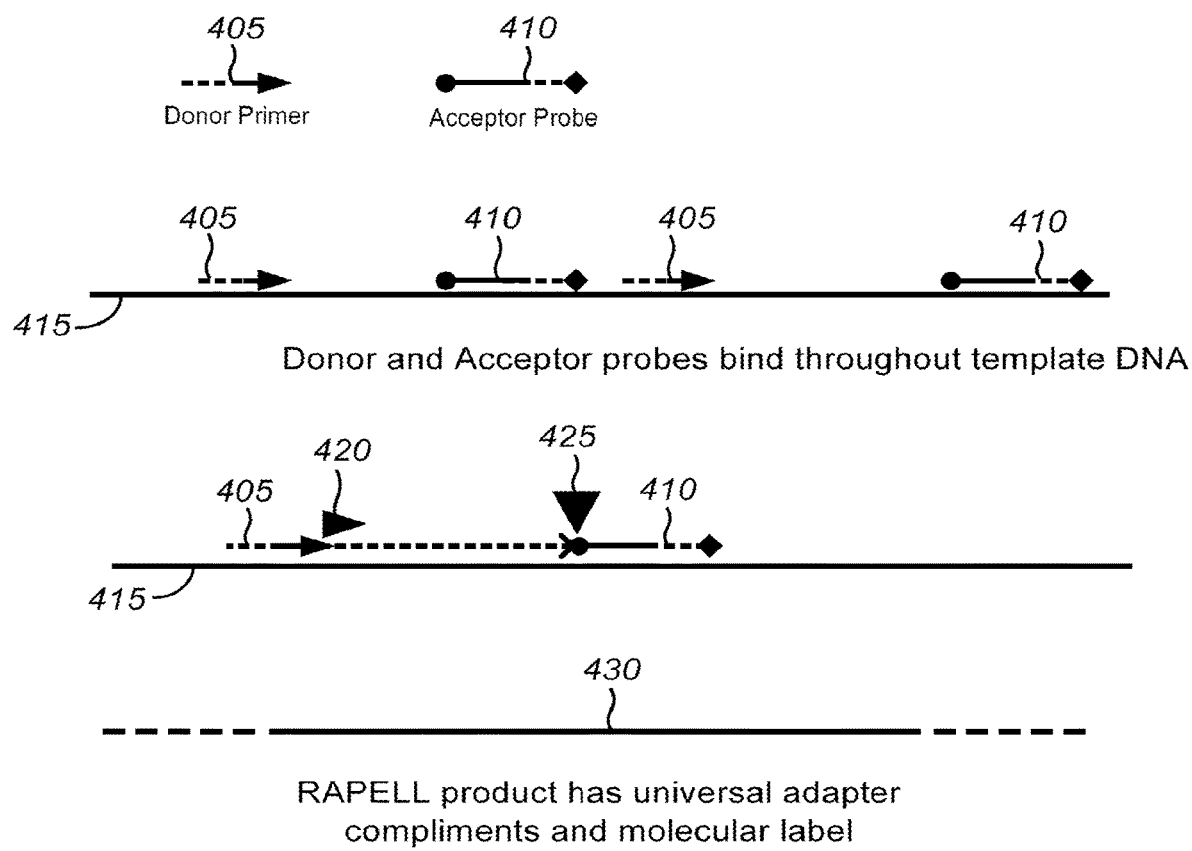
FIG. 4 depicts a representation of RAPEL methods.

FIG. 4 illustrates an exemplary process of binding and elongation 400 of donor primers 405 and acceptor probes 410. The random primer region of the acceptor probe 410 and the donor primer 405 can bind to regions along the template. Since the mixture of donor primers 405 and acceptor probes 410 may have, for example, every combination of hexamer or octamer bases, the acceptor probes and donor primers can anneal throughout the template 415 in a manner that can produce statistically random RAPELL products 430. Once the donor primer 405 and the acceptor probe 410 have annealed, a non-strand displacing polymerase 420 can extend the donor primer 405 until it reaches the acceptor probe 410. A non-strand displacing polymerase can be used to fully extend. Once the extension has reached the acceptor probe 410, a ligase 425 may be used to ligate the extension product and the acceptor probe 410 to create a RAPELL product 430. The methods of binding and elongation can be repeated in the same partition to produce a plurality of RAPELL products 430. In some instances the plurality of RAPELL products can comprise hundreds, thousands, or millions, of short copies of the template fragment. The resulting RAPELL products 430 can be of variable length and can be released from the template by melting.

In some examples a preamplification step may be used. For instance by ligating adapters to the ends of long DNA fragments, spatially separating the fragments and then performing long range PCR. Then the random RAPELL primers are used as described. Targeted long range PCR may also be performed by using the multiplexed PCR preamplification previously described.

v. RAPELL Product

The methods disclosed herein can generate a RAPELL product 430. The RAPELL product can be comprised of: the donor primer 405 and the acceptor probe 410. The RAPELL product can have adaptor regions on the 5' and 3' ends. In some instances, the RAPELL product can be processed, if, for example, a secondary structure has been generated on the 5' or 3' end. The secondary structure may be selectively eliminated by cutting. Selective cutting of a secondary structure, such as a hairpin, can be accomplished by the use of an enzyme, such as Drosha.

vi. Amplification

Figure 5:
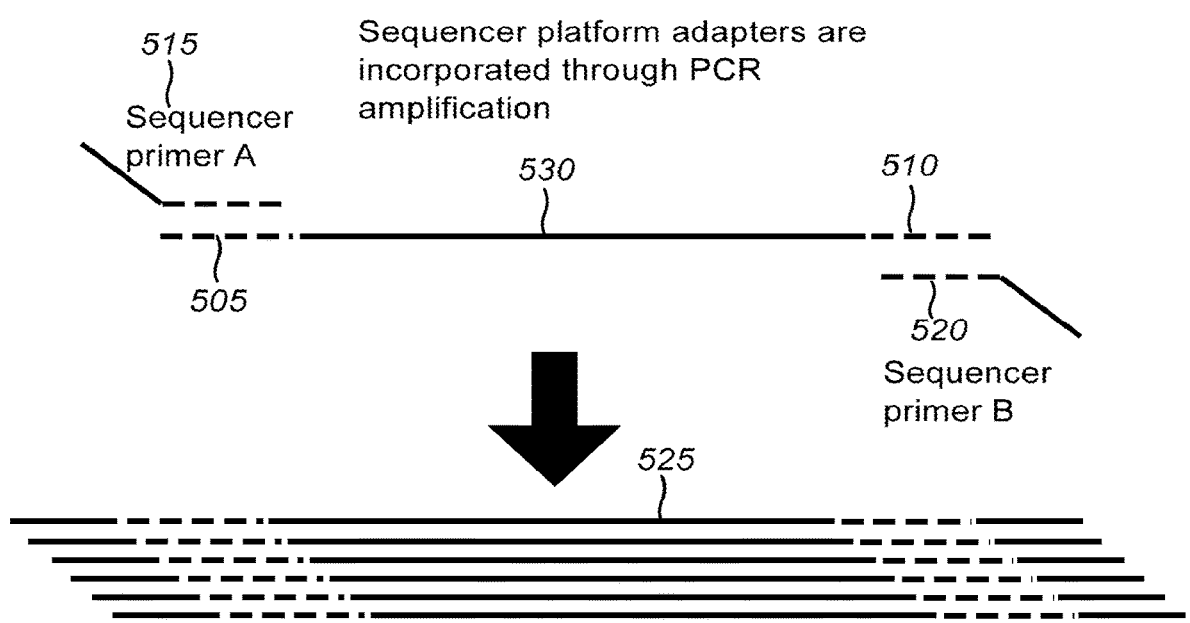
FIG. 5 depicts a representation of use of sequencer platform adapter with targeted sequencing products.

FIG. 5 illustrates an exemplary method 500 of how a RAPELL product 530 can be amplified by polymerase chain reaction (PCR). To amplify a RAPELL product 530 primers complementary to the adaptor sequences (e.g. integrated into the RAPELL product through the donor primer 505 and acceptor probe 510) can be used (e.g. Sequencer primer A 515 and Sequencer primer B 520). In some instances a RAPELL product 530 can be amplified to produce a plurality of RAPELL products for a sequencing library 525. A plurality of RAPELL products 530 can be amplified in the same reaction chamber using. In some embodiments, RAPELL products 530 that exist in separate partitions (see FIG. 1) may be pooled rather than running a reaction in each separate partition.

The Sequencer primers (e.g. Sequencer primer A 515 and Sequencer primer B 520) can comprise: a first region that can bind to the adaptor sequences (e.g. 505 and 510) and a region suitable for a specific sequencing platform adapter sequence (e.g. an Illumina sequence). Cycling conditions of the amplification reaction can be optimized or adjusted to produce a desired fragment size, or fragment size range optional for sequencer performance. A size selection and quantification can be used to achieve optimal sequencer performance.

vii. Sequencing and Data Analysis

Each copy can contain a identifier specific to a single partition of the reaction. Each sequencer read can be anchored to a single partition and thus can be stitched to a longer template fragment. Long read lengths are achieved by combining overlapping sequences from the same molecular barcode (i.e. the same partition).

III. Sequencing

Numerous methods of sequence determination can be used. Exemplary methods for sequence determination include, but are not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459,311 and 6,210,891; Balasubramanian, U.S. Pat. Nos. 7,232,656 and 6,833,246; Quake, U.S. Pat. No. 6,911,345; Li et al, Proc. Natl. Acad. Sci., 100: 414-419 (2003); pyrophosphate sequencing as described in Ronaghi et al., U.S. Pat. Nos. 7,648,824, 7,459,311, 6,828,100, and 6,210,891; and ligation-based sequencing determination methods, e.g., Drmanac et al., U.S. Pat. Appln No. 20100105052, and Church et al, U.S. Pat. Appln Nos. 20070207482 and 20090018024.

Sequence determination may also be determined using methods that determine many (typically thousands to billions) of nucleic acid sequences in an intrinsically parallel manner, where many sequences are read out preferably in parallel using a high throughput serial process. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeg™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

Some methods of sequencing require an adapter sequence, sometimes referred to as an "adapter" or a "sequence adapter". Adapter sequence can be platform specific. Adapters can comprise an anchor. Adapters can comprise a sequencing sequence. Adapters can comprise an amplification sequence. In some embodiments, an adapter sequence can comprise an anchor, a sequencing sequence, and an amplification sequence. An adapter sequence can be added to the 5' end. An adapter sequence can be added to the 3' end. Adapter sequences can be added to both the 3' and 5' end. Adapter sequences can facilitate sequencing.

IV. System for Data Transmittal and Storage

Figure 11:
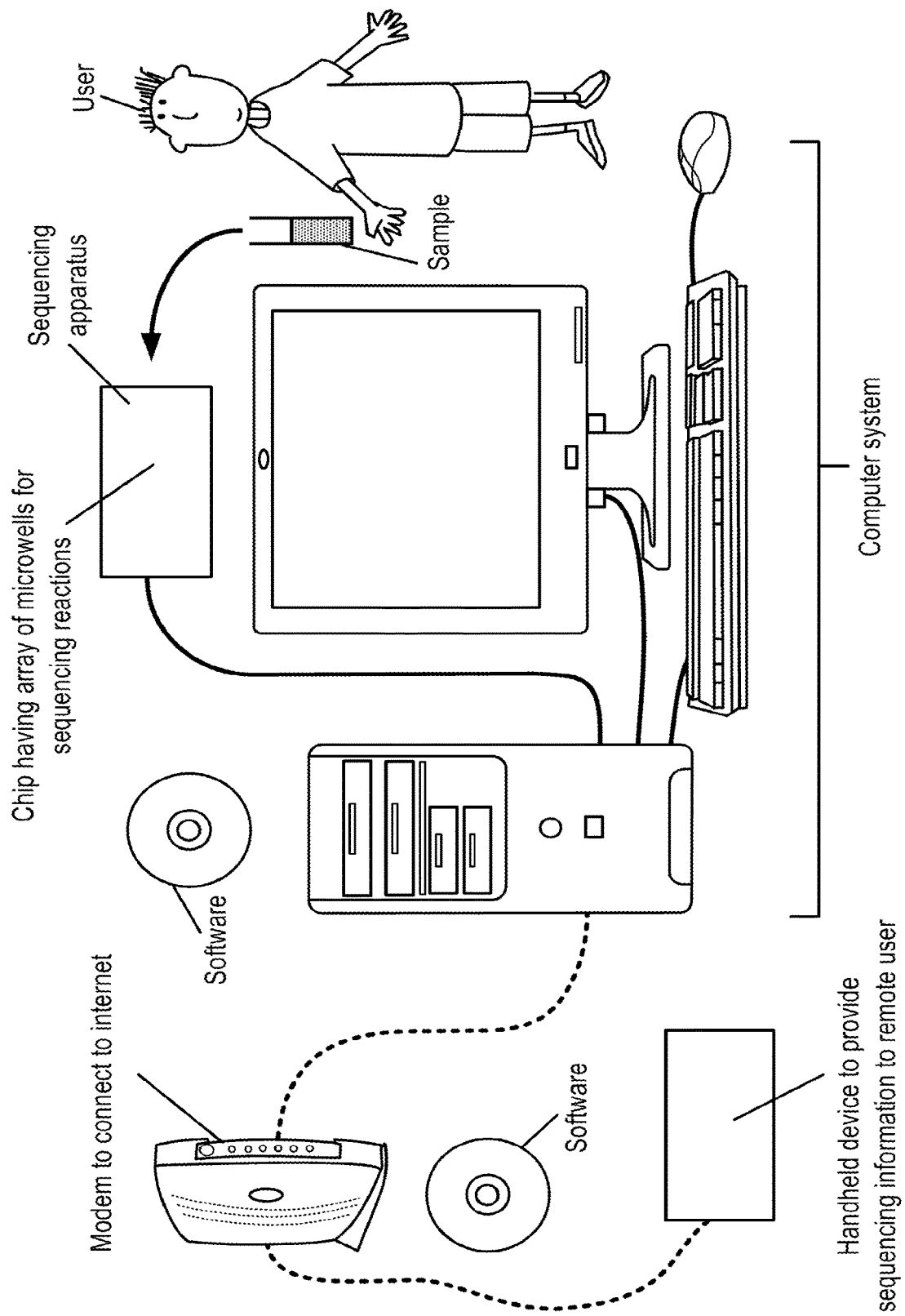
FIG. 11 depicts a computer readable stored media platform and example means for transmission of data s generated by the composition and methods of this disclosure

Another aspect of the invention provides a system that is configured to implement the methods of the disclosure. The system can include a computer server ("server") that is programmed to implement the methods described herein. FIG. 11 depicts a system adapted to enable a user to store, analyze, and process sequence information. The system includes a central computer server that is programmed to implement exemplary methods described herein. The server includes a central processing unit (CPU, also "processor") which can be a single core processor, a multi core processor, or plurality of processors for parallel processing. The server also includes memory (e.g. random access memory, read-only memory, flash memory); electronic storage unit (e.g. hard disk); communications interface (e.g. network adaptor) for communicating with one or more other systems; and peripheral devices which may include cache, other memory, data storage, and/or electronic display adaptors. The memory, storage unit, interface, and peripheral devices can be in communication with the processor through a communications bus (solid lines), such as a motherboard. The storage unit can be a data storage unit for storing data. The server is operatively coupled to a computer network ("network") with the aid of the communications interface. The network can be the Internet, an intranet and/or an extranet, an intranet and/or extranet that is in communication with the Internet, a telecommunication or data network. The network in some cases, with the aid of the server, can implement a peer-to-peer network, which may enable devices coupled to the server to behave as a client or a server. In some embodiments, the computing resources can be configured into a cloud-service model.

The storage unit can store files, such as sequence data, sample data, molecular barcodes, software, or any aspect of data associated with the invention. The data storage unit may be coupled with data that can bin sample sequence with the sample source or other information contained in a molecular barcode.

The server can communicate with one or more remote computer systems through the network. The one or more remote computer systems may be, for example, personal computers, laptops, tablets, telephones, smart phones, or personal digital assistants. The remote computer systems may, for example, be used to transmit patient data to a caregiver. The data or hardware or system, for example, may be encrypted or modified (e.g. to comply with HIPPA rules and standards).

In some situations the system includes a single server. In other situations, the system includes multiple servers in communication with one another through an intranet, extranet and/or the Internet.

The server can be adapted to store sample information, such as, for example, sample source, date, orientation, sequence, statistical data, or any other information of potential relevance. Such information can be stored on the storage unit or the server and such data can be transmitted through a network.

Methods as described herein can be implemented by way of machine (or computer processor) executable code (or software) stored on an electronic storage location of the server, such as, for example, on the memory, or electronic storage unit. During use, the code can be executed by the processor. In some cases, the code can be retrieved from the storage unit and stored on the memory for ready access by the processor. In some situations, the electronic storage unit can be precluded, and machine-executable instructions are stored on memory. Alternatively, the code can be executed on a second computer system.

Aspects of the systems and methods provided herein, such as the server, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

The results of sequencing can be presented to a user with the aid of a user interface, such as a graphical user interface.

V. Patient Care

The targeted sequencing technology may be used in sequencing of subjects in research or clinical settings. In an exemplary embodiment, the sequencing of one or more known disease causing genes can be done in a clinical setting for carrier screening. Clinical testing panels may be developed and potentially a targeted sequencing panel including interpretable locations in the genome. The technology can also be used to pick up mobile elements such as viral insertion sites or be used to identify SNPs, mutations, allelic variation or genetic modifications.

The invention described herein can provide data that can be used for a medical professional or caregiver to make care giving decisions. In some embodiments, the identification of one or more alleles, gene variants, SNPs or other genomic modifications can identify an animal, including a human, as a disease carrier. The patient status as a disease carrier can direct patient care, fertility decisions, prognosis, theranosis, monitoring, diagnosis and/or treatment of a patient or subject.

Diagnoses can comprise determining the condition of a patient. Diagnosis can be conducted at one time point or on an ongoing basis. For example, a patient can be diagnosed as being infected with a virus based on identification of viral insertion points in genomic DNA. A patient can be diagnosed with a condition based on the presence or absence of a genetic sequence.

A patient can be identified as a carrier for an autosomal recessive mutation or allele or chromosomal variant. A patient's status as a carrier can affect the patient's contraceptive choices, the patient's choices for preventative care, or the like. In some cases, carrier testing can be performed on individuals. Fertility and/or contraceptive decisions may be made based on the carrier status of an individual or couple. In some cases, measurement of fetal samples (e.g. prenatal testing) can influence treatment decisions for the mother or fetus.

Prognosis can comprise determining the outcome of a patient's disease, the chance of recovery, or how the disease will progress. For example, identifying chromosomal abnormalities can provide information upon which a prognosis may be based. For example, the presence or absences of a chromosomal variant may predict a cancer survival rate.

Monitoring can comprise the serial testing of a patient to determine the presence of a disease or to monitor the disease progression. For example, an individual who has been infected by a virus can undergo serial monitoring to determine if antiviral treatments are preventing the further infection of the individual.

Theranosis can comprise determining a therapy treatment. For example, a patient's therapy treatment can be determined, in part or in whole, based on the presence or absence of certain genomic elements. For example, the presence or absence of certain genomic variants within an individual's cytochrome p450 genes may affect drug metabolism rates and therefore can affect the type of treatment for an individual.

Clinical testing can be done using the methods described herein. In some instances, one or more protocols may be developed to comply with Clinical Laboratory Improvement Amendments (CLIA) or Food and Drug Administration (FDA) regulations.

VI. Clinical or Laboratory Research

Methods, kits and/or compositions may be used in clinical or laboratory research settings to study the genetic basis of disease, e.g. identify new genetic variations that can contribute to disease, likelihood of disease, or other conditions. Methods can be used to study viral infection, vaccine effectiveness. Methods, kits and/or compositions can be used to study regions of the genome that have traditionally been difficult to accurately sequence, such as highly polymorphic or variable regions within the genome.

VII. Kits

The reagents for carrying out the methods and assays of the present invention are optionally provided in a kit form to facilitate the application of these assays for the user. Such kits also typically include instructions for carrying out the subject assay, and may optionally include the fluid receptacle, e.g., the cuvette, multiwell plate, microfluidic device, etc. in which the reaction is to be carried out.

These kit reagents of the disclosure may be provided in vials for measuring by the user, or in pre-measured vials or ampoules which are simply combined to yield an appropriate reaction mixture. The reagents may be provided in liquid and/or lyophilized form and may optionally include appropriate buffer solutions for dilution and/or rehydration of the reagents. Generally, all of the reagents and instructions are co-packaged in a single box, pouch or the like that is ready for use.

VIII. Target Genes

The methods provided herein can be used to target all or a part of a disease related gene. For example nucleic acids containing a genes or gene segment related to one or more of the following diseases can be processed from a sample using the disclosed methods: ABCC8-Related Hyperinsulinism, Achromatopsia, Alkaptonuria, Alpha-1 Antitrypsin Deficiency, Alpha-Mannosidosis, Andermann Syndrome, ARSACS, Aspartylglycosaminuria, Ataxia With Vitamin E Deficiency, Ataxia-Telangiectasia, Autosomal Recessive Polycystic Kidney Disease, Bardet-Biedl Syndrome, BBS1-Related, Bardet-Biedl Syndrome, BBS10-Related, Biotinidase Deficiency, Bloom Syndrome, Canavan Disease, Carnitine Palmitoyltransferase IA Deficiency, Carnitine Palmitoyltransferase II Deficiency, Cartilage-Hair Hypoplasia, Choroideremia, Citrullinemia Type 1, CLN3-Related Neuronal Ceroid Lipofuscinosis, CLN5-Related Neuronal Ceroid Lipofuscinosis, Cohen Syndrome, Congenital Disorder of Glycosylation Type Ia, Congenital Disorder of Glycosylation Type Ib, Congenital Finnish Nephrosis, Costeff Optic Atrophy Syndrome, Cystic Fibrosis, Cystinosis, D-Bifunctional Protein Deficiency, Factor V Leiden Thrombophilia, Factor XI Deficiency, Familial Dysautonomia, Familial Mediterranean Fever, Fanconi Anemia Type C, Fragile X Syndrome, Galactosemia, Gaucher Disease, GJB2-Related DFNB 1 Nonsyndromic Hearing Loss and Deafness, Glucose-6-Phosphate Dehydrogenase Deficiency, Glutaric Acidemia Type 1, Glycogen Storage Disease Type Ia, Glycogen Storage Disease Type Ib, Glycogen Storage Disease Type III, Glycogen Storage Disease Type V, GRACILE Syndrome, Hb Beta Chain-Related Hemoglobinopathy (Including Beta Thalassemia and Sickle Cell Disease), Hereditary Fructose Intolerance, Hereditary Thymine-Uraciluria, Herlitz Junctional Epidermolysis Bullosa (LAMA3-Related), Herlitz Junctional Epidermolysis Bullosa (LAMB3-Related), Herlitz Junctional Epidermolysis Bullosa (LAMC2-Related), Hexosaminidase A Deficiency (Including Tay-Sachs Disease), HFE-Associated Hereditary Hemochromatosis, Homocystinuria Caused by Cystathionine Beta-Synthase Deficiency, Hurler Syndrome, Hypophosphatasia (Autosomal Recessive), Inclusion Body Myopathy 2, Isovaleric Acidemia, Joubert Syndrome 2, Krabbe Disease, Limb-Girdle Muscular Dystrophy Type 2D, Limb-Girdle Muscular Dystrophy Type 2E, Lipoamide Dehydrogenase Deficiency, Long Chain 3-Hydroxyacyl-CoA Dehydrogenase Deficiency, Maple Syrup Urine Disease Type 1B, Medium Chain Acyl-CoA Dehydrogenase Deficiency, Megalencephalic Leukoencephalopathy With Subcortical Cysts, Metachromatic Leukodystrophy, MTHFR Deficiency, Mucolipidosis IV, Muscle-Eye-Brain Disease, NEB-Related Nemaline Myopathy, Niemann-Pick Disease Type C, Niemann-Pick Disease (SMPD1-Associated), Nijmegen Breakage Syndrome, Northern Epilepsy, Pendred Syndrome, PEX1-Related Zellweger Syndrome Spectrum, Phenylalanine Hydroxylase Deficiency, Polyglandular Autoimmune Syndrome Type 1, Pompe Disease, PPT1-Related Neuronal Ceroid Lipofuscinosis, Primary Carnitine Deficiency, Primary Hyperoxaluria Type 1, Primary Hyperoxaluria Type 2, PROP1-Related Combined Pituitary Hormone Deficiency, Prothrombin Thrombophilia, Pseudocholinesterase Deficiency, Pycnodysostosis, Rhizomelic Chondrodysplasia Punctata Type 1, Salla Disease, Segawa Syndrome, Short Chain Acyl-CoA Dehydrogenase Deficiency, Sjogren-Larsson Syndrome, Smith-Lemli-Opitz Syndrome, Spinal Muscular Atrophy, Steroid-Resistant Nephrotic Syndrome, Sulfate Transporter-Related Osteochondrodysplasia, TPP1-Related Neuronal Ceroid Lipofuscinosis, Tyrosinemia Type I, Usher Syndrome Type 1F, Usher Syndrome Type 3, Very Long Chain Acyl-CoA Dehydrogenase Deficiency (Wilson Disease), and X-Linked Juvenile Retinoschisis.

The disease can be a cancer. Cancer can be, e.g., a tumor, a leukemia such as acute leukemia, acute t-cell leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, or chronic lymphocytic leukemia, polycythemia vera, lymphomas such as Hodgkin's lymphoma, follicular lymphoma or non-Hodgkin's lymphoma, multiple myeloma, Waldenstrom's macroglobulinemia, heavy chain disease, solid tumors, sarcomas, carcinomas such as, e.g., fibrosarcoma, myxosarcoma, liposarcoma, chondrosarcoma, osteogenic sarcoma, lymphangiosarcoma, mesothelioma, Ewing's tumor, leiomyosarcoma, rhabdomyosarcoma, colon carcinoma, colorectal cancer, pancreatic cancer, breast cancer, ovarian cancer, prostate cancer, including castration resistant prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic, carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, craniopharyngioma, ependymoma, pinealoma, hemangioblastoma, acoustic neuroma, oligodendroglioma, meningioma, melanoma, neuroblastoma, retinoblastoma, endometrial cancer, non small cell lung cancer, head and neck cancer, or kidney cancer.

The disease can be an autoimmune disease. The autoimmune disease can be a disease or disorder arising from and directed against an individual's own tissues or a co-segregate or manifestation thereof or resulting condition therefrom. Examples of autoimmune diseases or disorders include, but are not limited to: Acute Disseminated Encephalomyelitis (ADEM), Arthritis, Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO)-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, mixed cryoglobulinemia, neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Glomerulonephritis, Goodpasture's syndrome, Granulomatosis with Polyangiitis (GPA), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Insulin-dependent diabetes (type1), Interstitial cystitis, Juvenile arthritis, Type I diabetes, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, or III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, and Wegener's granulomatosis.

The methods provided herein can be used to prepare samples comprising genes or parts of genes related to cancer. For example, the methods provided herein can prepare samples for sequencing somatic mutations related to cancer. Somatic mutations related to cancer can be found, for example, in the COSMIC database maintained by the Wellcome Trust Sanger Institute, which is incorporated herein by reference.

X. PROPHETIC EXAMPLES

Example 1: Sample Protocol for mPEAR-Generated Libraries

Obtain input polynucleotide. Generally at least 50 ng of high molecular weight genomic DNA (gDNA). Fragment the gDNA.

Fragmentation:

Multiple fragmentation methods are suitable. Fragmentation by shearing can be used (e.g. Covaris). The mean fragment size can be approximately 100, 200, 300, 400 or more nucleotides but may vary depending on sequencer platform used. The fragment size can be greater for third generation sequencing technology.

Re-suspend DNA in 75 µL 1× Tris-EDTA (TE) buffer. Add resuspension mixture to glass Covaris tube. The following settings can be used: duty cycle 10%, intensity 5, cycles/burst 200, Time 120 s.

End Repair and Adaptor Ligation:

Blunt ends can be generated. A-tailing can be done for Illumina library generation. For other sequencing platforms, A-tailing may be optional.

End Repair

Add ligase buffer first to beads. Make master mix.

Prepare the following reaction mixture in a 0.5 mL low DNA binding tube:

| | |
|---|---|
| H₂0 | 75 µL |
| T4 DNA ligase buffer with 10 mM ATP | 10 µL |
| 10 mM dNTP mix | 4 µL |
| T4 DNA Polymerase | 5 µL |
| Klenow Fragment 5 U/µL | 1 µL |
| T4 Polynucleotide kinase | 5 µL |
| TOTAL: | 100 µL |

Resuspend the beads in a end repair mix. Incubate the samples in a heat block at 20° C. for 30 minutes. Place on magnetic particle consolidator (MPC) and remove supernatant. Using the MPC, wash the immobilized library 3 times with 200 µL of 1×SSC buffer, no tRNA. Mix well between each wash.

A-Tailing Mix:

Add buffer first to beads or make master mix. Prepare the following reaction mixture in a 0.5 mL low DNA binding tube:

| | |
|---|---|
| H₂0 | 32 µL |
| 10X buffer B011 | 5 µL |
| 1 mM dATP | 10 µL |
| Klenow Exo- | 3 µL |
| Total: | 50 µL |

Resuspend the beads in the A tailing mix. Incubate the samples in a heat block at 37° C. for 30 minutes. Place on MPC and remove supernatant. Using the MPC, wash the immobilized library 3 times with 200 µL 1×SSC with tRNA and 1 time with 1×SSC (1×=0.150 M Sodium Chloride, 0.015 M Sodium Citrate) buffer, no tRNA. Mix well between each wash.

Ligation:

Add 2× ligation buffer to beads. Resuspend the beads such that the final adaptor concentration is 0.3 µM. Dilute stock 1:10 with annealing solution. A different barcode adaptors can be used for 10, 15, and 20 cycles from above.

| | |
|---|---|
| dH20 | 18 µL |
| 2X Rapid Ligation Buffer (Enzymatics B101L) | 25 µL |
| TruSeq barcoded Adaptors (1:10 dilution bc10, 11, 12) | 3 µL |
| Total: | 45 µL |

Add 5 µL of T4 DNA Ligase (Rapid) and mix by pipetting up and down. Incubate the samples at 20° C. for 15 minutes, with mixing. Using magnet, wash the beads 3 times with 200 µL 1×SSC (with 10 ng/uL tRNA) and 1 times with 200 uL 1×SSC (no tRNA). Resuspend the beads in 23 µL H2O. Transfer to thin walled PCR tube, rinse tube with another 23 uL water.

PCR Enrichment:

This step may be optional.

Prepare the following PCR reaction mix in a 500 µL thin wall PCR tube

| | |
|---|---|
| Beads resuspended in H2O | 23 µL |
| 2× HiFi KAPA Master Mix | 50 µL |
| Truseq PCR primer 1 | 2 µL |
| Truseq PCR primer 2 | 2 µL |
| Nuclease water, from above | 23 µL |

Run the following PCR protocol 10 and 15 cycles:

45 sec at 98° C.

Remove 50 µL after 10 cycles then do 10 more cycles.

98° C., 15 s

60° C., 30 s

72° C., 30 s 1 min at 72° C.

Hold at 4° C.

Purify the DNA (e.g. with Zymo (25) PCR Purification Kit). Elute in 30 µL dH₂0. Purify 10 cycle and 20 cycle product on 4% agarose gel.

Example 2: Exemplary Adapter Design for mPEAR

Adaptor sequences can consist of a universal sequence at the 5' end, a 3 nucleotide sequence for directional information, and a 4 to 6 nucleotide molecular barcode at the 3' end. Incorporating molecular barcodes can allow for multiplexed target enrichment and sequencing. DNA samples can be individually fragmented, end repaired, and adaptors ligated. Because each sample can have a barcode, the mPEAR step may be multiplexed, dramatically reducing cost and increasing throughput by eliminating individual sample processing steps post library generation. mPEAR library generation with Genome RAPELLing is amenable to all sequencing platforms. Sequencer platform specific adaptors are incorporated through a low cycle PCR reaction after elution from streptavidin beads. Shorter adaptor sequences allow for greater ligation efficiency and more precise size selection of library molecules. Examples of suitable sequence are shown in FIG. 14

Example 3: mPEAR

Prepare libraries via 12 cycles PCR with barcoded samples. Transfer 30 µL DNA sample to 0.5 mL LoBind tubes. Add 1 nmol of each 3' blocked adaptor blocker oligonucleotides (10 µL each 100 µM, universal blocker 1, universal blocker 2, blocker 1, and blocker 2) and dry (e.g speedvac).

Resuspend:

| | |
|---|---|
| 5 µL 10X std. Taq buffer | (60%) 5X biotin-dNTP |
| 10 uL 10X 60% biotin-dNTP | 6.25 µL dA, dC, dG (20 mM) |
| 1 µL 60 primer mix (25 µM) | 15 µL bio-dUTP (5 mM) |
| 32 µL nuclease-free water | 2.5 µL dT (20 mM) |
| 1 µL 100 mM soln. MgCl₂ | 13.75 µL nH₂O |
| 1 µL Taq (5 U/µL) | 1 µL |
| Total: | 50 µL |

Heat to 98° C., for 2 minutes. Either slow cool using ramp on thermocycler to 47° C. or fast cool to 47° C., then hold at 47° C. for 4 minutes, then 72° C. fast ramp for 10 minutes, then add 1 µL of 0.5 M EDTA to quench. Place on ice.

```
Universal blocker 1:
GATCGGAAGAGCACACGTCTGAACTCCAGTCAC555555ATCTCGTATGC
CGTCTTCTGCTTGX Universal blocker 2:
CAAGCAGAAGACGGCATACGAGAT555555GTGACTGGAGTTCAGACGTG
TGCTCTTCCGATCX
```

Library Immobilization

Wash streptavidin beads (e.g. Dynal M280 Streptavidin beads) with: B&W-100 uL, 1M Tris, pH 7.5, 20 µL 0.5 M EDTA, 4 mL 5 M NaCl fill to 10 mL with nH$_2$0. Transfer 25 µL beads to a new 0.5 mL LoBind tube. Wash streptavidin magnetic beads with B&W buffer (with 10 ng/µL tRNA) 3 times, 200 µL each wash (pipette mixing). The last wash can be 5 minutes. Use a MPC, to pellet the beads and remove the buffer. Add 50 µL of B&W buffer (no tRNA). Transfer 50 µL of DNA to the 50 µL of Dynal M-280 streptavidin beads or vice versa can use an additional 20 µL B&W buffer to rinse tube. Mix well and incubate at room temperature, for 1 hour, mixing every 15 minutes. Using a magnet, wash the immobilized library 3 times with 200 µL of B&W buffer. Wash 2 times with 200 with 1×SSC. Transfer beads to PCR tube using last wash. Remove all remaining 1×SSC buffer of last wash. Beads should now be in PCR tube ready for amplification.

Enrich by PCR-15 and 25 cycles

| Add to beads: | 98° C., 45 sec-hold |
|---|---|
| 50 µL 2X HiFi KAPA ready mix | 98° C., 15 sec |
| 2 µL PCR 1 | 60° C., 30 sec |
| 2 µL PCR 2 | 72° C., 30 sec |
| 46 µL nH2O | 72° C., 60 sec-hold |
| 100 µL | 4° C.-hold |

Clean DNA (e.g. using Zymo-25 column). Elute with 30 uL and speedvac dry. Resuspend in 20 µL. Load onto 2% agarose gel and run with ladder. Cut out region from 320-400 nucleotides. Excised DNA can be processed and sequenced.

Data Analysis:

After standard data quality metrics are determined, sequence reads can be binned or associated by molecular barcode.

Anchored Read Alignment:

On target sequencer reads will contain the mPEAR primer-annealing site. The annealing site is used as an "anchor" to position the read in the genome. The sequence downstream of the "anchor" can be treated as de novo sequence. This is a significant advantage over shot-gun exome sequencing methods that require the read to be similar to the reference genome being used. Longer insertions and deletions are detected through de-novo sequencing but missed by resequencing as they are too divergent from the reference genome to be detected by most alignment methods. Translocations, viral insertion sites and other mobile elements that flank known mPEAR annealing sites are also detected through anchored read alignment.

Detached-Mate Pair Sequencing:

mPEAR allows for detached mate pair sequencing. Both strands are targeted with different mPEAR annealing sites. The annealing sites may be paired in silico. The overlap between the reads improves sequence quality and the distance between the mPEAR annealing sites may be used to determine copy number or chromosomal rearrangements. In some cases, both mPEAR annealing sites will be contained in a single read. This allows for the determination of long repetitive sequences such as the tandem tri-nucleotide repeat predictive of Fragile X syndrome. Longer target sequences may require multiple anchor alignment.

Example 3: Genotyping Diagnostics

TELA reactions are prepared on a human DNA sample (e.g a population of human skin cells, suspected of being cancerous). Cells can be lysed using detergent and heat and approximately 15,000 copies of diploid DNA are precipitated via cholorform/ethanol extraction. A resuspension of DNA can be collected with approximately 10,000 copies of haploid DNA. A library of 100 TELA primer sets can be applied to the sample of DNA. Primer sets within the library can contain locus specific sequences for various oncogenes and tumor suppressors known to be associated with skin cancers. Each primer also can contains a barcode sequence. Primer extension reactions are conducted with similar reaction conditions as described herein with Klenow fragment polymerase. Subsequent PCR amplification, using universal priming sites (via the TELA primers) and degenerate primers can increase barcoded DNA yields to 10 ng.

The sample can be sequenced to sufficient coverage (e.g. 500) using a multiplex sequencing strategy. Bar coding of individual DNA strands can allow for sequencing information to be gained from individual strands rather than as an average of entire sample of DNA. Based upon the number of DNA strands sequenced and bar codes assigned, SNP phasing/haplotyping information is gained and many repetitive regions of DNA can be resolved. In addition, a substantial boost in accuracy can be gained by discarding mutations that appear randomly with respect to haplotypes, as those are likely to be sequencing errors. SNP phasing/haplotyping information provides genetics clues to type of skin cancer that may exist in the cells. A report can be generated for a medical practitioner for follow-up and evaluation. Further, these reports can be submitted and accessed electronically via the internet. Analysis of sequence data occurs at a site other than the location of the subject. The report is generated and transmitted to the user/medical practitioner's location. Via an internet enabled computer, the medical practitioner accesses the reports reflecting the analysis of the suspected cancer as shown in FIG. 11.

Example 4: RAPELL Protocol

Add gDNA (e.g. human brain DNA), NEB4 buffer, nH$_2$0 and denature 10 min at 96° C.

1 µL human brain DNA (HBD) 50 ng
2 µL RAPELL 1 (10 µM)
2 µL RAPELL 2 (10 µM)
1.2 µL 10 mM dNTP
4 µL 10×NEB4 buffer
17.8 µL nH$_2$O
2 µL T4 DNA polymerase (no strand displacement)
2 µL DNA ligase (600 U/µL)
3.6 µL 10 mM ATP
35.6 µL reaction.

Incubate 20° C. for 0.5 hour. Denature 96° C. for 2 minutes. Add 2 µL T4 DNA polymerase. Add2 µL DNA ligase. Incubate at 20° C. for 0.5 hours. Cycle 5 times between heat denature and adding enzymes, 2nd cycle add 2 µL 10×NEB4 buffer. Incubate at 75° C. for 20 minutes to kill enzymes.

Use 53.6 µL from above. Add the following:
6 µL UDG
6 µL APE
Total: 65.6 µL

Incubate 37° C. for 1 hour. Clean DNA (e.g. Zymo-5 clean-up, with 5 vol DNA bind buffer (320 uL)). Elute with 20 µL elutant.

| PCR between 15 and 25 cycles | Cycling |
|---|---|
| 20 µL DNA from above | 98° C., 45 s |
| 2 µL PCR1 (25 µM) | 98° C., 15 s |
| 2 µL PCR2 (25 µM) | 60° C., 30 s |
| 50 µL 2X HiFi KAPA mix | 72° C., 30 s |
| 26 µL nH$_2$O | 72° C., 60 s |
| 100 µL | 4° C.-hold |

Clean DNA (e.g. Zymo—25 clean up). Elute with 30 µL elutant and dry (e.g. with speedvac). Run on 2% agarose gel. Excise DNA for further processing, sequencing and data analysis.

Example 5: Exemplary Oligonucleotides for RAPELLing

FIG. 18 discloses exemplary oligonucleotides that can be used to perform the methods of the invention.

Example 6

Sample method of obtaining long fragment sequencing reads with mPEAR-generated libraries. Polynucleotide is obtained from a source. The polynucleotide is fragmented, end repaired, and subjected to mPEAR-mediated generation of an amplified target library. The target library is then subjected to the method of RAPELLing where the target library is fragmented into long polynucleotide fragments and subjected to partitioning, copying, amplifying, and sequencing. A consensus sequence is then assembled.

Example 7

1. Primer design: A tiling strategy can be used for comprehensive coverage of targeted loci. Starting from 100-200 nucleotides upstream of the target loci and continuing through the loci to extend 100-200 nucleotides past the loci. The target can be broken up into 100-200 nucleotide windows wherein the best performing primer or primers are chosen. Primers can be variable in length. Primers can be optimized to account for an optimal Tm. Primers can be designed for maximum specificity to the target location. Primers can be designed to avoid dimerization. The 5' end of the primer can be "tailed" with a sequence corresponding to the sequencer platform used in the reaction. This sequence can be referred to as an "A adapter". The primer can be referred to as an "A adapter tailed primer". Primers can have a 3'OH group that can be extended by polymerase.

2. Addition of an A adapter: an A adapter tailed primers can hybridize to genomic DNA ("gDNA"). A strand displacing thermostable polymerase can used to extend. Extension can occur in the 5'-3' direction. A copy of the template DNA can be made by the polymerase while displacing any DNA strands that are already hybridized to the template. The process can be repeated or cycled by heat denaturing, primer annealing and primer extension. Only the forward strand is copied in this manner 3. Fragmentation: Fragmentation of the amplified products can be accomplished by enzymatic or physical means to generate random three prime ends. The preferred method for generating random 3' ends is to incorporate a biotinylated ddNTP by using a low ratio of biotin ddNTP/dNTP in the primer extension reaction. The ddNTPs can randomly terminate the extended molecule. Other fragmentation methods can include shearing such as with sonication or enzymatic fragmentation. By using a biotinylated ddNTP, the biotinylated molecules can be isolated by streptavidin bead purification.

4. Addition of B adapter: a B adapter can be added for sequencing reactions. If enzymatic or physical fragmentation is used, the B adapter can be added by ligation or an additional primer extension step. When terminating ddNTP is used for fragment generation in the previous step, the 3' end of the molecule is not available for primer extension or ligation due to the lack of a 3' OH. In this instance a B adapter can be added by hybridizing a random primer with the B adapter tail on or near the 5' end of the isolated molecule. In one non limiting example, the random primer can comprise: 5'-B adapter-NNNN . . . -3' wherein "NNNN" is representative of a random nucleic acid sequence of one or more nucleotides. The random segment of the primer can hybridize along the captured molecule. A strand displacing polymerase can be used to extend. The extension can occur in the 5' to 3'direction. The random primer at the end of the biotinylated template can extend and displace all other primers. After extending and displacing, it can be the only molecule remaining on the biotinylated template. The double stranded complex can consist of a strand containing a 5' A adapter-locus specific primer-target-terminating ddNTP-biotin 3'. The reverse strand can contain 5'-B adapter-random sequence-target-locus specific sequence-A Adapter-3'. The complex can again be isolated by washing the streptavidin beads and removing the supernatant.

5. Release: The complex with both an A adapter and a B adapter can be released from the beads by heat denaturation. 9-12 cycles of PCR is performed with primers complimentary to the A and B adapter sequences. If they have not already been incorporated, a full length sequencing adapters can be incorporated during the PCR step by using tailed primers.

Optionally, molecular barcodes for sample multiplex during sequencing can be added with the original A adapter primer extension, the B adapter primer extension, and/or during the final PCR amplification.

6. Sequencer ready library: the resulting sequencer ready library can consist of double stranded molecules in the following format: 5'-A adapter-synthetic primer-target-random end of target-b adapter-3'. The library can be sequenced and the data can be stored and/or transmitted for analysis.

7. Data analysis: during data analysis the adapters can be trimmed off of the reads. Samples can be identified based on any optional barcodes. Duplicate reads can be removed. Genomic coordinates can be identified by the known synthetic sequence at the beginning of the read. Reads corresponding to the same known genomic coordinate can be binned together. A consensus sequence can be generated without the use of a reference genome. Reads that do not form a consensus can be removed from analysis as off target. Each contiguous segment of target DNA can be considered a singular target and all primers corresponding to that target can be considered that targets primer set. This can produce an in silico read length that can be equivalent to the full length of the target. Generation of an in silico read length can be performed regardless of target size. After consensus sequence is determined, haplotypes for the target region can queried. For consensus sequences that do not match a known haplotype, the de novo sequence can be used to determine novel haplotypes and/or structural variation.

8. Use: the technology may be used in clinical sequencing of known disease causing genes such as carrier testing. Other testing panels may be developed and potentially a targeted sequencing panel including interpretable locations in the genome. In addition, because the sequencing can go from known to unknown, the technology can be used to identify viral insertion sites.

Example 8

1. Primer design: multiple primers can be designed to hybridize to specific target sequences within or nearby a selected target region. The spacing of each primer can be variable. The variable spacing can result in a high level of coverage along the entire length of the selected target region.

2. Addition of an A adapter: the single direction primers also can contain a 5' sequence specific for the sequencing platform to be used (e.g. "A" adapter sequence on 5' end).

3. Elongation: a primer mix is hybridized to target DNA and extended with a polymerase using a mix of dNTPs spiked with a low concentration of dUTP.

4. Size-control/fragmentation: extended primers can be cut to generate a nested set of single stranded products. One non-limiting example of a way to cut is to use uracil DNA glycosolase ("UDG") and/or human apurinic/apyrimidinic endonuclease I (APE I) to generate nested set of single stranded products. These products can be anchored at the 5' end by the A adapter sequence. An alternative fragmentation strategy could use a mix of dNTPs spiked with a low concentration of methyl-dCTP followed by restriction enzyme digest with a four base cutter that will not cut sites with methyl-C incorporated.

5. Addition of a B adapter: a B sequencing adapter is can be added to the 3' end by ligation or primer extension using a double stranded construct containing the B sequencing adapter with a 5'-random base overhang. After the B adapter is added, the library can be PCR amplified using A and B specific PCR primers. If the adapters that have been added are not full length, full length adapters can be added through primer tails.

Optionally, molecular barcodes for sample multiplex during sequencing can be added with the original A adapter primer extension, the B adapter primer extension, and/or during the final PCR amplification.

6. Sequencer ready library: the resulting sequencer ready library can consist of double stranded molecules in the following format: 5'-A adapter-synthetic primer-target-random end of target-b adapter-3'. The library can be sequenced and the data can be stored and/or transmitted for analysis.

7. Data analysis: during data analysis the adapters can be trimmed off of the reads. Samples can be identified based on any optional barcodes. Duplicate reads can be removed. Genomic coordinates can be identified by the known synthetic sequence at the beginning of the read. Reads corresponding to the same known genomic coordinate can be binned together. A consensus sequence can be generated without the use of a reference genome. Reads that do not form a consensus can be removed from analysis as off target. Each contiguous segment of target DNA can be considered a singular target and all primers corresponding to that target can be considered that targets primer set. This can produce an in silico read length that can be equivalent to the full length of the target. Generation of an in silico read length can be performed regardless of target size. After consensus sequence is determined, haplotypes for the target region can queried. For consensus sequences that do not match a known haplotype, the de novo sequence can be used to determine novel haplotypes and/or structural variation.

8. Use: the technology may be used in clinical sequencing setting. One non-limiting example is to test for alleles that are known to be associated with disease, e.g. carrier testing. Other testing panels may be developed and potentially a targeted sequencing panel including interpretable locations in the genome. In addition, because the sequencing can go from known to unknown, the technology can be used to identify viral insertion sites. Because this targeted method provides sequence alignment location while also allowing de novo assembly of reads, and because the target is sequenced by primer extension and not based on purification or recognition by hybridization, it can enrich for sequencing libraries that contain insertions, deletions, and/or other genetic anomalies that other hybridization based target capture methods have difficulty retaining. In one non-limiting example, this approach can be particularly suitable sequencing the Human Histocompatibility Antigen (HLA) region.

This method also describes a useful method for targeted, semi-targeted, and whole genome amplification procedures including whole genome phasing. In the case of whole genome phasing the strategy would be to start by a highly diluted, sub-genomic quantity of DNA in multiple reactions. The DNA could be in relatively large fragment (e.g. 10-40 kb). In this iteration of the protocol, the majority of the sequence generated in each reaction is derived from a single copy of the subject's genome and thus, the majority of detected variations could be homozygous.

Example 9

1. Library preparation: a library can be prepared using platform-specific library preparation method or kit. The method or kit can be commercially available and can generate a sequencer-ready library. Platform-specific library preparation methods can add a known sequence to the end of nucleic acid molecules; the known sequence can be referred to as an adapter sequence. Optionally, the library preparation method can incorporate one or more molecular barcodes.

2. Targeting: DNA molecules from the sequencer-ready library can be selected (i.e. targeted) using a pool of one or more primers (i.e. mPEAR primers). A mPEAR primer can hybridize to a target library molecule or fragment. The hybridized mPEAR primers can be extended using a polymerase. mPEAR primer can comprise a universal or common 5' end, a spacer sequence, and a target or locus-specific sequence. The universal or common end can hybridize to the universal adapter sequences from the previous library generation step. This can serve to stabilize the synthetic oligonucleotides toward the end of DNA library fragments. Stabilization toward the end of the library fragments can allow the sequencer read to appropriately position the target sequence without wasted sequencer capacity. The spacer sequence can comprise a variable number of degenerate nucleotides. The degenerate nucleotides allow for length flexibility in the DNA library start and stop positions during DNA sequencing. Having variable sequence start sites can reduce systematic errors in the sequencing step. Having variable sequence start sites can allows for a randomized error profile across the reads of the redundant DNA library fragments. Finally, a locus-specific binding site localized near the three prime end of the mPEAR primer. The locus specific priming site is designed to recognize a DNA sequence that is upstream of the actual target sequence. One or more mPEAR primers can be used in tandem to target one or more regions of interest. Targeting sequences upstream of the target allows for increased specificity as pseudogenes and gene families with similar sequence homology can be avoided, reducing false positives in the data. Optionally, a second mPEAR primer can be designed to bind to the opposite strand. Optionally, the mPEAR primer can incorporate a molecular barcode.

2. Extension: the 3' end of the mPEAR primer can be available for primer extension. A polymerase can be used to extend the molecule. The extension can occur in a 5' to 3' direction. Biotinylated dNTPs can be incorporated (i.e. a mixture of native and biotinylated dNTPs can be used in the extension reaction). Optionally, the mPEAR primer extension can occur on both strands. The mPEAR primer extension can run through the end of the DNA library molecules. The optional use of a mPEAR primer extension occuring on both strands of DNA can be advantageous; having two reactions targeting the same sequence can increase specificity and/or can reduce failures (e.g. if one of the mPEAR primers were to fail, for example, by not hybridizing).

3. Separation: the newly synthesized, biotinylated, DNA library/capture molecule hybrid can be incubated with streptavidin (e.g. streptavidin coated magnetic beads). The target, biotinylated DNA molecules can be isolated through magnetic bead purification. One or more washes can be performed with a suitable buffer. Optionally, DNA library molecules can be eluted from the capture molecules. Alternatively, an amplification reaction can be performed while the magnetic beads are still in solution (i.e. with no elution steo). Amplification can occur through PCR with the appropriate primers. During PCR amplification, full length sequencing platform specific adapter sequences can be incorporated. The resulting amplified molecules can be sequencer-ready or can be further purified through any means known in the art before sequencing).

4. Sequencing: The library can be sequenced and the data can be stored and/or transmitted for analysis.

5. Data analysis: during data analysis the adapters can be trimmed off of the reads. Samples can be identified based on any optional barcodes. Duplicate reads can be removed. Genomic coordinates can be identified by the known synthetic sequence at the beginning of the read. Reads corresponding to the same known genomic coordinate can be binned together. A consensus sequence can be generated without the use of a reference genome. Reads that do not form a consensus can be removed from analysis as off target. The read structure of the captured molecules can have significant advantages in speed and quality of data analysis. Because the locus specific primer recognition site is upstream of the target DNA sequence, that locus specific site is used to identify the genomic location of the read. A reference genome is not strictly needed; by "seeding" the read with the known sequence, the remainder can be assembled without the use of a reference genome. True de novo sequencing of the DNA targets can be accomplished. De novo sequencing can allow for greater sensitivity of genomic loci that greatly differ from the reference genome. Detection of longer insertions, deletions, repeats that are clinically relevant, and potentially viral insertion sites or mobile elements that disrupt gene function are detected with greater sensitivity. No reference score, or similarity to the reference is strictly needed to measure quality.

Example 10

1. Primer Design: primers can be designed upstream of the target sequence or loci. A first primer can comprise: a locus specific sequence and a 5' sequence wherein the 5' sequence can comprise all or part of a first adapter sequence of the sequencing platform being used (i.e. a TELA primer). A second primer (i.e. "a probe") can comprise: a random sequence consisting of 8 nucleotides and a 3' sequence, wherein the 3' sequence comprises all or part of a second adapter sequence of the sequencing platform being used (i.e. a TELA probe).

2. Hybridization: the TELA primer can hybridize to a specific sequence. The specific sequence can be near the loci of interest. In some embodiments, the specific sequence can be just outside the loci of interest. The TELA probe can hybridize to random sequences across the entire genome. The spacing of the TELA probe hybridization can be adjusted by adjusting TELA probe concentration. The TELA primer and the TELA probe can hybridize to the same template strand.

3. Elongation: a non-displacing polymerase can be used to extend the first primer until it reaches the second primer on the DNA template. A DNA ligase can join (i.e. connect or ligate) the TELA primer to the TELA probe. The resulting product can consists of a single stranded copy of the DNA template flanked by adapter tails.

4. Amplification: PCR can be used to amplify the product. In cases where the product does not contain complete (i.e. full length) adapter sequences, tailed primer amplification can incorporate the remainder of the first and second sequencer adapters (i.e. sometimes referred to as an A adapter and a B adapter). The amplification can produce a sequencer-ready library. Optionally, the product can be purified or further processed to be sequencer-ready.

Optionally, one or more molecular barcodes can be added with the TELA primer, the TELA probe and/or during the final PCR tailed amplification.

5. Sequencing: the library can be sequenced and the data can be stored and/or transmitted for analysis.

6. Data analysis: the data from sequencing can be analyzed. An advantage of this approach includes the ability to determine the genomic position of the sequencer read from the synthetic sequence at the beginning of each read. In addition, clonal errors can be avoided or reduced because the 3' end of the sequencer read is randomly generated (i.e. through the randomly binding TELA probe). If a variant is detected from multiple sequencer reads with different 3' ends, it is likely a true, or genomic, variant as opposed to a sequencer or read variant. If an error occurs during amplification, it may only appear in reads with the same 3' end.

Example 11

Sequencing libraries were prepped according to standard library preparation methods. Two samples were barcoded with Truseq barcodes #5 and #6.

Sample A was prepared by: fragmentation (i.e. shearing) using the Covaris shearing method. The fragmented sample was: end-repaired, A-tailed, and adapter ligated. Then magnetic bead purification 2 times-index 5, took all of prepped sample into protocol.

Sample B: Fragmented on covaris, end-repaired, A-tailed, and adapter ligated then magnetic bead purification 2 times, then PCR cycled this material 12 times, then magnetic bead purified before being purified further on 2% agarose gel, bands at approx. 350-420 bp were cut, excised, and isolated by agarose dissolving buffer and zymo-25 column-index 6, approx. 200 ng input Transfer all of DNA sample to 0.5 mL LoBind tube (Eppendorf). Add 1 nano mole of each 3' blocked adapter blocker oligos. (10 uL each 100 uM, universal blocker 1, universal blocker 2, blocker 1, and blocker 2). Speedvac dry and resuspend.

| | |
|---|---|
| 5 µL 10X standard Taq buffer | (60%) 5X biotin-dNTP |
| 10 µL 10X 60% biotin-dNTP | 6.25 µL dA, dC, dG (20 mM) |
| 1 µL 60 primer mix (25 µM) | 15 µl bio-dUTP (5 mM) |
| 32 µL nuclease-free water | 2.5 µL dT (20 mM) |
| 1 µL 100 mM solution MgCl$_2$ | 13.75 uL nH$_2$O |
| 1 µL Taq (5 U/µL) | |
| TOTAL: | 50 uL |

Heat to 98° C., for 2 minutes. Slow cool using ramp on thermocycler to 47° C. then to 72° C. for 10 minutes, then add 1 µL of 0.5 M EDTA to quench and place on ice.

Library Immobilization

Wash Dynal M280 Streptavidin beads (B&W-100 µL, 1M Tris pH7.5, 20 µL 0.5 M EDTA, 4 mL 5 M NaC up to 10 mL with nH$_2$O). Transfer 250 µL beads to a new 0.5 mL LoBind tube. Wash streptavidin magnetic beads with B&W buffer (with 10 ng/uL tRNA), 3 times, 200 µL each wash (pipette mixing). Last wash wait 5 minutes before removing. (Use a MPC, to pellet the beads and remove the buffer). Add 50 µL of B&W buffer (no tRNA). Transfer 50 µL of DNA to the 50 µL of Dynal M-280 streptavidin beads or vice versa (can use an additional 20 µL B&W buffer to rinse tube). Mix well and incubate at room temperature, for 1 hour, mixing every 15 minutes. Using magnet, wash the immobilized library 3 times with 200 µL of B&W buffer and 2 times with 200 µL wash with 1× saline sodium citrate (SSC). Transfer beads to PCR tube using last wash. Remove all remaining 1×SSC buffer of last wash. Beads should now be in PCR tube ready for amplification.

Enrich by PCR: between 15 and 25 cycles (take out 50 µL at 15 cycles and let rest finish to 25 cycles).

| | Cycles |
|---|---|
| Add to beads: | 98° C., 45 sec-hold |
| 50 µL 2X HiFi KAPA ready mix (KAPA Biosystems | 98° C., 15 sec |
| 2 µL PCR 1 | 60° C., 30 sec |
| 2 µL PCR 2 | 72° C., 30 sec |
| 2 µL PCR nH$_2$O | 72° C., 60 sec-hold |
| 100 µL | 4° C.-hold |

Clean DNA (e.g. Zymo-25 column), elute with 30 µL elutants, speedvac dry, resuspend 20 µL load onto 2% agarose gel. Cut 320-400 nucleotides band. The material cycled 25 times produced enough DNA product for sequencing. Amplified DNA was purified on 2% agarose and bands at approximately 350-420 nucleotides were cut, excised, and isolated by agarose dissolving buffer and zymo-25 column.

Example 12

Libraries were prepped: (12 cycles PCR). Two samples barcode 5,735 ng and barcode 6, 684 ng. Transfer 30 µL DNA sample to 0.5 mL LoBind tube. Add 1 nmol of each 3' blocked adapter blocker oligonucleotides. (10 µL each 100 µM, universal blocker 1, universal blocker 2, blocker 1, and blocker 2). Speedvac dry.

Resuspend:

| | |
|---|---|
| 5 µL 10X std. Taq buffer | (60%) 5X biotin-dNTP |
| 10 µL 10X 60% biotin-dNTP | 6.25 µL dA, dC, dG (20 mM) |
| 1 µL 60 primer mix (25 uM) | 15 µl bio-dUTP (5 mM) |
| 32 µL nuclease-free water | 2.5 µL dT (20 mM) |
| 1 µL 100 mM soln. MgCl2 | 13.75 µL nH$_2$O |
| 1 µL Taq (5 U/uL) | |
| Total: 50 µL | |

Heat to 98° C., for 2 minutes. Either slow cool using ramp on thermocycler to 47° C. or fast cool to 47° C., then hold at 47° C. for 4 minutes, then 72° C. fast ramp for 10 minutes, then add 1 µL of 0.5 M EDTA to quench. And place on ice.

Library Immobilization

Wash Dynal M280 Streptavidin Beads:

(B&W-100 uL, 1M Tris pH7.5, 20 uL 0.5 M EDTA, 4 mL 5 M NaCl . . . up to 10 mL with n-water). Transfer 25 µL beads to a new 0.5 mL LoBind micro centrifuge tube. Wash streptavidin magnetic beads with B&W buffer (with 10 ng/uL tRNA), 3 times, 200 µL each wash (pipette mixing). Last wash wait 5 minutes before removing. Use a MPC, to pellet the beads and remove the buffer. Add 50 µL of B&W buffer (no tRNA). Transfer 50 µL of DNA to the 50 µL of Dynal M-280 streptavidin beads or vice versa. An additional 20 µL B&W buffer can be used to rinse tube. Mix well and incubate at room temperature, for 1 hour, mixing every 15 minutes. Using magnet, wash the immobilized library 3 times with 200 µL of B&W buffer and 2 times with 200 µL wash with 1×SSC. Transfer beads to PCR tube using last wash. Remove all remaining 1×SSC buffer of last wash. Beads should now be in PCR tube ready for amplification.

Enrich by PCR—15 and 25 cycles

| | |
|---|---|
| Add to beads: | 98° C., 45 sec-hold |
| 50 µL 2X HiFi KAPA ready mix | 98° C., 15 sec |
| 2 µL PCR 1 | 60° C., 30 sec |
| 2 µL PCR 2 | 72° C., 30 sec |
| 46 µL nH$_2$O | 72° C., 60 sec-hold |
| 100 µL | 4 C.-hold |

Clean DNA (e.g. Zymo-25 column), elute 30 µL speedvac dry, resuspend 20 µL load onto 2% agarose gel. Cut 320-400 nucleotide area and gel extract DNA. DNA can be further processed and sequenced.

```
Universal blocker 1:
GATCGGAAGAGCACACGTCTGAACTCCAGTCAC555555ATCTCGTATGC
CGTCTTCTGCTTGX
```

```
Universal blocker 2:
CAAGCAGAAGACGGCATACGAGAT555555GTGACTGGAGTTCAGACGTG
TGCTCTTCCGATCX
```

The method can be used with approximately 10 kb region of the human CCLS gene. The method can also be performed with highly multiplexed short PCR reactions.

Example 13

A PCR reaction can be performed 2 times. 1 µL~1.2 µg gDNA (e.g. human brain DNA). Two uL of a 60 primer mix (25 uM stock) can be added with:

25 μL 2×KAPA HiFi
22 μL nH$_2$O
Total: 50 μL
PCR-10 cycles
98° C., 45 s
98° C., 15 s
47° C., 30 s
72° C., 30 s
72° C., 1 min
4° C.—hold Clean DNA (e.g. Zymo-25 clean-up), elute with 30 μL, and dry (e.g. using a speed vacuum). Load DNA on a 2% agarose, two wells, gel purify fragments between 300-600 nucleotides. Elute from gel, isolate using, e.g. Zymo-25, elute with 30 μLwater, speedvac to dry.

Fragmentation: resuspend all DNA in 50 μL 1×TE (with 2 ng/uL tRNA). Add to glass Covaris tube. Use settings: Duty Cycle 10%, Intensity 5, Cycles/Burst 200, time 120 s to shear DNA.

50 uL Fragmented DNA, 20 uL End Repair mix (8 uL water, 7 uL 10×KAPA end-repair, 5 uL KAPA enzymes). Incubate 20° C. for 30 minutes. Clean-up, add 120 μL AmpureXP beads to 70 uL=190 uL. Mix well, incubate 10 min let DNA bind. Move tube to magnet, remove liquid, 3 minutes. Wash beads with 200 μL 80% ethanol, wait 30 seconds, remove, repeat, 2 washes total. Allow beads dry 10 min.

Add beads from above. Allow beads to rehydrate for 3 minutes. 50 μL A-tailing master mix (42 uL water, 5 uL 10×KAPA A-tail, 3 uL KAPA A-tail enzyme). Mix well and incubate 30° C. for 30 minutes. Clean by adding 90 μL 20% PEG8000/2.5M NaCl solution. The total volume can be 140 μL, mix thoroughly via pipetting. Incubate 10 min let DNA bind. Move tube to magnet, remove liquid. Wash beads with 200 uL 80% ethanol, wait 30 seconds, remove, repeat, 2 washes total. Allow beads dry for 5 minutes. Ligate adapters. Add beads from above, allow beads rehydrate for 3 min.

45 μL Ligation master mix (30 μL water, 10 μL 5×KAPA Lig., 5 μL T4 DNA ligase).

3 μL adapters (1:10 dilution of standard) (final adapter conc. in reaction=0.3 uM)

Mix well and incubate 20° C. for 15 minutes. Wash 2 times. Add 50 μL 20% PEG8000/2.5M NaCl solution. Total volume 100 μL, mix thoroughly via pipetting. Incubate 10 minutes let DNA bind. Move tube to magnet, remove liquid. Wash beads with 200 μL 80% ethanol, wait 30 seconds, remove, repeat, 2 washes. Allow beads dry for 5 minutes. Resuspend beads in 50 μL water, wait 5 minutes. Add 50 μL 20% PEG8000/2.5M NaCl solution. Incubate 10 min let DNA bind. Move tube to magnet, remove liquid. Wash beads with 200 μL 80% ethanol, wait 30 seconds, remove, repeat, 2 washes total. Allow beads dry for 5 minutes. Resuspend beads 23 μL Tris pH 8, allow rehydrate 3 minutes. Collect DNA from elute and transfer to PCR tube. Enrich by PCR. Prepare the following PCR reaction mix in a 500 μL thin wall PCR tube.

| | |
|---|---|
| Use DNA from above | 23 μL |
| 2x HiFi KAPA Master Mix | 50 μL |
| Truseq PCR primer 1 | 2 μL |
| Truseq PCR primer 2 | 2 μL |
| Nuclease water | 23 μL |

Run the following PCR protocol 10 cycles:
45 sec at 98° C.
10 cycles of:
98° C., 15 sec
60° C., 30 sec
72° C., 30 sec
1 min at 72° C.
Hold at 4° C.

Purify the DNA (e.g. with Zymo (25) PCR Purification Kit) and elute in 30 μL dH$_2$O. Purify 10 cycle and 20 cycle material on, 2 wells per PCR, 4% agarose gel.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of generating a tagged nucleic acid library, comprising the steps of:
    annealing a first oligo population to a library template;
    performing library template-directed nucleic acid extension from the annealed first oligo population to produce a population of extension products;
    affinity tagging the population of extension products;
    terminating the library template-directed nucleic acid extension to produce a population of first extension products of indeterminate length, wherein at least some first extension products comprise at least 200 bp; and
    adding a second oligo sequence near the 3' end of the first extension product such that a tagged library of nucleic acid molecules is generated comprising nucleic acids each independently comprising a first oligo sequence, a template derived nucleic acid sequence of indeterminate length, and a second oligo sequence, wherein the first oligo population originates from a first random oligo population.

2. The method of claim 1, wherein said terminating the library template-directed nucleic acid extension comprises incorporation of a biotin tagged ddNTP.

3. The method of claim 1, wherein the affinity tagging comprises incorporating biotin bound to a dideoxy moiety at the 3' end extension.

4. The method of claim 1, comprising affinity purifying said first extension product.

5. The method of claim 1, wherein the library template-directed nucleic acid extension is performed with a DNA polymerase having strand-displacement activity.

6. The method of claim 5, wherein the DNA polymerase is capable of incorporating a biotin-labeled ddNTP at the 3' end of an extending nucleic acid.

7. The method of claim 1, wherein said adding a second oligo sequence near the 3' end of the first extension product comprises:
    annealing a population of oligos comprising said second oligo sequence to said first extension product; and
    contacting the composition to a nucleic acid extension cocktail comprising a DNA polymerase having strand-displacement activity to form a second extension product annealed to the first extension product.

8. The method of claim 1, comprising sequencing at least one member of the tagged library.

* * * * *

UNITED STATES PATENT AND TRADEMARK OFFICE
CERTIFICATE OF CORRECTION

PATENT NO. : 10,780,412 B2
APPLICATION NO. : 15/948459
DATED : September 22, 2020
INVENTOR(S) : Head et al.

Page 1 of 1

It is certified that error appears in the above-identified patent and that said Letters Patent is hereby corrected as shown below:

In the Specification

Column 1, Line 21, insert the paragraph below:
-- STATEMENT OF GOVERNMENT LICENSE RIGHTS
This invention was made with government support under grant number AI063603 awarded by The National Institutes of Health. The government has certain rights in the invention. --

Signed and Sealed this
Eighth Day of June, 2021

Drew Hirshfeld
*Performing the Functions and Duties of the
Under Secretary of Commerce for Intellectual Property and
Director of the United States Patent and Trademark Office*